(12) United States Patent
Philpot et al.

(10) Patent No.: US 9,714,427 B2
(45) Date of Patent: Jul. 25, 2017

(54) METHODS AND COMPOSITIONS FOR UNSILENCING IMPRINTED GENES

(75) Inventors: Benjamin David Philpot, Durham, NC (US); Mark John Zylka, Chapel Hill, NC (US); Bryan Leo Roth, Durham, NC (US); John Arthur Allen, North Billerica, MA (US); Hsien-Sung Huang, Kaohsiung (TW)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 546 days.

(21) Appl. No.: 13/883,621

(22) PCT Filed: Nov. 9, 2011

(86) PCT No.: PCT/US2011/059893
§ 371 (c)(1),
(2), (4) Date: Jul. 12, 2013

(87) PCT Pub. No.: WO2012/064806
PCT Pub. Date: May 18, 2012

(65) Prior Publication Data
US 2013/0317018 A1    Nov. 28, 2013

Related U.S. Application Data

(60) Provisional application No. 61/412,638, filed on Nov. 11, 2010.

(51) Int. Cl.
| | | |
|---|---|---|
| *A61K 31/473* | (2006.01) |
| *A61K 31/4741* | (2006.01) |
| *A61K 31/4745* | (2006.01) |
| *A61K 31/496* | (2006.01) |
| *A61K 31/5377* | (2006.01) |
| *A61K 31/7048* | (2006.01) |
| *A61K 31/7105* | (2006.01) |
| *A61K 31/713* | (2006.01) |
| *C12N 15/63* | (2006.01) |

(52) U.S. Cl.
CPC .......... *C12N 15/635* (2013.01); *A61K 31/473* (2013.01); *A61K 31/4741* (2013.01); *A61K 31/4745* (2013.01); *A61K 31/496* (2013.01); *A61K 31/5377* (2013.01); *A61K 31/7048* (2013.01); *A61K 31/713* (2013.01); *A61K 31/7105* (2013.01)

(58) Field of Classification Search
CPC .............. A61K 31/473; A61K 31/4741; A61K 31/4745; A61K 31/496; A61K 31/5377; A61K 31/7048; A61K 31/7105; A61K 31/713; C12N 15/635
See application file for complete search history.

(56) References Cited

U.S. PATENT DOCUMENTS

| 2007/0077553 A1 | 4/2007 | Bentwich |
| 2008/0138329 A1* | 6/2008 | Garcia Boy ......... C07D 209/48 424/94.6 |
| 2009/0076019 A1 | 3/2009 | Tyers et al. |
| 2010/0112038 A1 | 5/2010 | Schaebitz et al. |
| 2010/0113369 A1 | 5/2010 | Chauvier et al. |

OTHER PUBLICATIONS

Houtenbos et al., "Acute myeloid leukemia in a 23-year-old patient with Beckwith-Wiedemann Syndrome," Cancer Genetics and Cytogenetics (2002); 136: pp. 90-91.*
Abbas et al. "Assessing serotonin receptor mRNA editing frequency by a novel ultra high-throughput sequencing method" *Nucleic Acids Research* 38(10):e118 (2010).
Akbarian et al. "Epigenetic Regulation in Human Brain—Focus on Histone Lysine Methylation" *Biological Psychiatry* 65(3):198-203 (2009).
Albrecht et al. "Imprinted expression of the murine Angelman syndrome gene, Ube3a, in hippocampal and Purkinje neurons" *Nature Genetics* 17:75-78 (1997).
Alexander et al. "Remote control of neuronal activity in transgenic mice expressing evolved G protein-coupled receptors" *Neuron* 63(1):27-39 (2009).
Allen et al. "A novel small molecule screening approach to discover epigenetic regulators as therapeutics for Angelman syndrome" *ACNP 49th Annual Meeting* (1 page) (Abstract Only) (Aug. 12, 2010).
Arn et al. "Methylenetetrahydrofolate Reductase Deficiency in a Patient With Phenotypic Findings of Angelman Syndrome" *American Journal of Medical Genetics* 77:198-200 (1998).
Boege et al. "Selected Novel Flavones Inhibit the DNA Binding or the DNA Religation Step of Eukaryotic Topoisomerase I" *The Journal of Biological Chemistry* 271(4):2262-2270 (1996).
Bomgaars et al. "The Development of Camptothecin Analogs in Childhood Cancers" *The Oncologist* 6:506-516 (2001).
Bressler et al. "The SNRPN promoter is not required for genomic imprinting of the Prader-Willi/Angelman domain in mice" *Nature Genetics* 28:232-240 (2001).
Browne et al. "Inherited Interstitial Duplications of Proximal 15q: Genotype-Phenotype Correlations" *The American Journal of Human Genetics* 61:1342-1352 (1997).
Butler, Merlin G. "Genomic imprinting disorders in humans: a mini-review" *Journal of Assisted Reproduction and Genetics* 26:477-486 (2009).
Cantero et al. "Topoisomerase II inhibition and high yield of endoreduplication induced by the flavonoids luteolin and quercetin" *Mutagenesis* 21(5):321-325 (2006).

(Continued)

*Primary Examiner* — Sreeni Padmanabhan
*Assistant Examiner* — Jody Karol
(74) *Attorney, Agent, or Firm* — Myers Bigel, P.A.

(57) ABSTRACT

The present invention provides methods and compositions for inducing expression of Ube3a in a cell by contacting the cell with a topoisomerase inhibitor. Particular embodiments include a method of treating a genomic imprinting disorder, such as Angelman syndrome, in a subject by administering to the subject an effective amount of a topoisomerase inhibitor.

5 Claims, 40 Drawing Sheets

(56) References Cited

OTHER PUBLICATIONS

Carol et al. "Initial Testing of Topotecan by the Pediatric Preclinical Testing Program" *Pediatric Blood & Cancer* 54(5):707-715 (2010).
Clayton-Smith et al. "Angelman syndrome: a review of the clinical and genetic aspects" *Journal of Medical Genetics* 40:87-95 (2003).
Collins et al. "Transcriptional Consequences of Topoisomerase Inhibition" *Molecular and Cellular Biology* 21(24):8437-8451 (2001).
Cook et al. "Autism or Atypical Autism in Maternally but Not Paternally Derived Proximal 15q Duplication" *The American Journal of Human Genetics* 60:928-934 (1997).
Corbett et al. "Structure, Molecular Mechanisms, and Evolutionary Relationships in DNA Topoisomerases" *Annual Review of Biophysics and Biomolecular Structure* 33:95-118 (2004).
Crinelli et al. "Ubiquitin over-expression promotes E6AP autodegradation and reactivation of the p53/MDM2 pathway in HeLa cells" *Molecular and Cellular Biochemistry* 318:129-145 (2008).
Cruz-Correa et al. "Temporal stability and age-related prevalence of loss of imprinting of the insulin-like growth factor-2 gene" *Epigenetics* 4(2):114-118 (2009).
Cushman et al. "Synthesis of New Ideno[1,2-c]isoquinolines: Cytotoxic Non-Camptothecin Topoisomerase I Inhibitors" *Journal of Medicinal Chemistry* 43:3688-3698 (2000).
Dan, Bernard "Angelman syndrome: Current understanding and research prospects" *Epilepsia* 50(11):2331-2339 (2009).
Dindot et al. "The Angelman syndrome ubiquitin ligase localizes to the synapse and nucleus, and maternal deficiency results in abnormal dendritic spine morphology" *Human Molecular Genetics* 17(1):111-118 (2008).
Ehninger et al. "Reversing Neurodevelopmental Disorders in Adults" *Neuron* 60:950-960 (2008).
Elphick et al. "The Human Polyomavirus, JCV, Uses Serotonin Receptors to Infect Cells" *Science* 306:1380-1383 (2004).
Feun et al. "Topoisomerase I inhibitors for the treatment of brain tumors" *Expert Review of Anticancer Therapy* 8(5):707-716 (2008).
Gammon et al. "Intrathecal topotecan in adult patients with neoplastic meningitis" *American Journal of Health-System Pharmacy* 63:2083-2086 (2006).
Gaulton et al. "A map of open chromatin in human pancreatic islets" *Nature Genetics* 43(3):255-259 (2010).
Glenn et al. "Modification of 15q11-q13 DNA methylation imprints in unique Angelman and Prader-Willi patients" *Human Molecular Genetics* 2(9):1377-1382 (1993).
Glenn et al. "Genomic imprinting: potential function and mechanisms revealed by the Prader-Willi and Angelman syndromes" *Molecular Human Reproduction* 3(4):321-332 (1997).
Greer et al. "The Angelman Syndrome-associated ubiquitin ligase Ube3A regulates synapse development by ubiquitinating Arc" *Cell* 140(5):704-716 (2010).
Guy et al. "Reversal of Neurological Defects in a Mouse Model of Rett Syndrome" *Science* 315:1143-1147 (2007).
Hartmann et al. "Camptothecin and Podophyllotoxin Derivatives: Inhibitors of Topoisomerase I and II—Mechanisms of Action, Pharmacokinetics and Toxicity Profile" *Drug Safety* 29(3):209-230 (2006).
He et al. "Nucleosome Dynamics Define Transcriptional Enhancers" *Nature Genetics* 42(4):343-347 (2010).
Herben et al. "Clinical pharmacokinetics of camptothecin topoisomerase I inhibitors" *Pharmacy World & Science* 20(4):161-172 (1998).
Hertzberg et al. "Modification of the Hydroxy Lactone Ring of Camptothecin: Inhibition of Mammalian Topoisomerase I and Biological Activity" *Journal of Medicinal Chemistry* 32(3):715-720 (1989).
Huang et al. "GAD1 mRNA Expression and DNA Methylation in Prefrontal Cortex of Subjects with Schizophrenia" *PLoS ONE* 8:e809 (2007).

Huang et al. "Prefrontal Dysfunction in Schizophrenia Involves Mixed-Lineage Leukemia 1-Regulated Histone Methylation at GABAergic Gene Promoters" *The Journal of Neuroscience* 27(42):11254-11262 (2007).
Huang et al. "Parallel Functional Activity Profiling Reveals Valvulopathogens Are Potent 5-Hydroxytryptamine$_{2B}$ Receptor Agonists: Implications for Drug Safety Assessment" *Molecular Pharmacology* 76:710-722 (2009).
Huang et al. "A small molecule screening approach for identifying Angelman syndrome therapeutics" 40$^{th}$ Annual Meeting, Neuroscience (Presentation Abstract) (1 page) (downloaded from www.abstractsonline.com Oct. 29, 2010).
Huang et al. "Behavioral deficits in an Angelman syndrome model: Effects of genetic background and age" *Behavioural Brain Research* 243:79-90 (2013).
Jiang et al. "Mutation of the Angelman Ubiquitin Ligase in Mice Causes Increased Cytoplasmic p53 and Deficits of Contextual Learning and Long-Term Potentiation" *Neuron* 21:799-811 (1998).
Keiser et al. "Predicting new molecular targets for known drugs" *Nature* 462:175-181 (2009).
Kim et al. "Polyubiquitination by HECT E3s and the Determinants of Chain Type Specificity" *Molecular and Cellular Biology* 29(12):3307-3318 (2009).
Kirkwood et al. "Common Forms of Synaptic Plasticity in the Hippocampus and Neocortex in Vitro" *Science* 260:1518-1521 (1993).
Kishino et al. "UBE3A /E6-AP mutations cause Angelman syndrome" *Nature Genetics* 15:70-73 (1997).
Koster et al. "Antitumour drugs impede DNA uncoiling by topoisomerase I" *Nature* 448:213-217 (2007).
Kumar et al. "Physical Interaction between Specific E2 and Hect E3 Enzymes Determines Functional Cooperativity" *The Journal of Biological Chemistry* 272(21):13548-13554 (1997).
Kunimoto et al. "Antitumor Activity of 7-Ethyl-10-[4-(1-piperidino)-1-piperidino]carbonyloxy-camptothecin, a Novel Water-soluble Derivative of Camptothecin, against Murine Tumors" *Cancer Research* 47:5944-5947 (1987).
Landers et al. "Regulation of the large (~1000 kb) imprinted murine Ube3a antisense transcript by alternative exons upstream of Snurf/Snrpn " *Nucleic Acids Research* 32(11):3480-3492 (2004).
Leone et al. "Resveratrol induces DNA double-strand breaks through human topoisomerase II interaction" *Cancer Letters* 295:167-172 (2010).
Liu et al. "Supercoiling of the DNA template during transcription" *Proceedings of the National Academy of Sciences* 84:7024-7027 (1987).
Lopez-Lazarq et al. "Green tea constituents (-)-epigallocatechin-3-gallate (EGCG) and gallic acid induce topoisomerase I- and topoisomerase II-DNA complexes in cells mediated by pyrogallol-induced hydrogen peroxide" *Mutagenesis* 26(4):489-498 (2011).
Lossie et al. "Distinct phenotypes distinguish the molecular classes of Angelman syndrome" *Journal of Medical Genetics* 38:834-845 (2001).
Lyu et al. "Role of Topoisomerase Iβ in the Expression of Developmentally Regulated Genes" *Molecular and Cellular Biology* 26(21):7929-7941 (2006).
Mabb et al. "Angelman Syndrome: Insights into Genomic Imprinting and Neurodevelopmental Phenotypes" *Trends in Neurosciences* 34(6):293-303 (2011).
Markovits et al. "Inhibitory Effects of the Tyrosine Kinase Inhibitor Genistein on Mammalian DNA Topoisomerase II" *Cancer Research* 49:5111-5117 (1989).
Matsuura et al. "De novo truncating mutations in E6-AP ubiquitin-protein ligase gene (UBE3A) in Angelman syndrome" *Nature Genetics* 15:74-77 (1997).
Moeschler et al. "Estimate of Prevalence of Proximal 15q Duplication Syndrome" *American Journal of Medical Genetics* 111:440-442 (2002).
Motl et al. "Pharmacokinetic Considerations in the Treatment of CNS Tumours" *Clinical Pharmacokinetics* 45(9):871-903 (2006).
Moy et al. "Sociability and preference for social novelty in five inbred strains: an approach to assess autistic-like behavior in mice" *Genes, Brain and Behavior* 3:287-302 (2004).

(56) References Cited

OTHER PUBLICATIONS

Moy et al. "Mouse Models of Autism Spectrum Disorders: The Challenge for Behavioral Genetics" *American Journal of Medical Genetics Part C (Semin. Med. Genet.)* 142C:40-51 (2006).
Moy et al. "Mouse Behavioral Tasks Relevant to Autism: Phenotypes of Ten Inbred Strains" *Behavioral Brain Research* 176(1):4-20 (2007).
Moy et al. "Advances in behavioral genetics: mouse models of autism" *Molecular Psychiatry* 13:4-26 (2008).
Moy et al. "Social Approach in Genetically-Engineered Mouse Lines Relevant to Autism" *Genes, Brain and Behavior* 8(2):129-142 (2009).
Nagarajan et al. "Synthesis and Evaluation of Indenoisoquinoline Topoisomerase I Inhibitors Substituted with Nitrogen Heterocycles" *Journal of Medicinal Chemistry* 49(21):6283-6289 (2006).
Nakatani et al. "Abnormal Behavior in a Chromosome-Engineered Mouse Model for Human 15q11-13 Duplication Seen in Autism" *Cell* 137:1235-1246 (2009).
Numata et al. "Highly parallel SNP genotyping reveals high-resolution landscape of mono-allelic Ube3a expression associated with locus-wide antisense transcription" *Nucleic Acids Research* 39(7):2649-2657 (2011).
O'Connor et al. "Finding New Tricks for Old Drugs: An Efficient Route for Public-Sector Drug Discovery" *Nature Reviews Drug Discovery* 4:1005-1014 (2005).
Peery et al. "A targeted deletion upstream of Snrpn does not result in an imprinting defect" *Mammalian Genome* 18:255-262 (2007).
Pelc et al. "Behavior and neuropsychiatric manifestations in Angelman syndrome" *Neuropsychiatric Disease and Treatment* 4(3):577-584 (2008).
Peters et al. "Double-Blind Therapeutic Trial in Angelman Syndrome Using Betaine and Folic Acid" *American Journal of Medical Genetics Part A* 152A(8):1994-2001 (2010).
Philpot et al. "Obligatory role of NR2A for metaplasticity in visual cortex" *Neuron* 53(4):495-502 (2007).
Philpot, Ben "An Integrated Chemical Biology Approach for Discovering Autism and Angelman Syndrome Therapeutics" *Presentation Slides* (24 pages) (Sep. 14, 2010).
Philpot, Ben "A New Angle on Angelman Syndrome" *Presentation Slides* (70 pages) (Oct. 6, 2010).
Philpot, Ben "A New Angle on Angelman Syndrome" *Presentation Slides* (38 pages) (Nov. 9, 2010).
Plaschkes et al. "DNA Topoisomerase I in the Mouse Central Nervous System: Age and Sex Dependence" *The Journal of Comparative Neurology* 493:357-369 (2005).
Pommier, Yves "Topoisomerase I inhibitors: camptothecins and beyond" *Nature Reviews Cancer* 6:789-802 (2006).
Reik, Wolf "Stability and flexibility of epigenetic gene regulation in mammalian development" *Nature* 447:425-432 (2007).
Roberts et al. "Characterisation of interstitial duplications and triplications of chromosome 15q11-q13" *Human Genetics* 110:227-234 (2002).
Rodriguez-Galindo et al. "Clinical Use of Topoisomerase I Inhibitors in Anticancer Treatment" *Medical and Pediatric Oncology* 35:365-402 (2000).
Roth et al. "Magic shotguns versus magic bullets: selectively non-selective drugs for mood disorders and schizophrenia" *Nature Reviews Drug Discovery* 3:353-359 (2004).
Rougeulle et al. "The Angelman syndrome candidate gene, UBE3A/E6-AP, is imprinted in brain" *Nature Genetics* 17:14-15 (1997).
Rougeulle et al. "An imprinted antisense RNA overlaps UBE3A and a second maternally expressed transcript" *Nature Genetics* 19:15-16 (1998).
Runte et al. "The IC-SNURF-SNRPN transcript serves as a host for multiple small nucleolar RNA species and as an antisense RNA for UBE3A" *Human Molecular Genetics* 10(23):2687-2700 (2001).
Sato et al. "Genomic imprinting of experience-dependent cortical plasticity by the ubiquitin ligase gene Ube3a" *Proceedings of the National Academy of Sciences* 107(12):5611-5617 (2010).

Sawtell et al. "NMDA Receptor-Dependent Ocular Dominance Plasticity in Adult Visual Cortex" *Neuron* 38:977-985 (2003).
Scheffner et al. "Protein ubiquitination involving an E1-E2-E3 enzyme ubiquitin thioester cascade" *Nature* 373:81-83 (1995).
Schellens et al. "Bioavailability and pharmacokinetics of oral topotecan: a new topoisomerase I inhibitor" *British Journal of Cancer* 73:1268-1271 (1996).
Schroer et al. "Autism and Maternally Derived Aberrations of Chromosome 15q" *American Journal of Medical Genetics* 76:327-336 (1998).
Snyder et al. "Evaluation of the Clastogenic, DNA Intercalative, and Topoisomerase II-Interactive Properties of Bioflavonoids in Chinese Hamster V79 Cells" *Environmental and Molecular Mutagenesis* 40:266-276 (2002).
Soejima et al. "Imprinting Centers, Chromatin Structure, and Disease" *Journal of Cellular Biochemistry* 95:226-233 (2005).
Souza et al. "SW-620 cells treated with topoisomerase I inhibitor SN-38: gene expression profiling" *Journal of Translational Medicine* 3(44):1-7 (2005).
Stewart et al. "Topoisomerase I interactive drugs in children with cancer" *Investigational New Drugs* 14:37-47 (1996).
Sutcliffe et al. "Deletions of a differentially methylated CpG island at the SNRPN gene define a putative imprinting control region" *Nature Genetics* 8:52-58 (1994).
Sutcliffe et al. "The E6-AP Ubiquitin-Protein Ligase (UBE3A) Gene is Localized within a Narrowed Angelman Syndrome Critical Region" *Genome Research* 7:368-377 (1997).
Tilghman et al. "The Sins of the Fathers and Mothers: Genomic Imprinting in Mammalian Development" *Cell* 96:185-193 (1999).
Tsai et al. "Necdin-deficient mice do not show lethality or the obesity and infertility of Prader-Willi syndrome" *Nature Genetics* 22:15-16 (1999).
Van Woerden et al. "Rescue of neurological deficits in a mouse model for Angelman syndrome by reduction of αCaMKII inhibitory phosphorylation" *Nature Neuroscience* 10(3):280-282 (2007).
Vu et al. "Imprinting of the Angelman syndrome gene, UBE3A, is restricted to brain" *Nature Genetics* 17:12-13 (1997).
Wang, James C. "Cellular Roles of DNA Topoisomerases: A Molecular Perspective" *Nature Reviews Molecular Cell Biology* 3:430-440 (2002).
Wang et al. "Transcriptome-Wide Identification of Novel Imprinted Genes in Neonatal Mouse Brain" *PLoS ONE* 3(12):e3839 (2008).
Watanabe et al. "Genome-wide analysis of expression modes and DNA methylation status status at sense-antisense transcript loci in mouse" *Genomics* 96:333-341 (2010).
Weeber et al. "Derangements of Hippocampal Calcium/Calmodulin-Dependent Protein Kinase II in a Mouse Model for Angelman Mental Retardation Syndrome" *The Journal of Neuroscience* 23(7):2634-2644 (2003).
Yashiro et al. "Ube3a is required for experience-dependent maturation of the neocortex" *Nature Neuroscience* 12(6):777-783 (2009).
Zhang et al. "A Simple Statistical Parameter for Use in Evaluation and Validation of High Throughput Screening Assays" *Journal of Biomolecular Screening* 4(2):67-73 (1999).
Zori et al. "Angelman Syndrome: Clinical Profile" *Journal of Child Neurology* 7:270-280 (1992).
Beaudenon et al. "Expression and Assay of HECT Domain Ligases" *Methods in Enzymology* 398:112-125 (2005).
Berger et al. "Green Tea Constituent (-)-Epigallocatechin-3-gallate Inhibits Topoisomerase I Activity in Human Colon Carcinoma Cells" *Biochemical and Biophysical Research Communications* 288:101-105 (2001).
Chamberlain et al. "The Prader-Willi Syndrome Imprinting Center Activates the Paternally Expressed Murine Ube3a Antisense Transcript but Represses Paternal Ube3a" *Genomics* 73:316-322 (2001).
Creemers et al. "Phase I and Pharmacologic Study of Oral Topotecan Administered Twice Daily for 21 Days to Adult Patients With Solid Tumors" *Journal of Clinical Oncology* 15(3):1087-1093 (1997).
Herben et al. "Clinical pharmacokinetics of topotecan" *Clinical pharmacokinetics* 31(2):85-102 (1996) (Abstract Only).

(56) References Cited

OTHER PUBLICATIONS

Huang et al. "Chromatin immunoprecipitation in postmortem brain" *Journal of Neuroscience Methods* 156:284-292 (2006).

Kim et al. "Potentiation of radiation response in human carcinoma cells in vitro and murine fibrosarcoma in vivo by topotecan, an inhibitor of DNA topoisomerase I" *International Journal of Radiation Oncology, Biology, Physics* 22(3):515-518 (1992) (Abstract Only).

Lopez-Lazaro et al. "The dietary flavonoids myricetin and fisetin act as dual inhibitors of DNA topoisomerases I and II in cells" *Mutation Research* 696:41-47 (2010).

Miura et al. "Neurobehavioral and Electroencephalographic Abnormalities in Ube3a Maternal-Deficient Mice" *Neurobiology of Disease* 9:149-159 (2002).

Morison et al. "Insulin-like growth factor 2 and overgrowth: molecular biology and clinical implications" *Molecular Medicine Today* 4(3):110-115 (1998).

Rodriguez-Galindo et al. "Hematologic Abnormalities and Acute Myeloid Leukemia in Children and Adolescents Administered Intensified Chemotherapy for the Ewing Sarcoma Family of Tumors" *Journal of Pediatric Hematology/Oncology* 22(4):321-329 (2000).

Rose et al. "Sequential prolonged oral topotecan and prolonged oral etoposide as second-line therapy in ovarian or peritoneal carcinoma: A phase I Gynecologic Oncology Group study" *Gynecologic Oncology* 102:236-239 (2006).

Seiter, Karen "Toxicity of the topoisomerase I inhibitors" *Expert Opinion on Drug Safety* 4(1):45-53 (2005) (Abstract Only).

Snyder et al. "Reduction of genistein clastogenicity in Chinese hamster V79 cells by daidzein and other flavonoids" *Food and Chemical Toxicology* 41:1291-1298 (2003).

Steffenburg et al. "Autism in Angelman Syndrome: A Population-Based Study" *Pediatric Neurology* 14(2):131-136 (1996).

Trushina et al. "Neurological abnormalities in caveolin-1 knock out mice" *Behavioural Brain Research* 172:24-32 (2006).

Vassal et al. "Preclinical development of camptothecin derivatives and clinical trials in pediatric oncology" *Biochimie* 80:271-280 (1998).

Wagstaff et al. "The $GABA_A$ Receptor β3 Subunit Gene: Characterization of a Human cDNA from Chromosome 15q11q13 and Mapping to a Region of Conserved Synteny on Mouse Chromosome 7" *Genomics* 11:1071-1078 (1991).

Williams, Charles A. "Neurological aspects of the Angelman syndrome" *Brain & Development* 27:88-94 (2005).

International Preliminary Report on Patentability issued for PCT Application No. PCT/US2011/059893 mailed May 23, 2013 (7 pages).

International Search Report and Written Opinion dated Jul. 2, 2012 for International Application No. PCT/US2011/059893 (11 pages).

Chamberlain et al. "Angelman Syndrome, a Genomic Imprinting Disorder of the Brain" *The Journal of Neuroscience* 30(30):9958-9963 (2010).

Huang et al. "Topoisomerase Inhibitors Unsilence the Dormant Allele of Ube3a in Neurons" *Nature* 481:185-191 (2012).

James "Prolonged Survival in a Patient with BRCA2 Associated Metastatic Pancreatic Cancer After Exposure to Camptothecin: A Case Report and Review of Literature" *Anti-Cancer Drugs* 20:634-638 (2009).

Kerzendorfer et al. "Mutations in Cullin 4B Result in a Human Syndrome Associated with Increased Camptothecin-Induced Topoisomerase I-Dependent DNA Breaks" *Human Molecular Genetics* 19(7):1324-1334 (2010).

Peters et al. "Double-Blind Therapeutic Trial in Angelman Syndrome Using Betaine and Folic Acid" *Am J Med Genet A.* 152A(8):1994-2001 (2010).

* cited by examiner

Fig. 13D
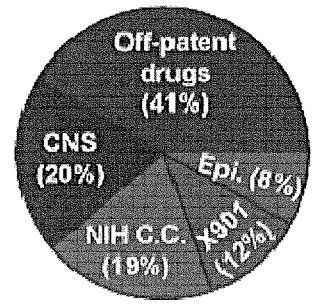
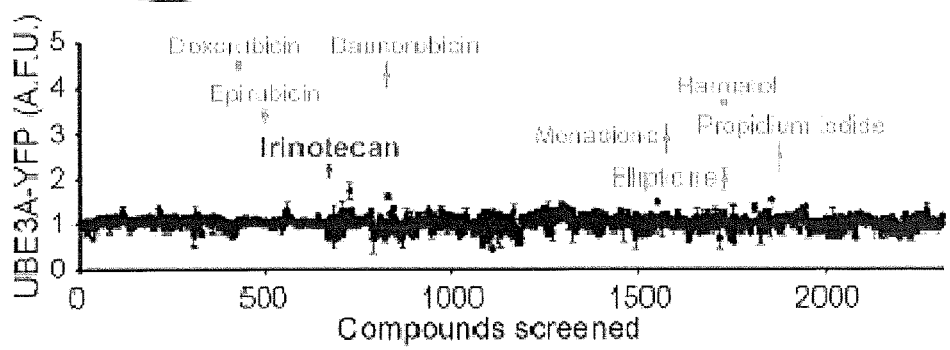
Fig. 13E
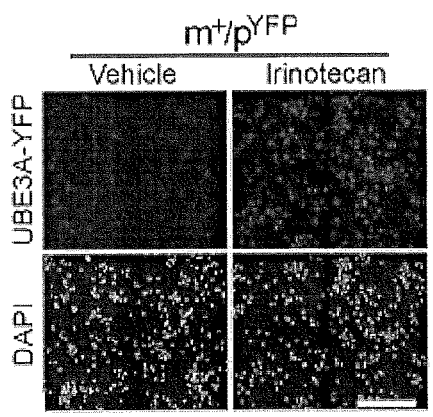
Fig. 13F
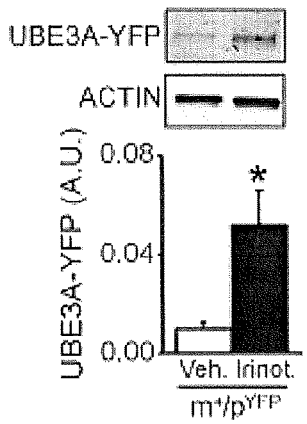
Fig. 13G
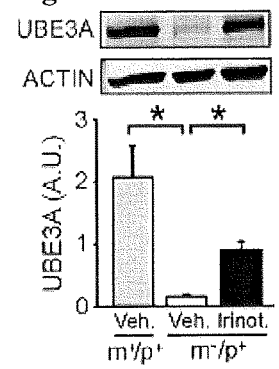

|  | DMSO | Irinotecan |
|---|---|---|
| YFP, MEAN circle intensity | 602 ± 16 | 1314 ± 81 |
| N (cells) | 3853 | 4230 |
| YFP MEAN intensity normalized to DMSO | 1.00 ± 0.03 | 2.18 ± 0.13 |

Fig. 19A
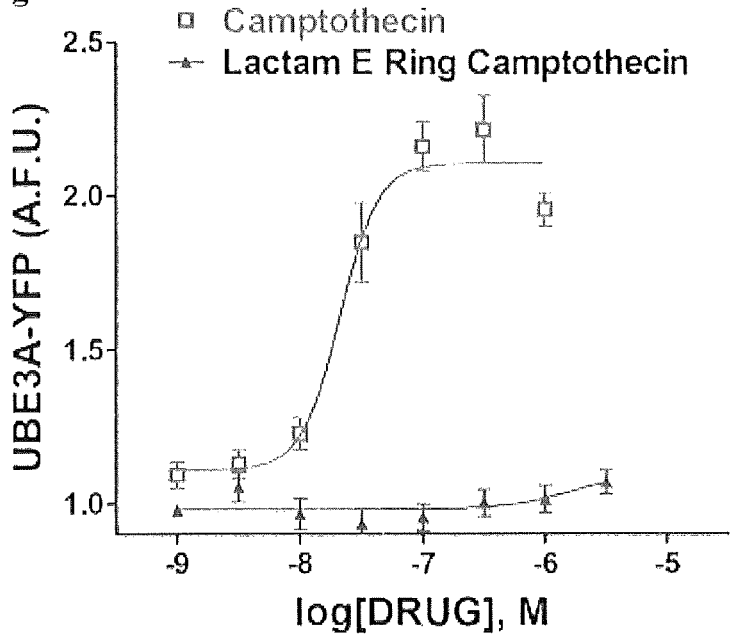
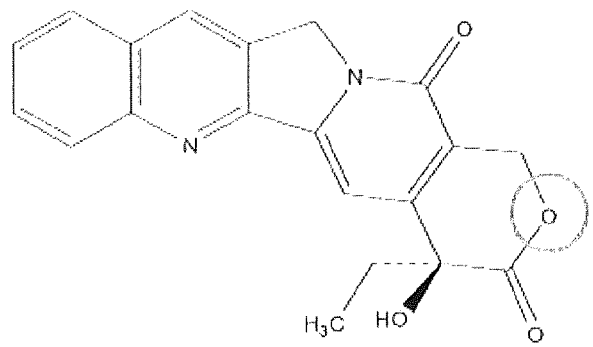
Camptothecin
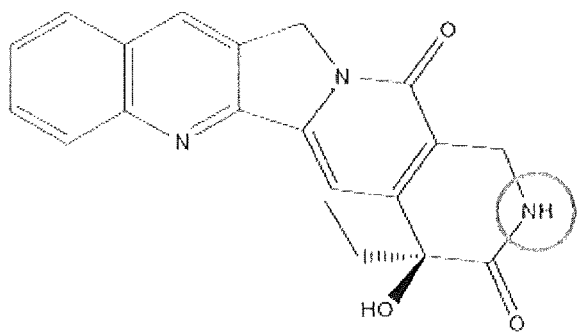
Lactam E Ring
Camptothecin Fig. 19B
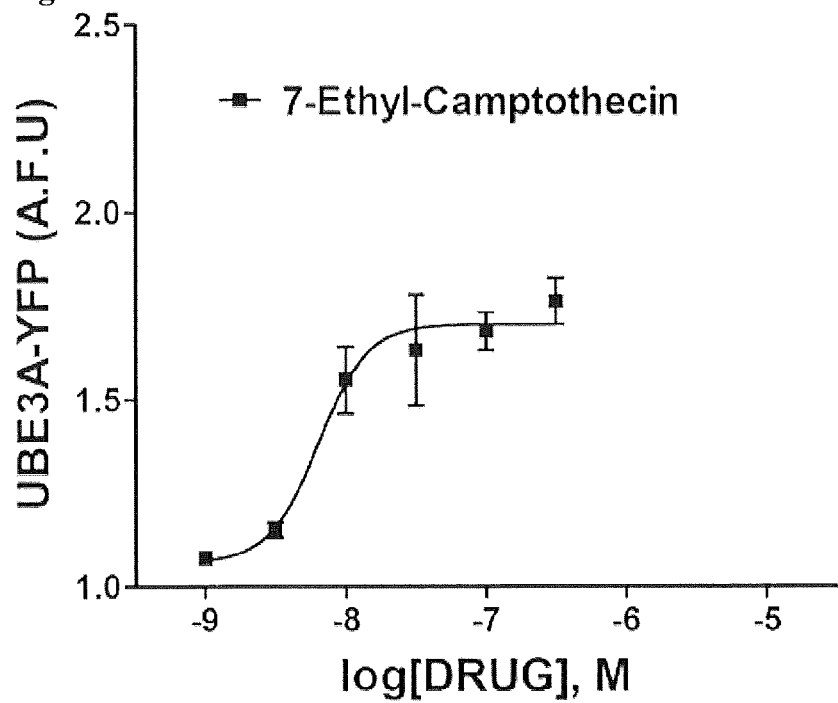
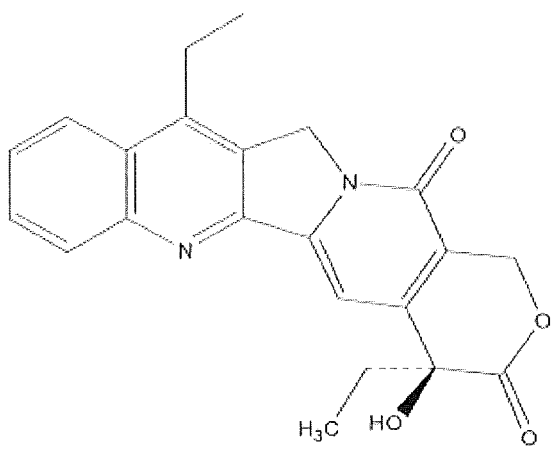
7-Ethyl-Camptothecin Fig. 20A
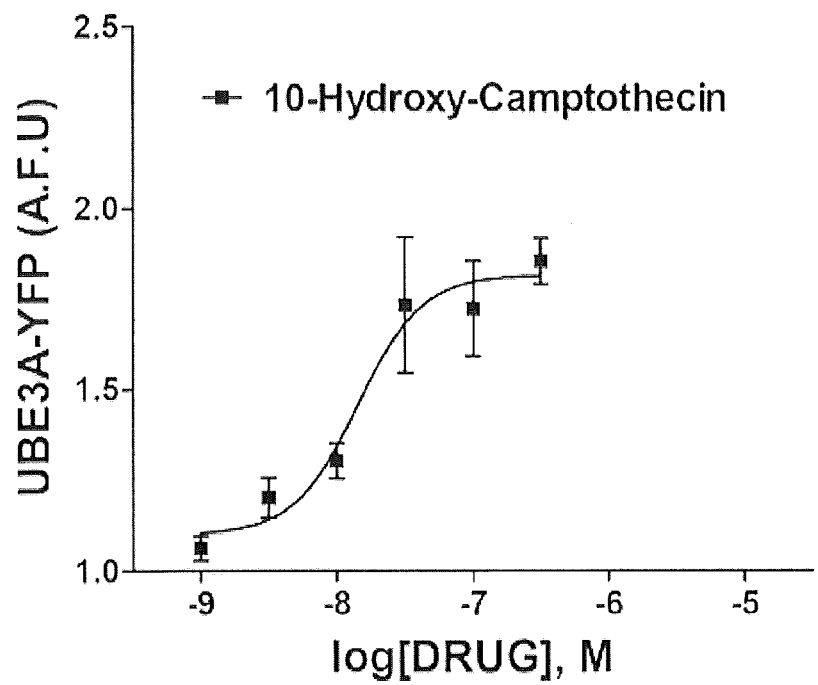
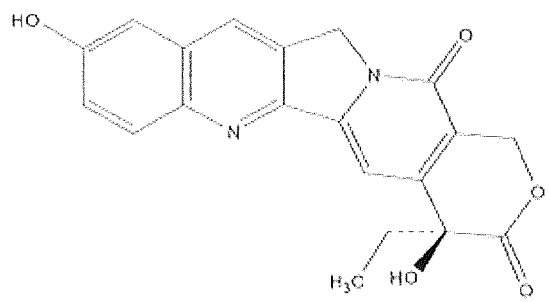
10-Hydroxy-Camptothecin Fig. 20B
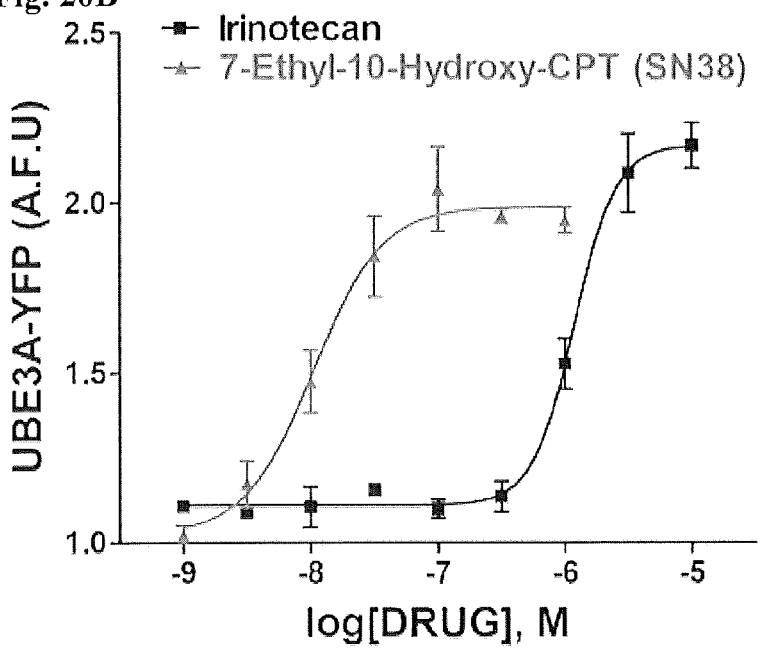
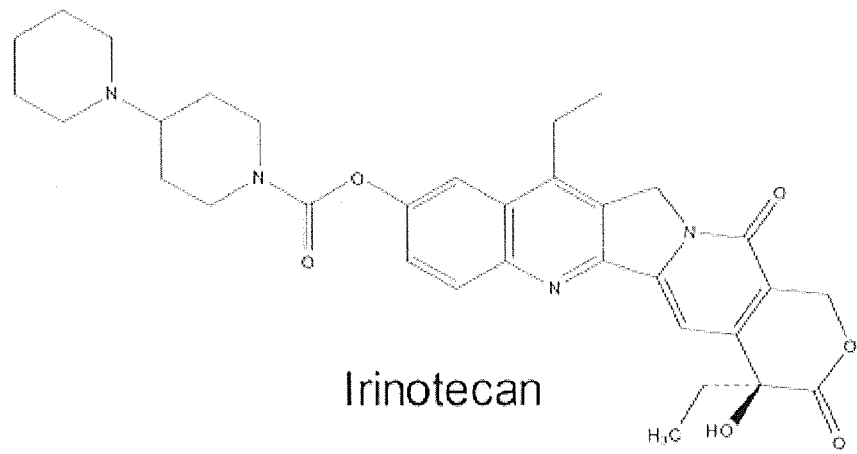
Irinotecan
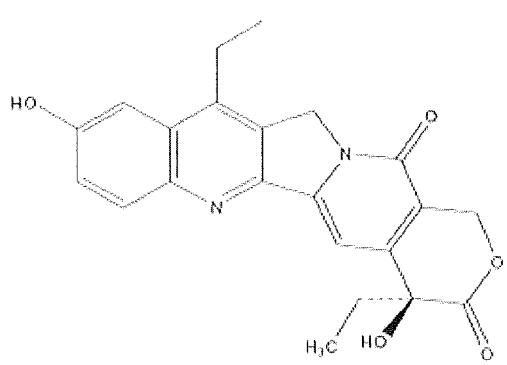
7-Ethyl-10-Hydroxy-
Camptothecin (SN38)

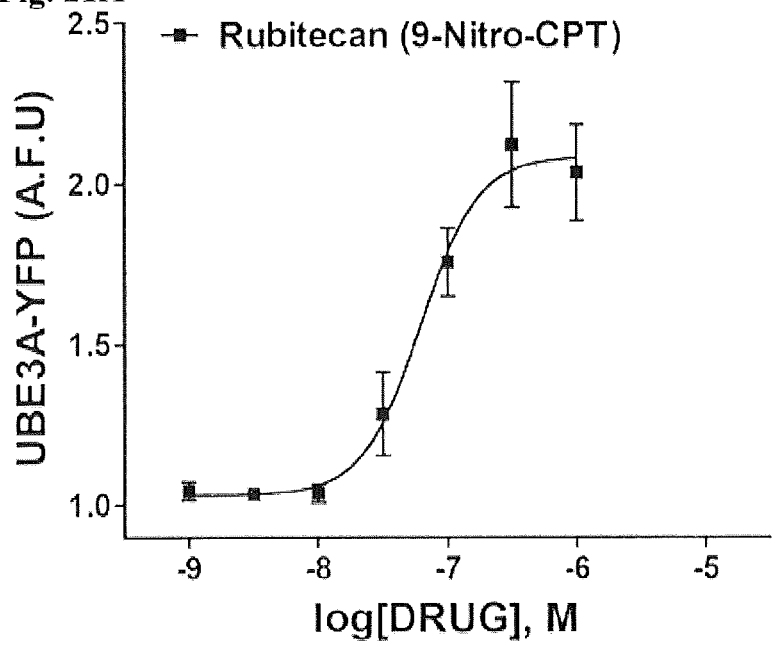
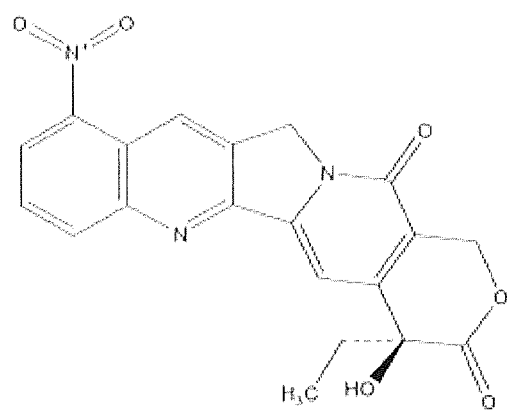
9-Nitro-Camptothecin

Fig. 21B
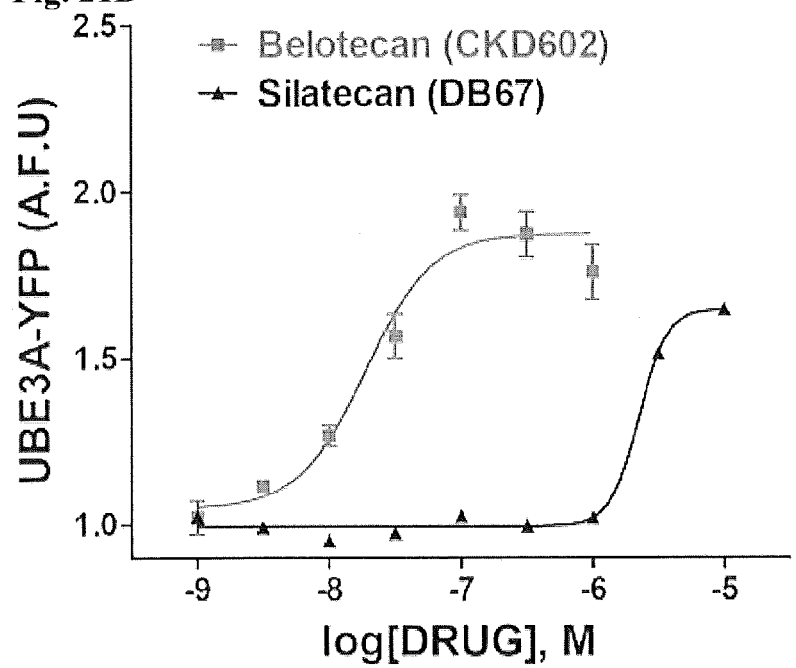
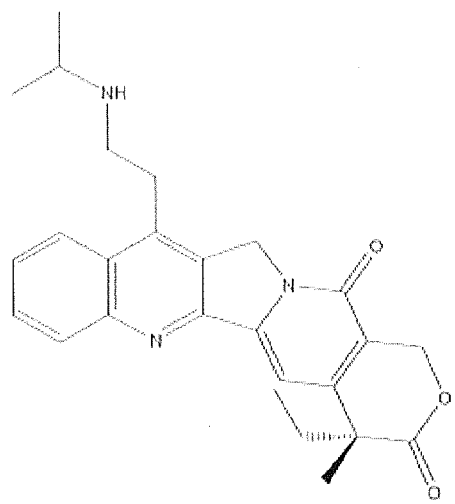
Belotecan (CKD602)
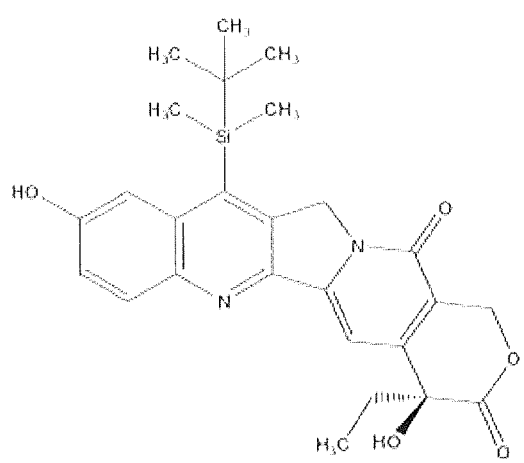
Silatecan (DB67)

Fig. 22A
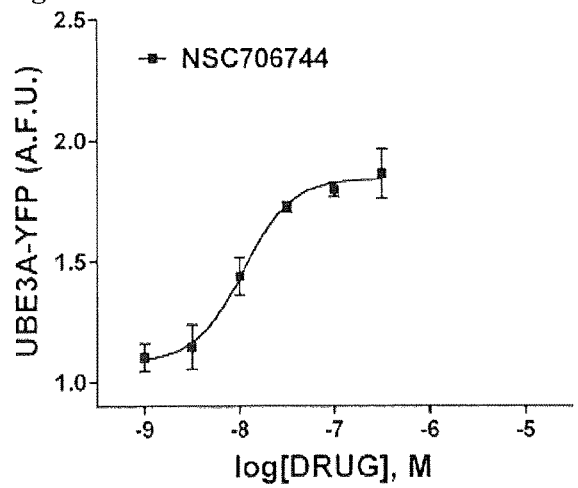
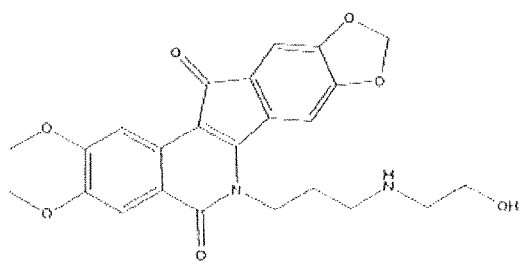
NSC706744
Fig. 22B
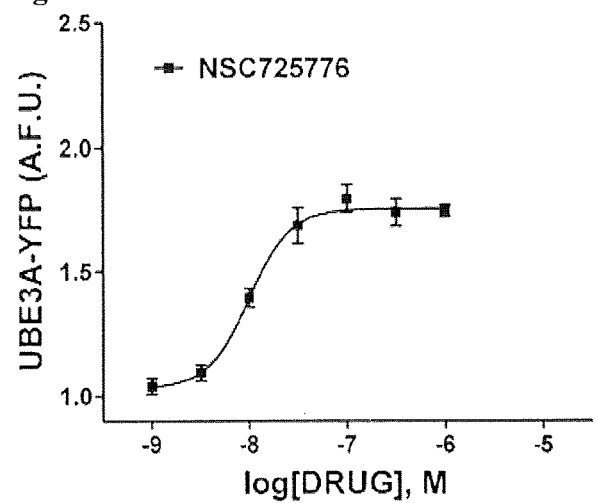
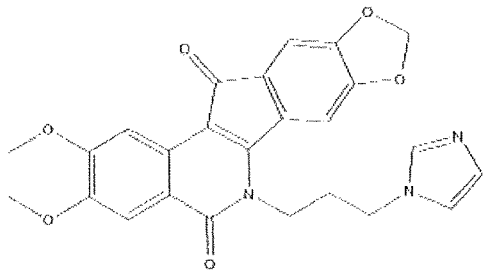
NSC725776

Fig. 23
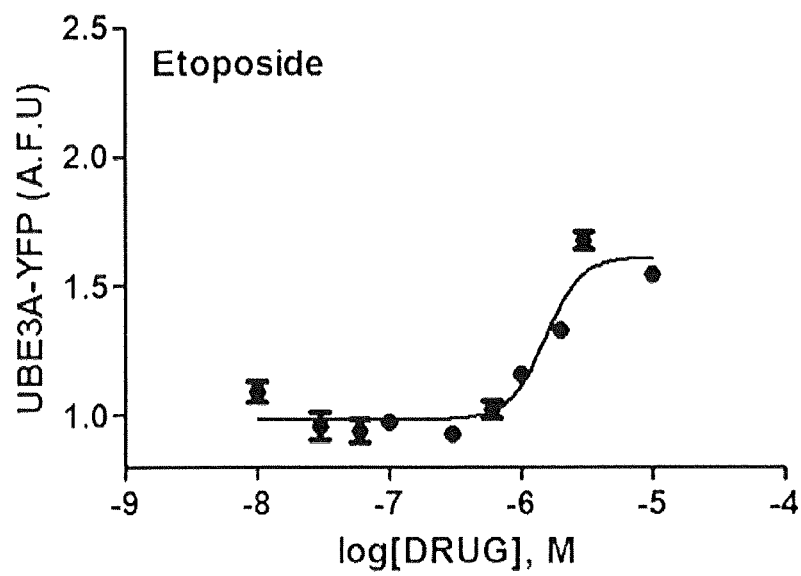
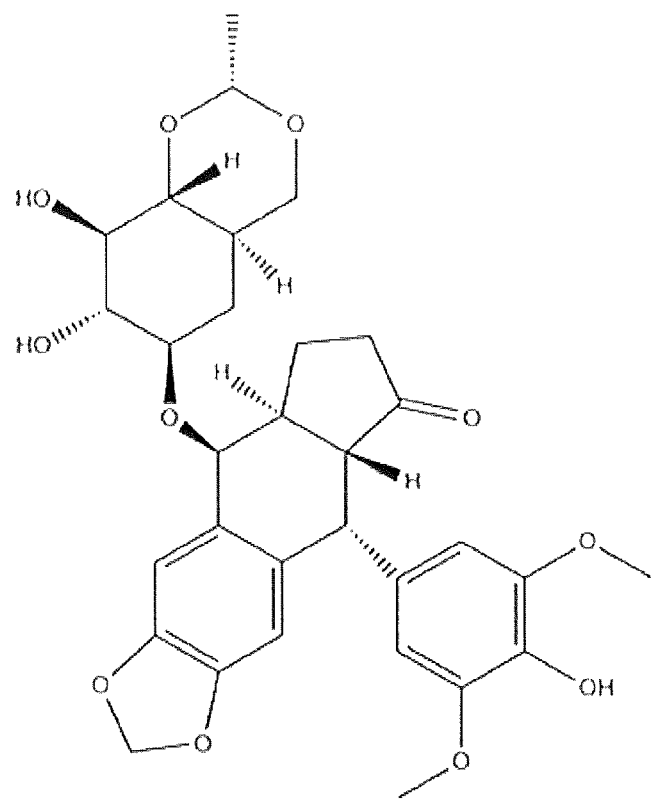

Fig. 24A
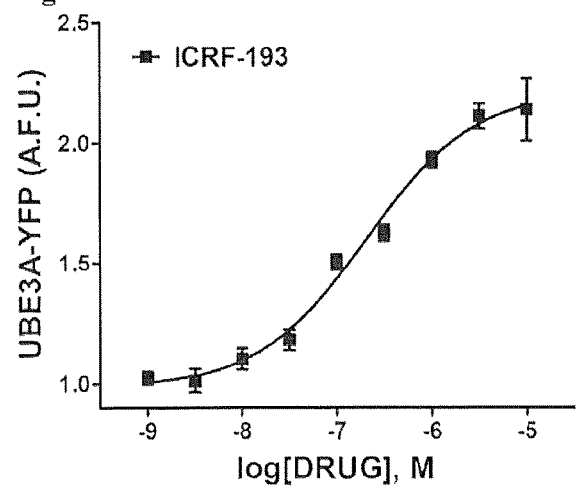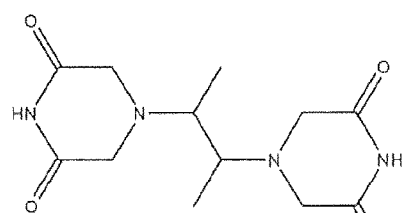
ICRF-193
Fig. 24B
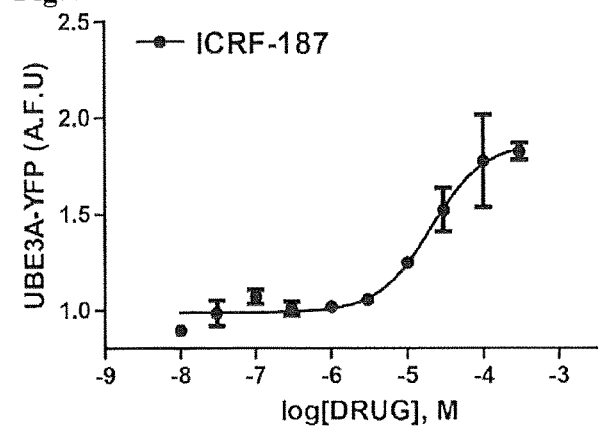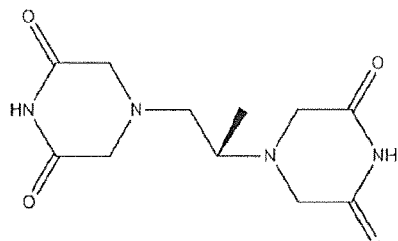
ICRF-187

Fig. 25
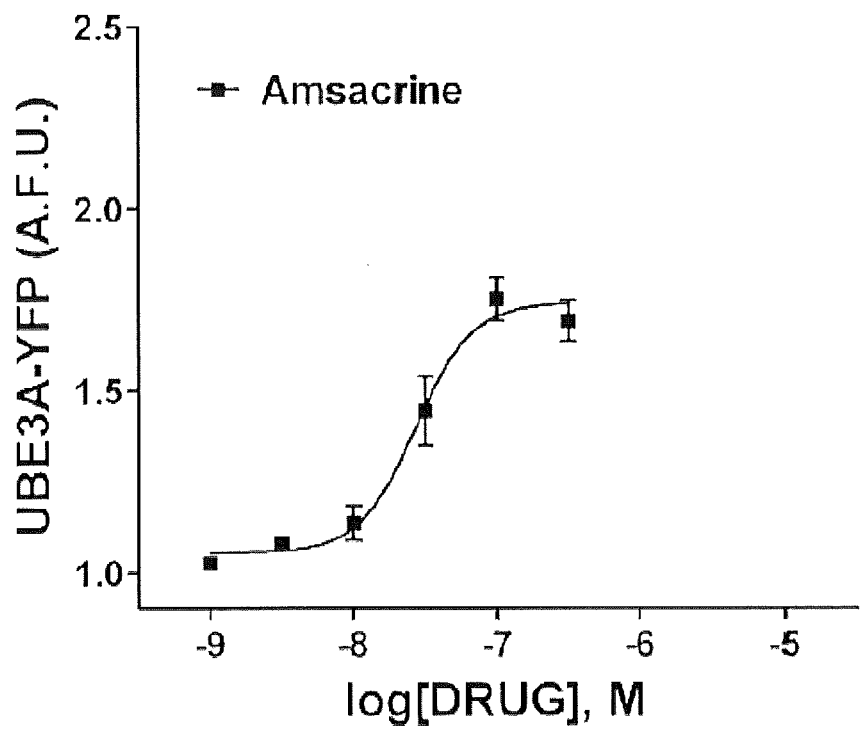
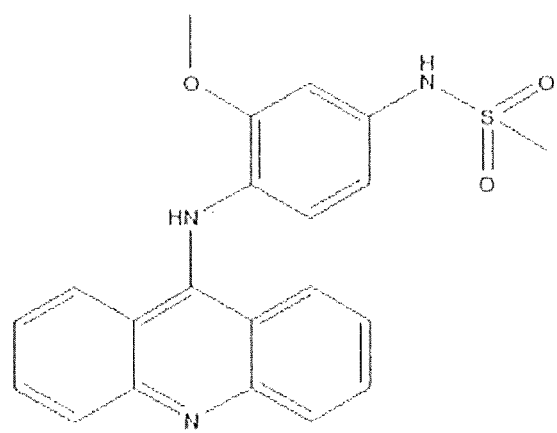

| Treatment | Vehicle | Topotecan |
|---|---|---|
| Genotype | mYFP/p+ | p+/mYFP |
| N (mice) | 3 | 6 |
| # UBE3A-YFP+ cells counted | 1029 | 343 |
| UBE3A-YFP+ / NeuN+ cells | 99.25±0.43 | 93.25±1.30 |

METHODS AND COMPOSITIONS FOR UNSILENCING IMPRINTED GENES

STATEMENT OF PRIORITY

This application is a 35 U.S.C. §371 national phase application of International Application Serial No. PCT/US2011/059893, filed Nov. 9, 2011, which claims the benefit, under 35 U.S.C. §119(e), of U.S. Provisional Patent Application No. 61/412,638, filed Nov. 11, 2010, the entire contents of each of which are incorporated by reference herein.

STATEMENT OF GOVERNMENT SUPPORT

Aspects of this invention were funded under Contract No. W81XWH-10-1-0710 from the Department of Defense. The U.S. Government has certain rights in this invention.

BACKGROUND OF THE INVENTION

Angelman syndrome is an autism spectrum disorder for which no effective treatment currently exists. Individuals with Angelman syndrome exhibit outwardly normal development during the first year of life, but then develop severe intellectual disabilities, seizures, EEG abnormalities, gait disturbances, disrupted sleep patterns, and profound language impairments (Zori et al., 1992; Lossie et al., 2001; Clayton-Smith and Laan, 2003; Williams, 2005; Dan, 2008; Pelc et al., 2008; Dan, 2009). These deficits are caused by maternal deletions or mutations of a single gene, the E3 ubiquitin ligase Ube3a, and can be modeled in Ube3a-deficient mice. Because the paternal allele of Ube3a is silenced in most neurons through epigenetic imprinting, lost function of the maternal allele eliminates Ube3a protein expression in neurons (FIG. 1). With a prevalence of 1:15,000 (Steffenburg et al., 1996; Dan, 2008) and an average cost of care of >$150,000/year per individual across a full lifespan (Angelman Syndrome Foundation), the health care costs of Angelman syndrome are immense, quite aside from the human cost.

Genetic engineering approaches were used to rescue the neurological deficits in Angelman syndrome model mice (van Woerden et al., 2007), but this approach relies on knocking out genes, making it impractical in humans. A pharmacological approach offers a more viable alternative. Only one clinical trial, which tested the effects of the methyl donors betaine and folic acid, has been performed in humans (Arn et al., 1998; Bacino et al., 2003), and it has not proved successful to date.

The present invention provides methods and compositions for unsilencing imprinted genes (e.g., the paternal allele of Ube3a silenced through epigenetic imprinting), thereby providing methods of treatment of genomic imprinting disorders, such as Angelman syndrome.

SUMMARY OF THE INVENTION

In one aspect, the present invention provides a method of inducing expression of Ube3a in a cell, comprising contacting the cell with an effective amount of a topoisomerase inhibitor, thereby inducing expression of Ube3a in the cell.

An additional aspect of the present invention is a method of treating a genomic imprinting disorder in a subject, comprising administering to the subject an effective amount of a topoisomerase inhibitor, thereby treating the genomic imprinting disorder in the subject.

Further aspects of this invention include a method of treating a disorder associated with an epigenetic modification in a subject, comprising administering to the subject an effective amount of a topoisomerase inhibitor, thereby treating the disorder associated with the epigenetic modification in the subject.

DESCRIPTION OF THE FIGURES

FIGS. 13A-G. A small-molecule screen identifies a topoisomerase inhibitor that unsilences the paternal allele of Ube3a in neurons. (A) High-content screen flowchart. E15.5 cortical neurons with a paternally inherited Ube3a-YFP allele were cultured in 384-well plates and treated with small molecules from DIV7-DIV10. Active compounds that unsilence the paternal Ube3a-YFP allele were detected with antibody-enhanced fluorescence and high-content imaging. (B) High-content imaging of DIV7 neurons that inherited Ube3a-YFP maternally ($m^{YFP}/p^+$) or paternally ($m^+/p^{YFP}$). Nuclei were stained with DAPI. Scale bar=50 µm. (C) Mean±s.e.m. levels of UBE3A-YFP fluorescence in neurons cultured from maternal Ube3a-YFP($m^{YFP}/p^+$) or wild-type ($m^+/p^+$) mice, normalized to levels in age-matched neurons cultured from paternal Ube3a-YFP mice ($m^+/p^{YFP}$). Two-way ANOVA, $F_{(1,58)}$=1492.52, P<0.001 for genotype; $F_{(9,58)}$=97.72, P<0.001 for duration; $F_{(9,58)}$=97.72, P<0.001 for genotype-duration interactions; Bonferroni post hoc test after significant main effects examined comparisons between maternal and paternal Ube3a-YFP mice from DIV4 to DIV10, *P<0.001; n=2-6 culture wells/day. (D) Pie chart depicting categories of the 2,306 screened compounds and graph summarizing presumptive UBE3A-YFP in arbitrary fluorescence units (A.F.U.) after small molecule treatments. Small molecules that were subsequently found to be auto-fluorescent (FIG. 17) are depicted in gray. The initial screen identified one active compound, irinotecan. (E) High magnification view of wells treated with vehicle (0.2% DMSO) or 10 µM irinotecan for 72 hr. Neuron density and health is similar in vehicle- and irinotecan-treated cells as evidenced by counterstaining with the nuclear marker DAPI. Scale bar=100 µm. (F) Western blot showing UBE3A-YFP protein levels were increased with irinotecan (10 µM for 72 h). *P<0.05; two-tailed t-test, n=3/group. (G) Western blot to detect UBE3A protein in cultures taken from wild-type ($m^+/p^+$) or maternally Ube3a-deficient ($m^-/p^+$) mice treated with vehicle or irinotecan (10 µM for 72 h). One-way ANOVA, $F_{(2,20)}$=30.47, P<0.001; Bonferroni post hoc test after significant main effect, *P<0.001; n=7-8/group. All data are presented as means±s.e.m.

FIGS. 19A-B. Dose response curves and structures for the topoisomerase type I inhibitor camptothecin and two structurally-related analogs. (A) Dose response curve for camptothecin and lactam E ring camptothecin (inactive). Chemical modification of the camptothecin lactone E ring to a lactam E ring (circles) results in a topoisomerase inactive compound. (B) Dose response curve and chemical structure for 7-ethyl-camptothecin. Results are the mean±s.e.m. from three independent experiments.

FIGS. 20A-B. Dose response curves and structures of the topoisomerase type I inhibitors 10-hydroxy-camptothecin, 7-ethyl-10-hydroxy-CPT, and irinotecan. (A) Dose response curve and chemical structure for 10-hydroxy-camptothecin (CPT). (B) Dose response curve and chemical structure for 7-ethyl-10-hydroxy-CPT (SN38) and irinotecan. Structure activity relationship is apparent between irinotecan and its metabolite SN38. Results are the mean±s.e.m. from three independent experiments.

FIGS. 21A-B. Dose response curves and structures of the topoisomerase type I inhibitors rubitecan, belotecan, and silatecan. (A) Dose response curve and chemical structure for rubitecan. (B) Dose response curve and chemical structure for belotecan and silatecan. Results are the mean±s.e.m. from three independent experiments.

FIGS. 22A-C. Dose response curves and structures of three indenoisoquinoline (non-camptothecin)-based topoisomerase type I inhibitors. Dose response curves and chemical structure for (A) NSC706744, (B) NSC725776 and (C) NSC724998. Results are the mean±s.e.m. from three independent experiments.

FIG. 23. Dose response curve and structure of the topoisomerase type II inhibitor etoposide. Results are the mean±s.e.m. from one experiment performed in quadruplicate.

FIGS. 24A-B. Dose response curves and structures for the topoisomerase type II inhibitors ICRF-193 and ICRF-187. Dose response curves and chemical structures for (A) ICRF-193 and (B) ICRF-187 (dexrazoxane). Results are the mean±s.e.m. from two independent experiments, each performed in quadruplicate.

FIG. 25. Dose response curve and structure for the topoisomerase type II inhibitor amsacrine. Results are the mean±s.e.m. from three independent experiments.

Paternal Ube3a-YFP ($m^+/p^{YFP}$) neurons were treated with 300 nM topotecan for the times indicated followed by drug removal and replacement with conditioned media; cells were fixed 72 h after initial drug exposure. (B) UBE3A-YFP fluorescence was determined from paternal Ube3a-YFP neurons treated with topotecan or vehicle for various durations during a 72 h period. Notice a significant difference of UBE3A-YFP intensity between 0 and 4, 8, 16, 24, 48 and 72 hrs. One Way-ANOVA, $F_{(7, 48)}=147.449$, $P<0.001$; Bonferroni post hoc test after significant main effect indicates comparisons to 0 hr, *$P<0.001$, n=5-8/time point. Results are the means±s.e.m, from four wells of cells, and similar results were obtained in three independent experiments.

Figure 27:
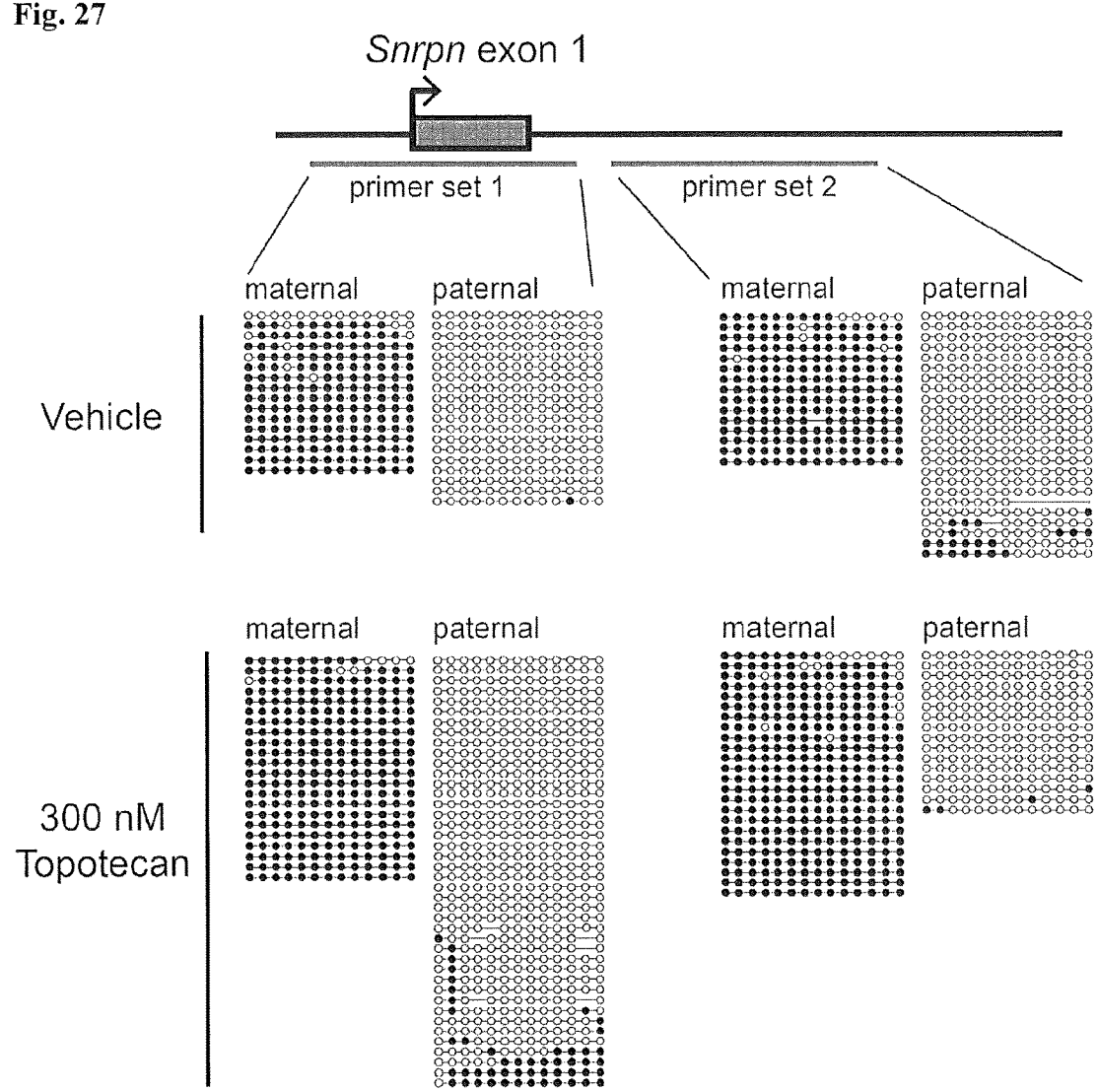

FIG. 27. Bisulfite sequencing of the Ube3a-ATS/Snrpn promoter region in cortical neurons following treatment with vehicle or topotecan. Cortical neurons from hybrid CAST/EiJ×C57BL/6 embryos were treated with vehicle (0.1% DMSO) or 300 nM topotecan. Genomic DNA was isolated after 72 h of drug treatment and bisulfite conversion was performed. Two primer sets were used to amplify bisulfite treated DNA isolated from cortical cultures: one flanking the first exon of Snrpn and encompassing 13 CpGs, the second to a sequence in the first intron of Snrpn and encompassing 14 CpGs (13 for paternal clones, as one CpG is polymorphic). Clones were identified as originating from the maternal or paternal chromosome on the basis of polymorphisms between the CAST/EiJ and C57BL/6 strains. Filled circles represent methylated cytosine residues, open circles represent unmethylated residues. Clones were derived from three independent cortical cultures. Efficiency of bisulfite conversion for all samples was greater than 97%.

Figure 28A:
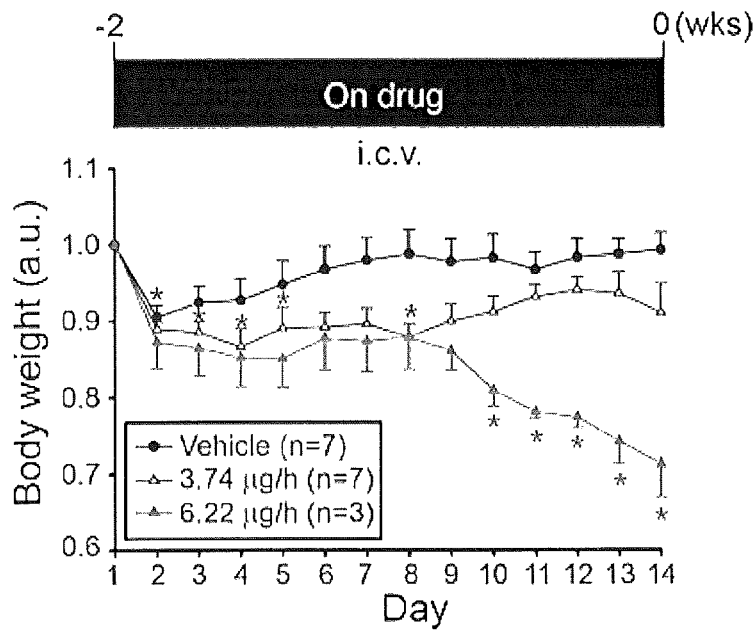
Figure 28B:
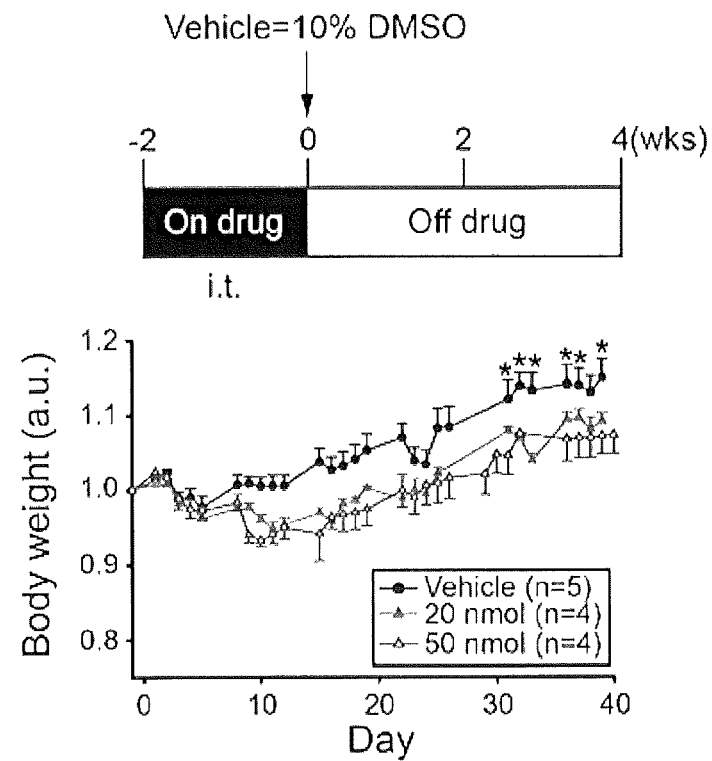
Figure 28C:
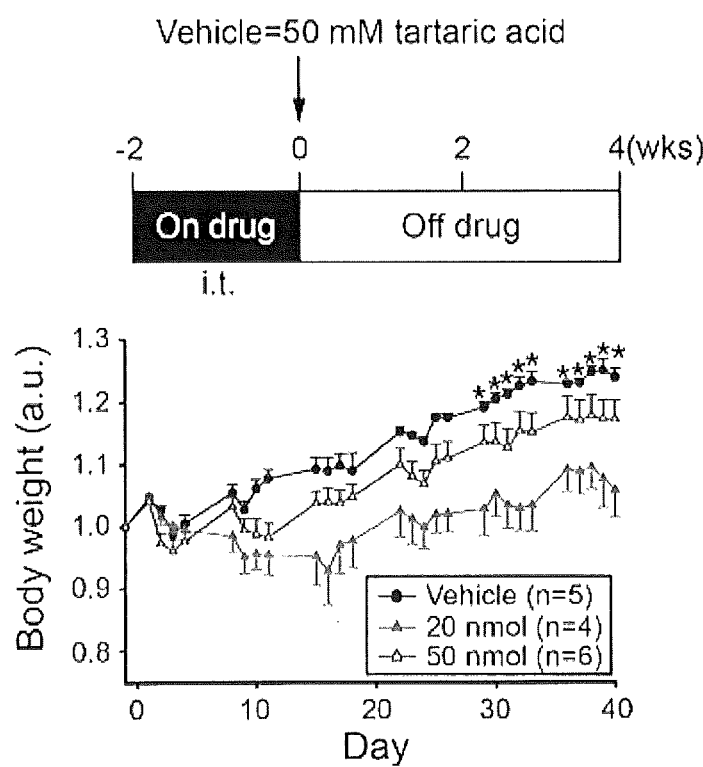

FIGS. 28A-C. Effects of topotecan on mouse body weight. (A) Normalized body weight in mice given vehicle (50 mM tartaric acid in saline) or topotecan (3.74 or 6.22 μg/h) administered for two weeks by intracerebroventricular (i.c.v.) infusion using mini-osmotic pumps. Kruskal-Wallis one-way ANOVA was tested for vehicle; One-way ANOVA, $F_{(13,84)}=2.532$; $P<0.01$ Bonferroni post hoc test after significant main effect, *$P<0.05$ for 3.74 μg/h; One-way ANOVA, $F_{(13,28)}=4.9$, $P<0.001$, Bonferroni post hoc test after significant main effect, *$P<0.05$ for 6.22 μg/h. (B,C) Normalized body weights in mice given vehicle (10% DMSO or 50 mM tartaric acid in 0.9% saline) or topotecan (dose indicated in figure) by daily intrathecal injection for 10 of 14 days followed by up to four weeks off-drug. For all panels, topotecan or vehicle-treated groups were compared to their first day (A) or the average of two days before injection (B,C). For data in panels (B) and (C), Kruskal-Wallis one-way ANOVA with Dunn's post hoc test compared body weights after the first day of drug or vehicle injections to the two day average before injections began (represented at Day −1), *$P<0.05$. The body weight of mice was measured daily throughout a two (A) or six (B,C) week period.

Figure 29:
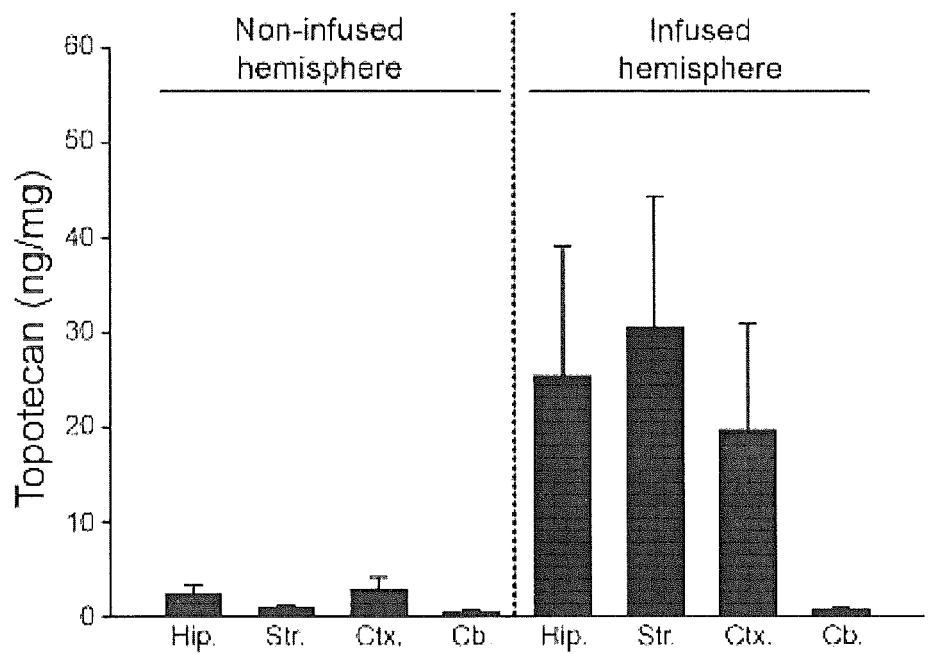

FIG. 29. Pharmacokinetics in brain. Topotecan levels in the hippocampus (Hip.), striatum (Str.), cerebral cortex (Ctx.), and cerebellum (Cb.) of the infused and non-infused hemisphere immediately after cessation of intracerebroventricular drug delivery (3.74 μg/hr for one week). Topotecan was delivered effectively to the hippocampus, striatum, and cerebral cortex of the infused hemisphere, but not the cerebellum. n=4/group. All data are presented as means±s.e.m.

Figure 30:
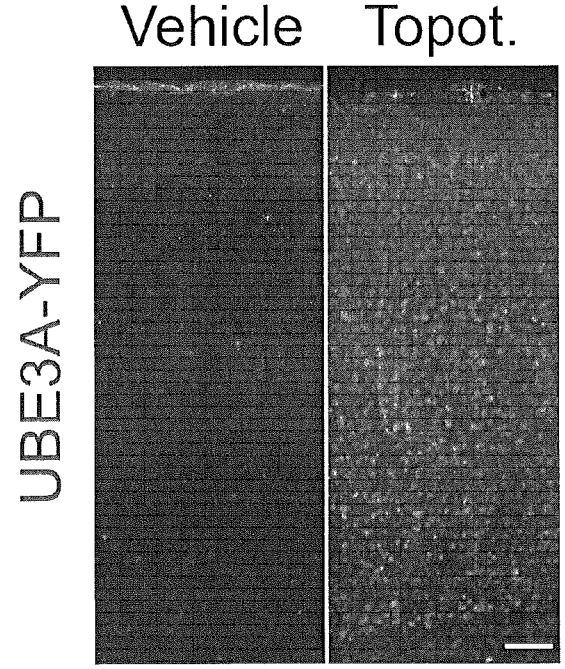

FIG. 30. Topotecan unsilences the paternal Ube3a-YFP allele in cerebral cortex. Paternal Ube3a-YFP mice were administered vehicle (50 mM tartaric acid) or topotecan (3.74 μg/h) by intracerebroventricular (i.c.v) infusion using mini-osmotic pump for two weeks. In two of five mice, the cerebral cortex near the infused ventricle exhibited robust unsilencing of paternal Ube3a-YFP following topotecan treatment. Scale bar=100 μm.

Figure 31:
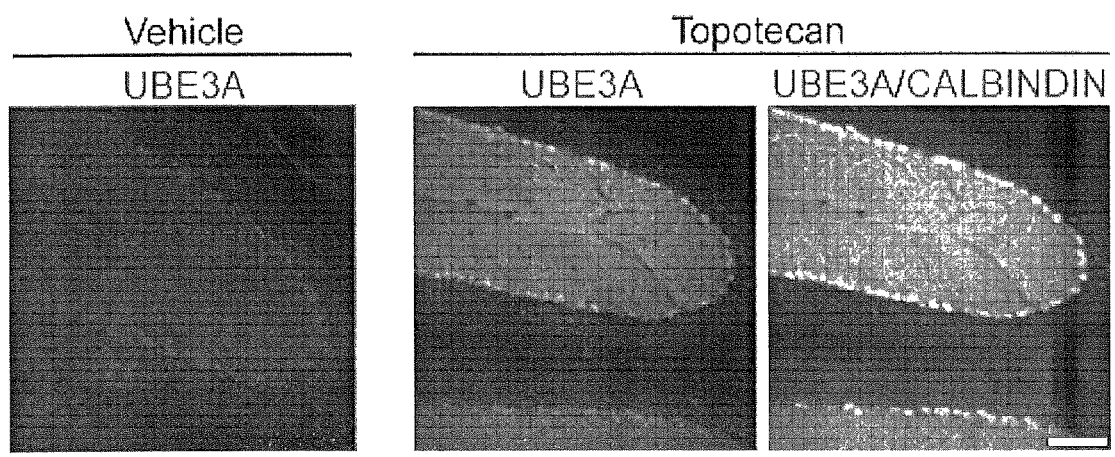

FIG. 31. Higher concentrations of topotecan delivered i.c.v. unsilence the paternal Ube3a-YFP allele in cerebellar Purkinje cells. Ube3a-YFP$^{m+/pYFP}$ mice were administered vehicle (50 mM tartaric acid) or topotecan (21.6 μg/h) by intracerebroventricular (i.c.v) infusion using mini-osmotic pump for five days. Calbindin-positive Purkinje cells expressed paternal Ube3a-YFP following topotecan. Scale bar=100 μm.

Figure 32A:
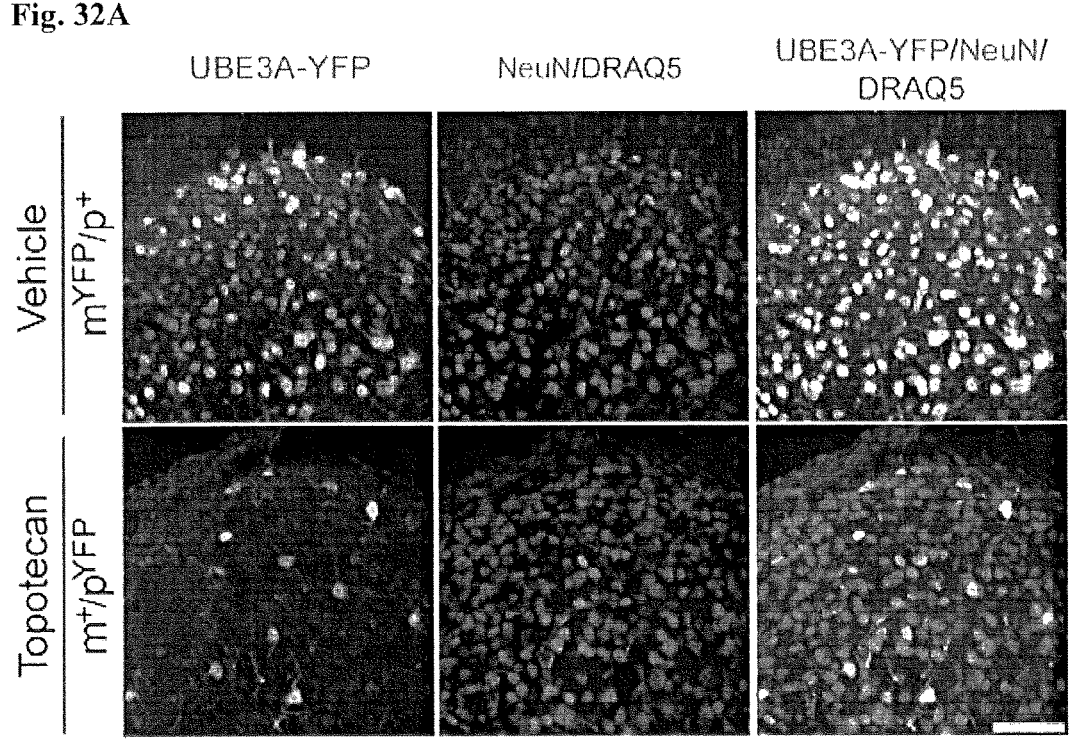
Figures 32B, 32C:
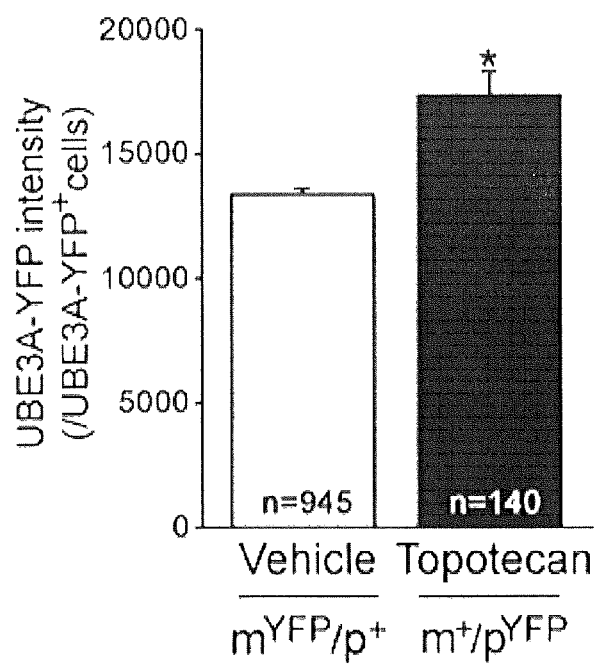

FIGS. 32A-C. Topotecan unsilences the paternal Ube3a-YFP allele in neurons. (A) Expression of UBE3A-YFP, the neuronal marker NeuN, and the nuclear marker DRAQ5 following intrathecal injection of vehicle or topotecan (50 nmol/day for 10 of 14 days) in mice expressing Ube3a-YFP from the maternal or paternal chromosome. Scale bar=50 (B) Percentage of UBE3A-YFP$^+$ cells that were NeuN$^+$. These data demonstrate that topotecan predominately unsilences paternal Ube3a-YFP in neurons (93.25%), similar to the predominant expression of maternal Ube3a-YFP in neurons (99.25%). (C) Average pixel intensity of maternal UBE3A-YFP$^+$ cells compared to paternal UBE3A-YFP$^+$ cells after topotecan treatment. *$P<0.001$, Mann-Whitney rank sum test.

DETAILED DESCRIPTION OF THE INVENTION

Particular aspects of this invention are explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure that do not depart from the instant invention.

Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, nucleotide sequences, amino acid sequences and other references mentioned herein are incorporated by reference in their entirety.

The present invention is based on the development of screening assays to identify substances (e.g., small molecules) that unsilence imprinted genes. This invention is further based on the unexpected discovery that topoisomerase inhibitors can be used to treat genomic imprinting disorders, such as Angelman syndrome.

Thus, in one embodiment, the present invention provides a method of inducing expression of Ube3a in a cell, comprising contacting the cell with an effective amount of a topoisomerase inhibitor, thereby inducing expression of Ube3a in the cell. In some embodiments, the cell can be a central neuron, a peripheral neuron, a neuron differentiated from stem cells, a glial cell, an astrocyte, an oligodendrocyte, a microglial cell, and any combination thereof. In some embodiments, the cell can be in a subject (e.g., a human subject) and the Ube3a that is induced is the paternal allele of Ube3a. Such a subject can be a subject in which function of the maternal allele of Ube3a has been lost and Ube3a protein production is defective in the subject.

In further embodiments of the present invention, a method is provided of treating a genomic imprinting disorder in a subject, comprising administering to the subject an effective amount of a topoisomerase inhibitor, thereby treating the genomic imprinting disorder in the subject. In particular embodiments, the genomic imprinting disorder is Angelman syndrome. In some embodiments, the genomic imprinting disorder is Prader Willi syndrome, Beckwith-Wiedemann syndrome, Russell-Silver syndrome, Albright hereditary osteodystrophy, or Turner's syndrome and any combination thereof.

The present invention further provides a method of treating a disorder associated with an epigenetic modification in a subject, comprising administering to the subject an effective amount of a topoisomerase inhibitor, thereby treating the disorder associated with the epigenetic modification in the subject. In some embodiments, the disorder associated with an epigenetic modification can be but is not limited to an autism spectrum disorder, depression, schizophrenia, Rett syndrome, Fragile X syndrome, and any combination thereof.

In some embodiments, the topoisomerase inhibitor of this invention can be a topoisomerase I inhibitor, which can be, in some embodiments, a camptothecin derivative. A camptothecin derivative of this invention can be, but is not limited to Belotecan (CKD602), Camptothecin, 7-Ethyl-10-Hydroxy-CPT, 10-Hydroxy-CPT, Rubitecan (9-Nitro-CPT), 7-Ethyl-CPT, Topotecan, Irinotecan, Silatecan (DB67) and any combination thereof.

In some embodiments of this invention, the topoisomerase I inhibitor can be an indenoisoquinoline derivative, which can be but is not limited to NSC706744, NSC725776, NSC724998 and any combination thereof.

In further embodiments of this invention, the topoisomerase inhibitor is a topoisomerase II inhibitor, which in some embodiments can be an acridine derivative, which can be but is not limited to Amsacrine, in some embodiments the topoisomerase II inhibitor can be a podophyllotoxin derivative, which can be but is not limited to etoposide, and in some embodiments the topoisomerase II inhibitor can be a bisdioxopiperazine derivative, which can be but is not limited to ICRF-193, dexrazoxane (ICRF-187) and any combination thereof.

In yet further embodiments of this invention, the topoisomerase inhibitor can be Resveratrol (PMID: 20304553; PMID: 15796584)[41], Epigallocatechin gallate (PMID: 18293940; PMID: 11594758; PMID: 11558576; PMID: 1313232)[42,43], Genistein (PMID: 17458941)[44], Daidzein (PMID: 17458941)[45]. Quercetin (PMID: 1313232; PMID: 16950806; PMID: 15312049), natural flavones related to quercetin that inhibit topoisomerase, such as acacetin, apigenin, kaempferol and morin (PMID: 8567688)[46-48], Luteolin (PMID: 12027807; PMID: 16950806; PMID: 15312049)[46]; Myricetin (PMID: 20025993)[49] and any combination thereof.

In certain embodiments of the present invention, the topoisomerase inhibitor has an efficiency, $E_{max}$, of at least about 1.5, 1.6, 1.7, 1.8, 1.9, 2.0, 2.1, 2.2, 2.3, 2.4, or 2.5 fold over control.

In certain embodiments, the topoisomerase inhibitor can be an interfering RNA (RNAi) molecule that targets topoisomerase I, topoisomerase II or both. Nonlimiting examples of RNAi molecules include small interfering RNA (siRNA), short hairpin RNA (shRNA), microRNA (miRNA), antisense nucleic acid molecules, and the like as are well known in the art. Nonlimiting examples of siRNAs and shRNAs of this invention are provided in Table 2. In some embodiments, a zinc finger nuclease, an antibody and/or a ribozyme can be employed to inhibit topoisomerase activity in the methods of this invention.

The present invention additionally provides screening methods to identify a substance that can unsilence Ube3a expression and/or increase Ube3a expression. Thus, further provided herein is a screening method to identify a substance that can increase Ube3a expression, comprising culturing cells for screening of small molecules, drugs, drug-like compounds, siRNA constructs, and/or shRNA constructs. In some embodiments, cells are from neurotypical animals, in some instances cells are from mice lacking Ube3a on the maternal allele ($Ube3a^{m-/p+}$) or the paternal allele ($Ube3a^{m-/p-}$), and in some instances cells are from mice expressing Ube3a-YFP knocked into the maternal Ube3a allele, paternal Ube3a allele, or both. These cultured cells are then contacted with a test substance, which can be but is not limited to a small molecule, drug, drug-like compound, siRNA construct, shRNA construct, and/or vehicle control for varying durations as would be known in the art, and then an assessment is made of a test substance-induced increase in Ube3a expression over vehicle control levels through, e.g., direct or antibody-enhanced fluorescence of Ube3a.

Additional approaches to screen for a test substance-induced increase in Ube3a include, e.g., quantitative polymerase chain reaction (PCR) and/or other analogous approaches to identify a test substance-induced increase in Ube3a mRNA expression, and/or immunoblotting or other analogous approaches as would be well known in the art to identify a test substance-induced increase in Ube3a protein expression. Flow cytometry may be used to identify a test substance that increases Ube3a expression in cultured cells. In vivo delivery of a test substance can also be used to determine the ability of a test substance to increase Ube3a expression; delivery of a test substance can be oral, rectal, transmucosal, topical, intranasal, inhalation (e.g., via an aerosol), buccal (e.g., sublingual), vaginal, intrathecal, intracerebroventricular, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces), and/or transdermal administration, and the like, as well as via direct tissue or organ injection (e.g., to liver, skeletal muscle, cardiac muscle, diaphragm muscle and/or brain).

A test substance identified according to these screening methods that can unsilence Ube3a expression and/or increase Ube3a expression can be employed in the methods of this invention of inducing expression of Ube3a in a cell and of treating one or more of the various disorders described herein, such as, for example, Angelman syndrome.

Further provides herein is a screening method to identify a substance that can decrease Ube3a expression, comprising culturing cells for screening of small molecules, drugs, drug-like compounds, siRNA constructs, and/or shRNA constructs. In some embodiments, cells can be from neurotypical animals, in some embodiments, cells can be from mice lacking Ube3a on the maternal allele (Ube3a$^{m-/p+}$) or the paternal allele (Ube3a$^{m+/p-}$), and in some embodiments, cells can be from mice expressing Ube3a-YFP knocked into the maternal Ube3a allele, paternal Ube3a allele, or both. These cultured cells are then contacted with a test substance, which can be but is not limited to a small molecule, drug, drug-like compound, siRNA construct, shRNA construct, and/or vehicle control for varying durations as would be known in the art, and then an assessment is made of a test substance-induced decrease in Ube3a expression compared to a vehicle control level through, e.g., direct or antibody-enhanced fluorescence of Ube3a.

Additional approaches to screen for a test substance-induced decrease in Ube3a Include quantitative PCR and/or other analogous approaches to identify a test substance-induced decrease in Ube3a mRNA expression, and/or immunoblotting and/or other analogous approaches to identify a test substance-induced decrease in Ube3a protein expression. Flow cytometry may be used to identify a compound that can decrease Ube3a expression in cultured cells. In vivo delivery of a test substance can also be used to determine the ability of a test substance to decrease Ube3a expression; delivery of a test substance can be oral, rectal, transmucosal, topical, intranasal, inhalation (e.g., via an aerosol), buccal (e.g., sublingual), vaginal, intrathecal, intracerebroventricular, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces), and/or transdermal administration, and the like, as well as via direct tissue or organ injection (e.g., to liver, skeletal muscle, cardiac muscle, diaphragm muscle or brain).

A substance identified according to these screening methods that can decrease Ube3a expression can be used, for example, in a method of treating disorders associated with increased Ube3a expression, such as autism spectrum disorders. These forms of autism include isodicentric chromosome 15, also known as idic (15), and duplications of chromosome 15q11-q13 (dup15q). Potential 'hits' identified by this screening method would have to go through additional control experiments to verify that they are not acting by increasing neuronal death or through generalized inhibition of protein synthesis. Identified compounds that act to decrease Ube3a levels, without causing cell death or a generalized decrease in protein synthesis, can be used as therapeutics for autism spectrum disorders associated with increased Ube3a expression or gene dosage.

The present invention also provides various compositions. In some embodiments these compositions can be employed, e.g., in the methods described herein. Thus, the present invention provides a composition comprising, consisting essentially of and/or consisting of a topoisomerase inhibitor and/or other compound of this invention, which can be, for example, in a pharmaceutically acceptable carrier. "Pharmaceutically acceptable," as used herein, means a material that is not biologically or otherwise undesirable, i.e., the material may be administered to a subject along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution, as well as other carriers suitable for injection into and/or delivery to a subject of this invention, particularly a human subject, as would be well known in the art.

It is further contemplated that the present invention provides a kit comprising, consisting essentially of and/or consisting of one or more compositions of this invention. It would be well understood by one of ordinary skill in the art that the kit of this invention can comprise one or more containers and/or receptacles to hold the reagents (e.g., topoisomerase inhibitors, etc.) of the kit, along with appropriate buffers and/or diluents and/or other solutions and directions for using the kit, as would be well known in the art. The compositions and kits of the present invention can also include other medicinal agents, pharmaceutical agents, carriers and diluents, etc., in any combination. Actual methods of preparing such dosage forms are known, or will be apparent, to those skilled in this art.

In the kits of this invention, the compositions can be presented in unit\dose or multi-dose containers, for example, in sealed ampules and vials, and can be stored in a freeze-dried (lyophilized) condition requiring only the addition of a sterile liquid carrier, for example, saline or water-for-injection prior to use.

Further Definitions

The following terms are used in the description herein and the appended claims:

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, a "topoisomerase" or "DNA topoisomerase" is an enzyme that plays a role in the replication, repair, genetic recombination and transcription of DNA. The topoisomerases constitute a group of enzymes that catalyze the conversion of DNA from one topological form to another by introducing transient breaks in one or both strands of a DNA duplex. Topological isomers are molecules that differ only in their state of supercoiling. Type I topoisomerase cuts one strand of DNA and relaxes negatively supercoiled DNA, but does not act on positively supercoiled DNA. Type II topoisomerase cuts both strands of DNA and increases the degree of negative supercoiling in DNA. These terms include any analogues and derivatives of topoisomerases I and II, as are well known in the art.

A "topoisomerase inhibitor" or "DNA topoisomerase inhibitor" is a compound that interferes with the activity of a topoisomerase. One example of a topoisomerase inhibitor is camptothecin, a natural compound that interferes with the activity of topoisomerase I, an enzyme involved in DNA replication and RNA transcription. Camptothecin and the camptothecin analogues topotecan and irinotecan are approved for clinical use. Other camptothecin derivatives/analogues include, but are not limited to, belotecan, rubetecan, and silatecan. Other nonlimiting examples of a topoisomerase inhibitor include indenoisoquinoline derivatives, acridine derivatives, bisdioxopiperazine derivatives, etoposide, mitoxantrone, lamellarin D, doxorubicin, teniposide, ICRF-193, as well as any other topoisomerase inhibitor now known or later identified.

As used herein, a "genomic imprinting disorder" means any disorder caused by the mutation or deletion of a gene that is genetically imprinted, any disorder caused by alterations of the normal imprinting pattern, and/or any disorder caused by changes in gene dosage of an imprinted gene. Nonlimiting examples of a genomic imprinting disorder of this invention include Angelman syndrome, Prader Willi syndrome, Beckwith-Wiedemann syndrome, Russell-Silver syndrome, Albright hereditary osteodystrophy and Turner's syndrome. Any of these disorders can be treated according to the methods provided herein.

Also as used herein, a "disorder associated with an epigenetic modification" means a disorder associated with changes of normal chromatin pattern, including but not limited to histone modifications and DNA methylation. Nonlimiting examples of a disorder associated with an epigenetic modification include autism spectrum disorders, cancer, depression, schizophrenia, Rett syndrome and Fragile X syndrome.

Symptomology of a genomic imprinting disorder and/or a disorder associated with epigenetic modification can include, but is not limited to, severe intellectual disabilities, seizures, EEG abnormalities, gait disturbances, disrupted sleep patterns, somatosensory deficits, profound language impairments, abnormal pain sensitivity, and balance abnormalities, which can be manifested singly and/or in any combination over time. This it is further contemplated that the present invention provides methods of treating one or more of these symptoms in any combination in a subject, comprising administering to the subject an effective amount of a topoisomerase inhibitor.

A subject of this invention can be any animal in which genomic imprinting disorders occur and in particular embodiments, is a human subject, although nonhuman subjects [e.g., animal models of genomic imprinting disorders such as rodents (mice, rats, hamsters, guinea pigs, etc.), pigs, non-human primates] are included within the present invention.

A subject of this invention can be "in need of" the methods of the present invention, e.g., because the subject has, or is believed at risk for, a genomic imprinting disorder including those described herein, such as Angelman syndrome and/or is a subject that would benefit from the methods of this invention. For example, a subject in need of the methods of this invention can be, but is not limited to, a subject diagnosed with, having or suspected to have, or at risk of having or developing a genomic imprinting disorder (e.g., Angelman syndrome).

The term "therapeutically effective amount" or "effective amount," as used herein, refers to that amount of a topoisomerase inhibitor and/or other compound and/or composition of this invention that imparts a modulating effect, which, for example, can be a beneficial effect, to a subject afflicted with a condition (e.g., a disorder, disease, syndrome, illness, injury, traumatic and/or surgical wound), including improvement in the condition of the subject (e.g., in one or more symptoms), delay or reduction in the progression of the condition, delay of the onset of the condition, and/or change in clinical parameters, status or classification of a disease or illness, etc., as would be well known in the art.

For example, a therapeutically effective amount or effective amount can refer to the amount of a topoisomerase inhibitor and/or other compound and/or composition of this invention that improves a condition in a subject by at least about 5%, e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

"Treat" or "treating" or "treatment" refers to any type of action that imparts a modulating effect, which, for example, can be a beneficial effect, to a subject afflicted with a condition (e.g., disorder, disease, syndrome, illness, traumatic or surgical wound, injury, etc.), including improvement in the condition of the subject (e.g., in one or more symptoms), delay or reduction in the progression of the condition, delay of the onset of the condition, and/or change in clinical parameters, disease or illness, etc., as would be well known in the art.

By the terms "treat," "treating" or "treatment of" (or grammatically equivalent terms), it is also meant that the severity of the subject's condition is reduced or at least partially improved or ameliorated and/or that some alleviation, mitigation or decrease in at least one clinical symptom is achieved and/or there is a delay in the progression of the condition and/or delay of the onset of a disease or disorder.

By "prevent," "preventing" or "prevention" is meant to avoid or eliminate the development and/or manifestation of a pathological state and/or disease condition or disorder or status in a subject.

Exemplary modes of administration of a topoisomerase inhibitor and/or other compound and/or composition of this invention can include oral, rectal, transmucosal, topical, intranasal, inhalation (e.g., via an aerosol), buccal (e.g., sublingual), vaginal, intrathecal, intracerebroventricular, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration, and the like, as well as direct tissue or organ injection (e.g., to liver, skeletal muscle, cardiac muscle, diaphragm muscle or brain). The most suitable route in any given case will depend on the nature and severity of the condition being treated and on the nature of the particular therapeutic compound and/or composition that is being used.

For injection, the carrier will typically be a liquid. For other methods of administration, the carrier may be either solid or liquid. For inhalation administration, the carrier will be respirable, and will typically be in solid or liquid particulate form.

Dosages of the topoisomerase inhibitor and/or other compound(s) of this invention to be administered to a subject will depend upon the mode of administration, the disease or condition to be treated, the individual subject's condition, the particular therapeutic compound and/or composition, and any other agents being administered to the subject and can be determined in a routine manner according to methods well known in the art. An exemplary dosage range for a human subject is from about 0.001 mg/kg/day to about 500 mg/kg/day. In some embodiments, the dosage range can be from about 0.01 mg/kg/day to about 100 mg/kg/day and in some embodiments, the dosage range can be from about 0.1 mg/kg/day to about 10 mg/kg/day.

A nonlimiting example of a method of treating Angelman syndrome in a human subject comprises administering to the subject (e.g., in utero, perinatally, postnatally, during infancy, during childhood, during adolescence, during teen years, during early adulthood, during middle adulthood, during late adulthood and any combination thereof), a dose of a topoisomerase inhibitor of this invention in the range of about 0.01 nmole to about 100 mmole by an intrathecal and/or intracerebroventricular route. In an embodiment in which the topoisomerase inhibitor is an interfering RNA (RNAi) molecule (e.g., siRNA; shRNA, etc.), the route of administration could be intrathecal and/or intracerebroventricular and the dose could be in the range of about 0.01 mg/kg to about 100 mg/kg and in some embodiments could be about 0.1 mg/kg to about 10 mg/kg.

In some embodiments, a single administration of a therapeutic compound and/or composition of this invention may be effective. In other embodiments, more than one administration (e.g., two, three, four or more administrations) of the therapeutic compound and/or composition may be employed to achieve the desired result over a period of various intervals, e.g., hourly, daily, weekly, monthly, yearly, etc.

The present invention will now be described with reference to the following examples. It should be appreciated that these examples are for the purposes of illustrating aspects of the present invention, and do not limit the scope of the invention as defined by the claims provided herein.

EXAMPLES

Example 1. Small Molecule Screening

Figure 8:
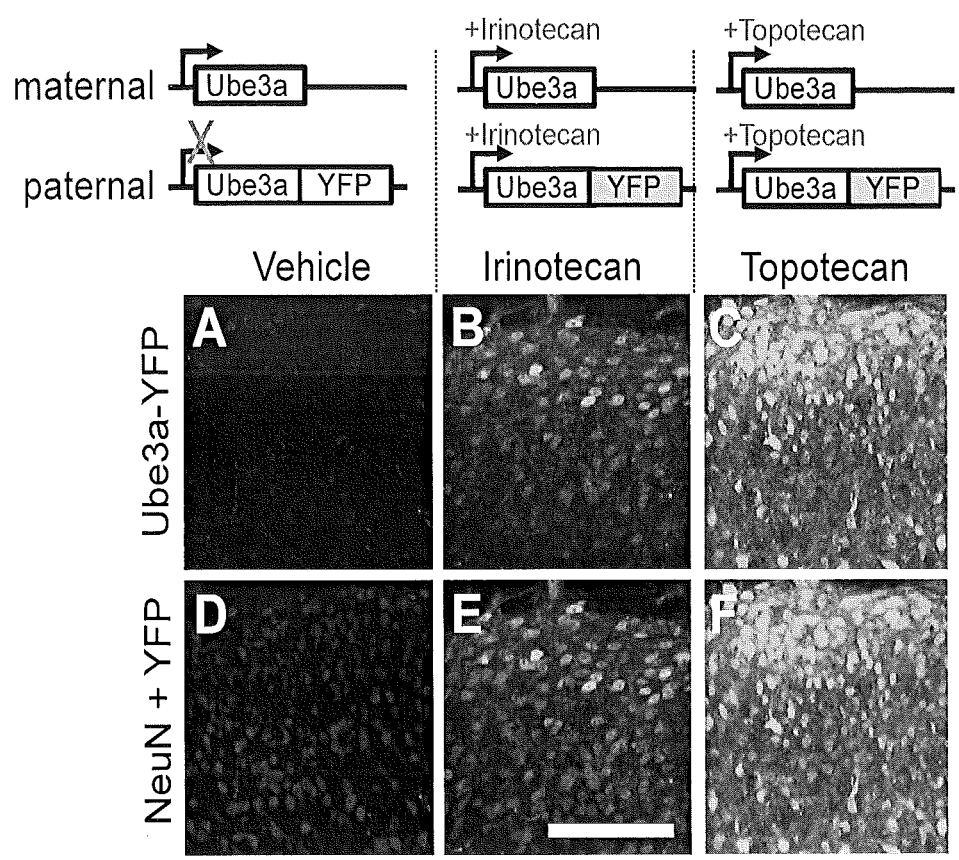
FIGS. 8A-F. Irinotecan and topotecan can unsilence paternal Ube3a in vivo. (A) Paternal Ube3a-YFP is silenced (not expressed) in spinal neurons. Intrathecal injection of (B) irinotecan or (C) topotecan into live mice unsilenced the paternal Ube3a-YFP allele in spinal neurons. These results have been reproduced in n>4 mice. (D-F) Neuron health is similar in vehicle- and drug-treated mice as evidenced by counterstaining with the pan-neuronal marker NeuN. Scale bar=100 µm.
Figure 9:
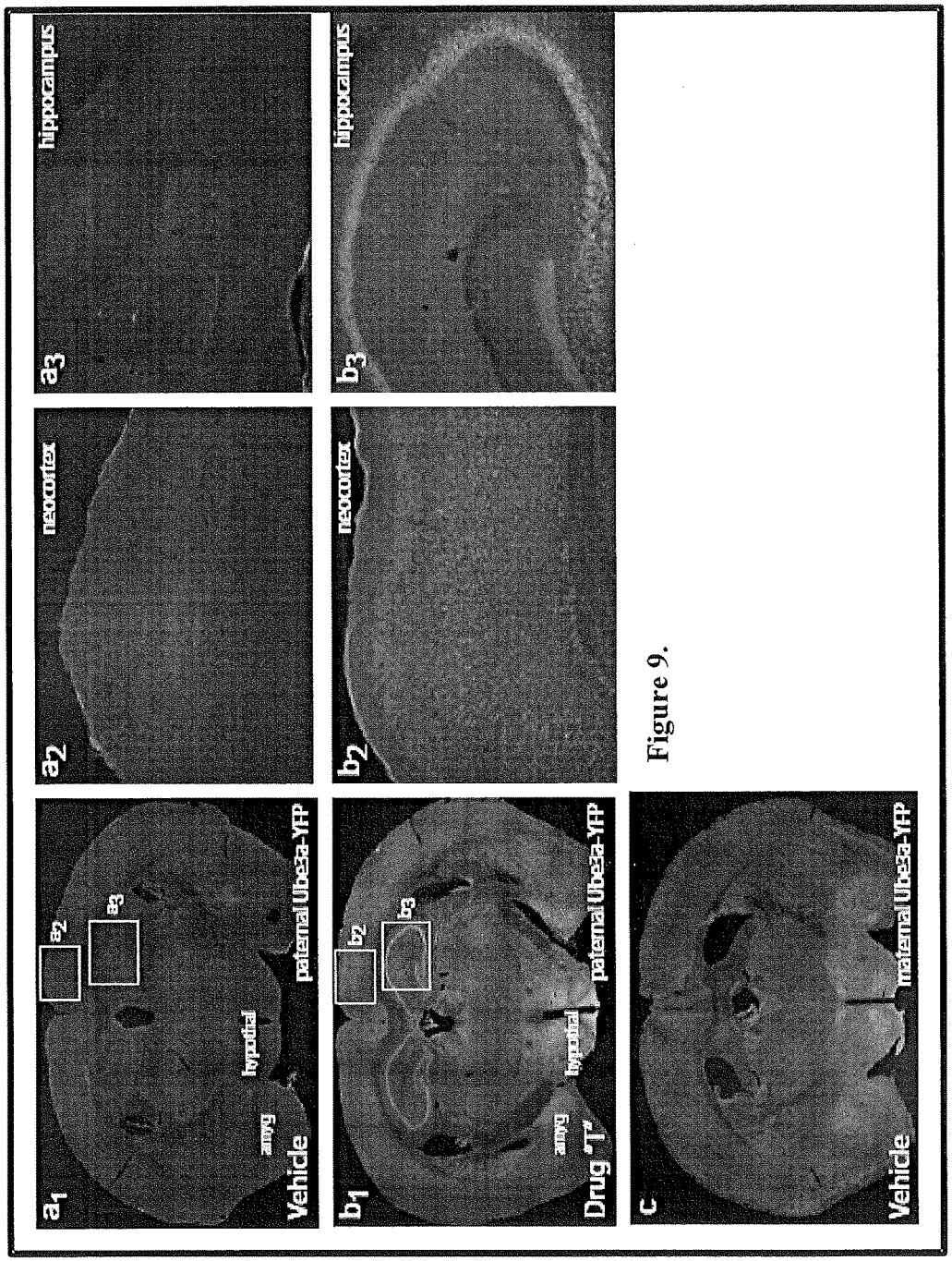
FIGS. 9A-C. One week of topotecan treatment is sufficient to unsilence paternal Ube3a throughout the brain. ($A_1$) Coronal section showing that intracerebroventricular osmotic minipump infusions of vehicle do not unsilence paternal Ube3a-YFP. Boxes highlight regions of the ($A_2$) neocortex and ($A_3$) hippocampus, at higher magnifications. ($B_1$) Topotecan for one week unsilences paternal Ube3a-YFP throughout the brain. Higher magnifications demonstrate paternal Ube3a-YFP unsilencing in ($B_2$) neocortex and ($B_3$) hippocampus. (C) Control labeling of maternal Ube3a-YFP. In this coronal section some of the structures shown in ($A_1$) and ($B_1$) are not visible, such as the hippocampus.
Figure 10:
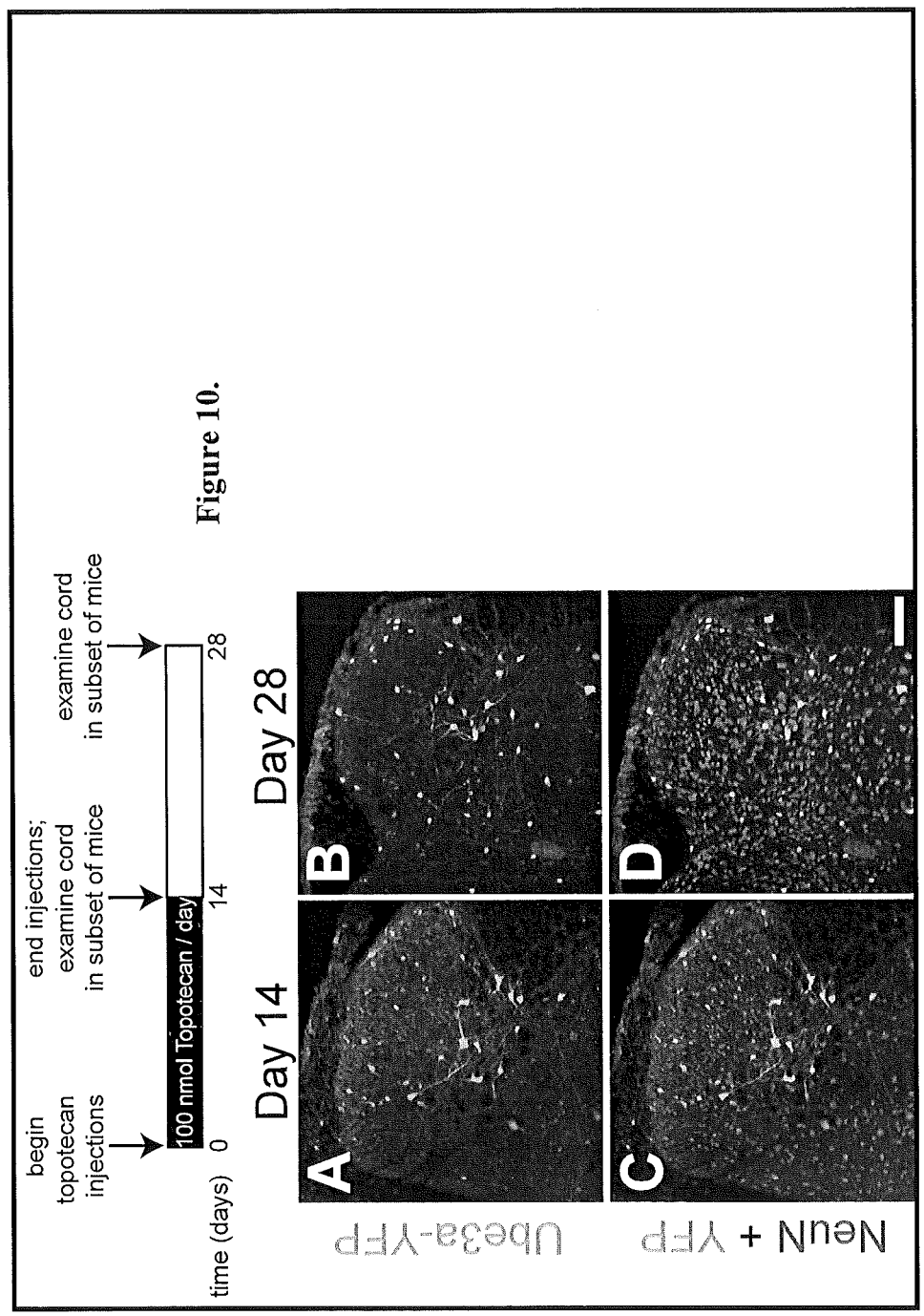
FIGS. 10A-D. Topotecan-induced unsilencing of paternal Ube3a is long-lasting. (A) Two weeks of daily i.t. injections of topotecan (100 nmol/day on 10 of 14 days) unsilences paternal Ube3a-YFP in a subset of neurons (compare to more complete paternal unsilencing with higher drug concentrations in FIG. 9C). (B) 14 days after cessation of topotecan injections, unsilencing of paternal Ube3a persists, suggesting that the loss of imprinting may be permanent. (C-D) Counterstaining of Ube3a-YFP (green) with the pan-neuronal marker NeuN (blue). Scale bar=100 µm. These experiments were performed in mice expressing Ube3a-YFP on the paternal, but not maternal, allele.

Initial studies identified DNA topoisomerase inhibitors as the first class of small molecules that can unsilence an imprinted gene. This is both unprecedented and significant. Topoisomerase inhibitors, used to selectively kill rapidly dividing tumor cells, have never before been shown to unsilence imprinted genes. These findings are thus doubly important, as they identify a novel potential therapeutic use for an existing drug class, as well as a potential strategy that could be applied to treat Angelman syndrome, as well as other disorders involving imprinted genes (e.g., Prader-Willi syndrome, Beckwith-Wiedemann syndrome, Russell-Silver syndrome, and others) (Morison and Reeve, 1998; Butler, 2009). In some embodiments, the methods of the present invention allow for the identification of substances (e.g., small molecules) that optimally unsilence Ube3a in vitro and in vivo. Such a small molecule approach can target neurons throughout the central nervous system (CNS) (FIGS. 8-10).

Figure 1:
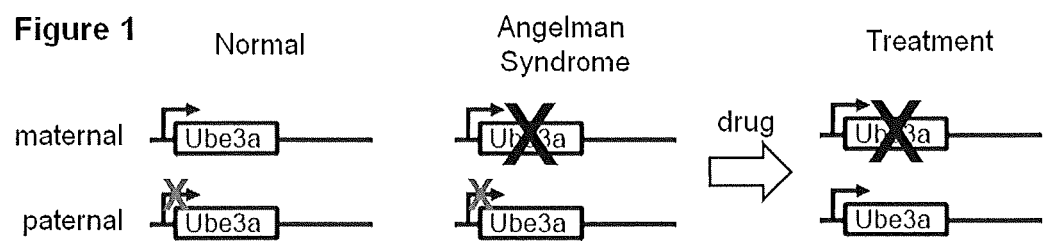
FIG. 1. Schematic of how Angelman syndrome can be treated by unsilencing the intact paternal Ube3a allele.

Small molecules that induce expression of paternal Ube3a translate into an effective treatment for Angelman syndrome (FIGS. 1-2), because the silenced paternal Ube3a allele remains structurally intact in neurons from individuals with the syndrome. In embodiments of this invention, a high-content and high-throughput assay (FIG. 3) has been developed, by which numerous compounds, including irinotecan and topotecan, have been identified that can unsilence the paternal Ube3a allele (FIGS. 4-10). All validated hits to date are DNA topoisomerase inhibitors.

Figure 2:
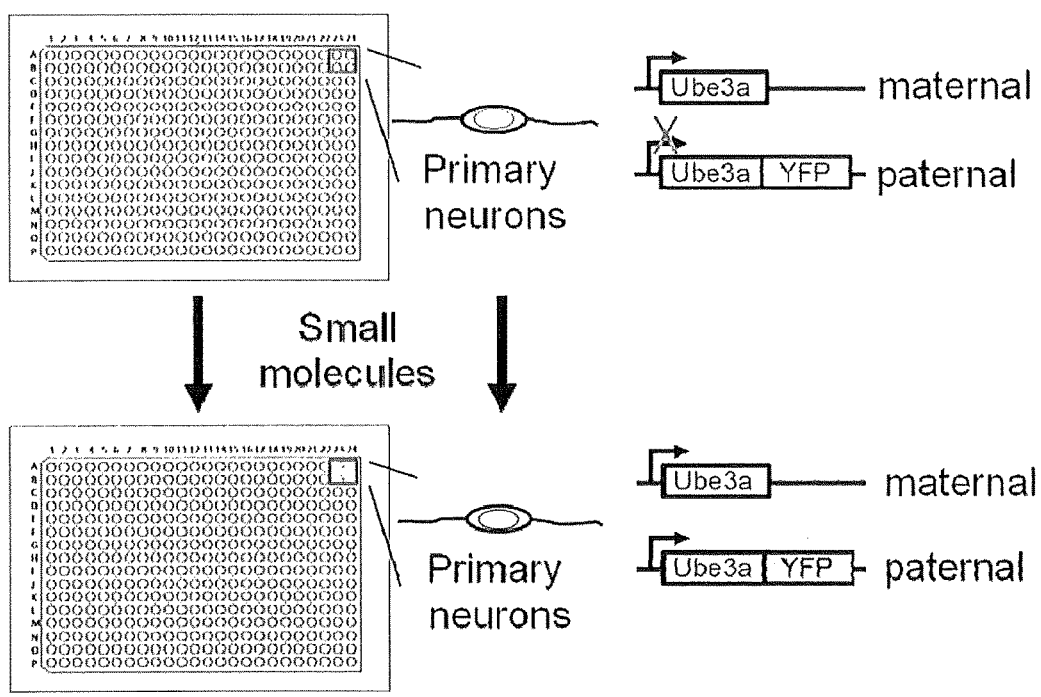
FIG. 2. Schematic of drug discovery approach to identify Angelman syndrome therapeutics. Unsilencing of the paternal Ube3a allele is assessed by a fluorescence-based assay in a 384-well format. 7 DIV cultures are treated in quadruplicate with 10 µM small molecules or 0.2% DMSO (vehicle) using fluid handling robotics. At 72 hr post-drug or DMSO treatments, the YFP signal is amplified by using an anti-GFP antibody (which also recognizes YFP) and Ube3a-YFP fluorescence is assessed in >1200 individual neurons/well using the BD Pathway 855.
Figure 3:
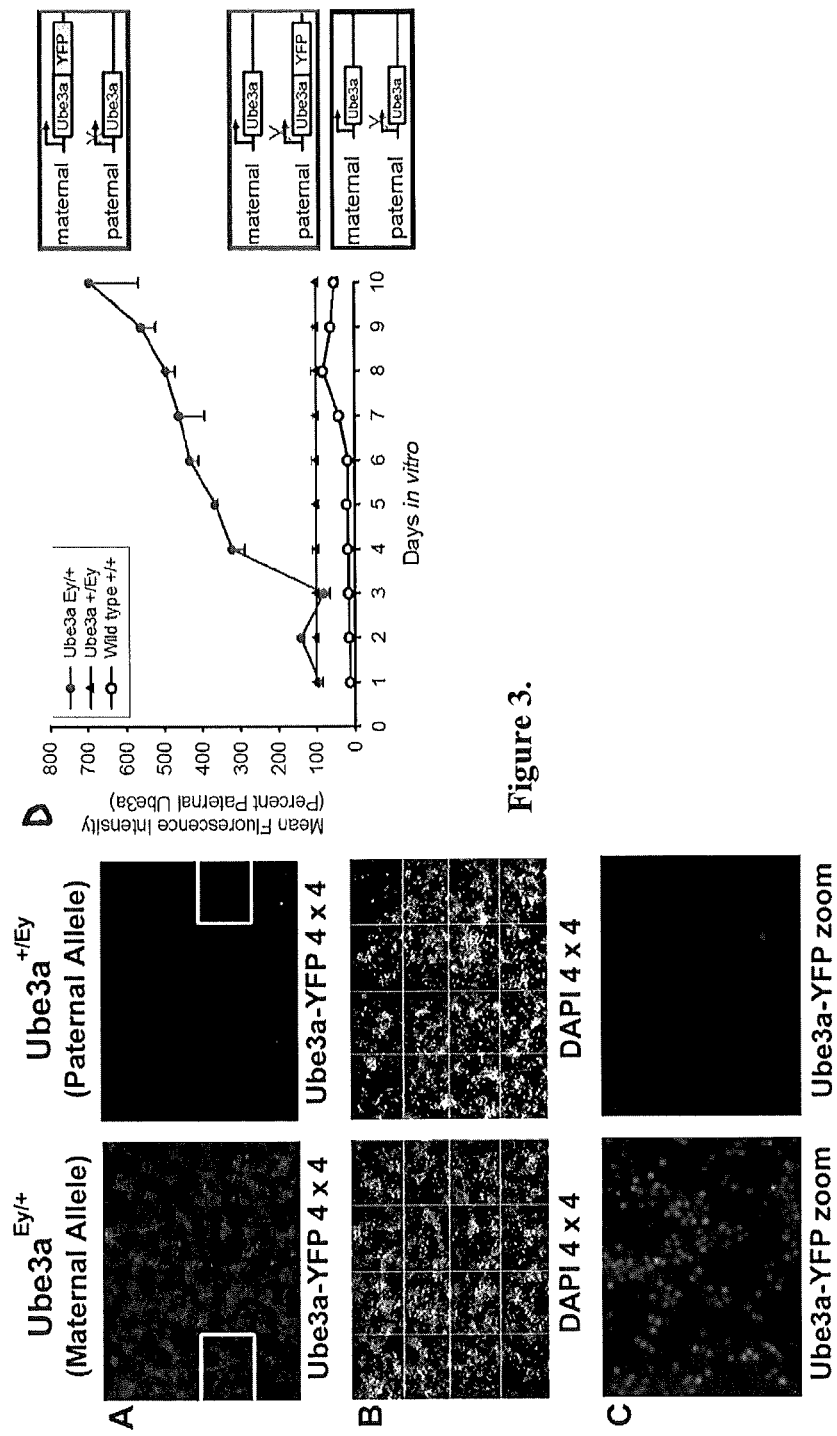
FIGS. 3A-D. High-content imaging of Ube3a-YFP fluorescence can distinguish between active and silenced Ube3a alleles in cortical neurons in vitro. Cortical neurons are shown at 7 DIV from mice expressing the Ube3a-YFP fusion protein on the maternal (Ube3a$^{Ey/+}$) or paternal (Ube3a$^{+/Ey}$) allele. High-content 4×4 montage images show (A) Ube3a-YFP and (B) nuclei stained with DAPI. The insets shown in A are zoomed and shown in C. YFP fluorescence intensity was quantified from signals in individual cells after a background subtraction and by segmenting the cell nuclei area. (D) The mean intensity in all cells in the montaged fields in quadruplicate wells (>1500 cells total/data point) was determined over 10 days in culture for the genotypes (wildtype has no Ube3a-YFP) and expressed as percent paternal Ube3a-YFP. Maternal Ube3a-YFP fluorescence increases after the first few DIV; however, paternal expression is silenced.

The high-content screening method was developed by taking advantage of transgenic Ube3a-YFP knock-in mice and high content imaging microscopy (Dindot et al., 2008). In the transgenic mice, Ube3a is fused to yellow fluorescent protein (YFP), thus allowing the visualization of Ube3a protein expression using fluorescence detection. Using neurons cultured from these mice, a cell-based screening assay was developed that can identify small molecules that unsilence and upregulate expression of paternal Ube3a protein in neurons (FIGS. 2-3). Importantly, this small molecule screening assay preserves paternal silencing of Ube3a and distinguishes between silenced and active Ube3a alleles (FIG. 3). This assay has been optimized for the 384-well plate format, enabling the quantification of Ube3a-YFP protein levels in primary neurons using customized algorithms and a BD-Pathway 855 high-content imaging microscope platform.

This assay has outstanding characteristics (e.g., DMSO stability, Z'-score, reproducibility) for small-molecule screening. Specifically, to validate that this assay was suitable for screening, a Z'-score was calculated based on maternal positive and paternal negative Ube3a signals (FIG. 3) and their standard deviation. The highest Z'-score is one, and >0.5 is considered excellent. Thus, the calculated Z' score of 0.56 for this high-content fluorescence microscopy screen indicates that this approach has excellent metrics for a full-scale high-content-based screen (Zhang et al., 1999). To assess DMSO stability, it was demonstrated that 72 h treatments of vehicle containing up to 1% DMSO had no effect on number, survival, or expression of neurons containing maternal Ube3a-YFP. Therefore, the 0.2% DMSO in media planned in these screening studies should have no adverse effect on neuronal health or survival.

Figure 4:
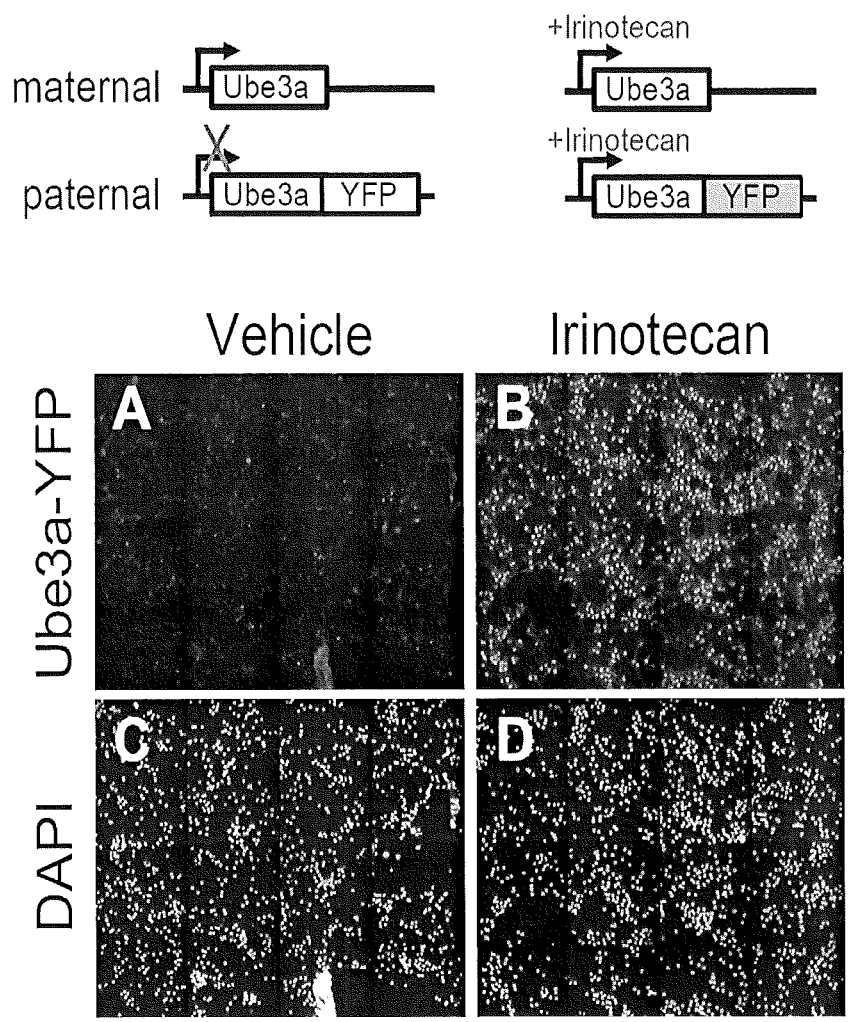
FIGS. 4A-D. Screening identifies that the topoisomerase inhibitor irinotecan unsilences paternal Ube3a in vitro. (A) Paternal Ube3a-YFP is silenced (not expressed) in cultured neurons treated with vehicle (0.2% DMSO). (B) Treating cultures for 72 hr with 10 µM irinotecan turns on paternal Ube3a-YFP. This has been independently reproduced in n=10 experiments, each experiment run on separate days in quadruplicate. (C-D) Neuron density and health is similar in vehicle- and drug-treated cells as evidenced by counterstaining with the nuclear marker DAPI.
Figure 5:
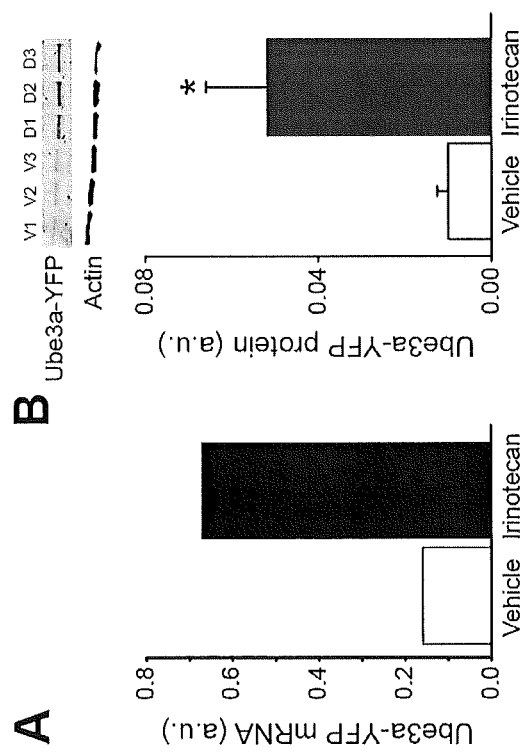
FIGS. 5A-B. Additional assays confirm that irinotecan unsilences the paternal Ube3a-YFP allele. Irinotecan (10 µM for 72 hrs) upregulated the paternal Ube3a-YFP allele as measured by (A) mRNA levels in quantitative RT-PCR experiments and by (B) protein levels assessed by Western blots. V1-V3=samples from separate vehicle-treated cultures; D1-D3=samples from separate drug-treated cultures. *p<0.05, unpaired t-test.
Figure 7:
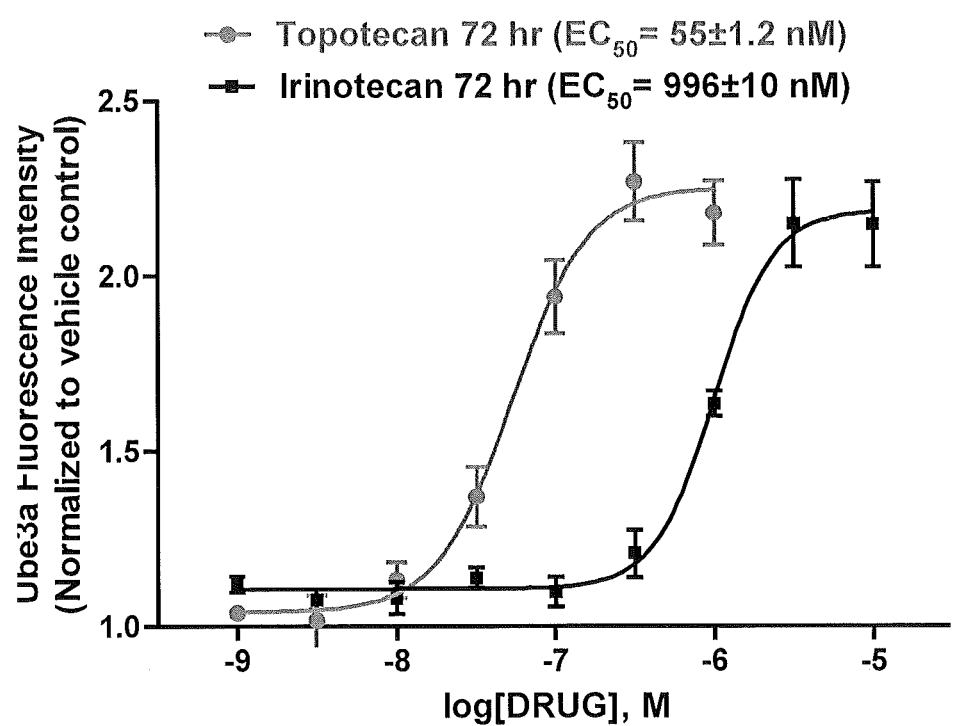
FIG. 7. Concentration-response curves demonstrating the relative potencies for irinotecan and topotecan for unsilencing paternal Ube3a-YFP. These concentration-response curves demonstrate that irinotecan and topotecan have a similar $E_{max}$, but topotecan is ~20 times more potent than irinotecan. Irinotecan $EC_{50}$=996±10 nM; Topotecan $EC_{50}$=55±1.2 nM. Quantified data are mean±SEM from wells treated for 72 hr (>1200 cells total/culture well; n=4 for each data point).

Neurons are cultured from mice expressing Ube3a-YFP on the paternal, but not maternal allele. Drug-induced changes in YFP fluorescence serve as a gauge for unsilencing of the paternal Ube3a allele. Using this small molecule screening approach, it was discovered that the topoisomerase inhibitor irinotecan unsilences and upregulates paternal Ube3a protein (FIG. 4). It was subsequently determined in dose-response studies that irinotecan and the closely related topoisomerase inhibitor topotecan, both unsilence and upregulate paternal Ube3a protein (FIG. 7). Additional studies using the screening platform confirmed compound activities and have identified several distinct topoisomerase inhibitor compounds that unsilence and upregulate paternal Ube3a protein in cortical neurons (Table 1).

Methodology Details.

In all screening assays, primary cortical neurons from Ube3a-YFP mice are isolated from embryonic day 15.5 animals, and the genotype of animals is determined to identify mice that encode the Ube3a-YFP transgene on the paternal allele. Freshly isolated cortical neurons are seeded into 384 well plates and cultured for 7 days. At day in vitro seven, screening is performed using multiple chemical libraries and compound concentration of 10 µM in 0.2% DMSO vehicle. After 72 h of drug exposure (run in quadruplicate wells), neurons are fixed with 4% para formaldehyde and processed for immunofluorescence using an anti-GFP-Alexa 488 conjugated antibody to enhance the signal of Ube3a-YFP in neurons. For image analyses, individual wells of immunofluorescence-processed plates are imaged from DAPI and GFP fluorescence using the BD-Pathway 855 high-content imaging microscope. Ube3a-YFP fluorescence intensities in individual neurons are determined in drug-treated wells and normalized to 0.2% DMSO-treated (i.e., vehicle control) wells using custom written macros and algorithms using NIH Image J and Arrayscan Cell Profiler software programs. These image analyses enable masking of nuclei in individual neurons and determination of Ube3a-YFP fluorescence intensity in the nuclei of individual neurons. Drug-induced increases of >50% are initially binned as screening 'hits' if the increases are consistently observed across multiple runs and if no apparent toxicities are observed by assessing nuclear structure of neurons co-stained with DAPI. Effective 'hit' compounds are validated in formal dose-response experiments to determine relative compound potencies and efficacies.

For these studies, DIV 7 primary neurons encoding paternal Ube3a-YFP are dose treated with hit compounds across seven orders of magnitude in full and half log molar concentrations (3 pM to 30 μM). Ube3a-YFP fluorescence intensities in living neurons are determined again by high-content imaging microscopy after 72 h treatments. The dose response results are analyzed by least squares sigmoidal dose-response curve fitting models using Graphpad Prism 5.0 (Graphpad Software, Inc.). The calculated $EC_{50}$ values (potencies) and Y value top plateau (estimated efficacies or $E_{max}$) enable comparative analyses of the relative potency and efficacy of the identified compounds. To control for potential false positive 'hit' compounds that might have inherent compound fluorescence, cortical neurons from wildtype mice (cells that do not encode Ube3a-YFP) are also treated to determine if 'hit' compounds exhibit inherent fluorescence. None of the identified compounds described display any inherent fluorescence in wildtype neurons.

'Hits' are subsequently evaluated in formal dose-response studies to determine relative compound potencies and efficacies, using the high-content imaging approaches described herein. These experiments enable the identification of the most potent and efficacious small molecule compounds for subsequent testing in vivo. The calculated $EC_{50}$ values (potencies) and relative efficacies guide structure-activity studies and formal rank-order-potency evaluations. The most efficacious and potent compounds are evaluated in time-course experiments in which drug treatments of neurons are extended from 7 to 21 DIV, with drug replacement every 72 hours. These studies determine the chronic effects of the compounds in vitro, providing key information regarding the temporal peak of paternal Ube3a-YFP expression during drug treatments and whether expression is maintained over time in culture.

The most efficacious small molecules are tested in dose-response studies [e.g., 0, 2, 10, 20, and 200 nmol in 5 μl for intracerebroventricular (i.c.v.) injections] in mice expressing paternal Ube3a-YFP (see FIG. 9). The ability of these compounds to upregulate paternal Ube3a in maternal Ube3a-null mice ($Ube3a^{m-/p+}$) is also evaluated. Neurons in the neocortex, hippocampus, spinal cord, and dorsal root ganglia are examined for recovery of Ube3a-YFP expression because it has been demonstrated that Ube3a is imprinted in these regions (FIGS. 8 and 9).

Figure 6:
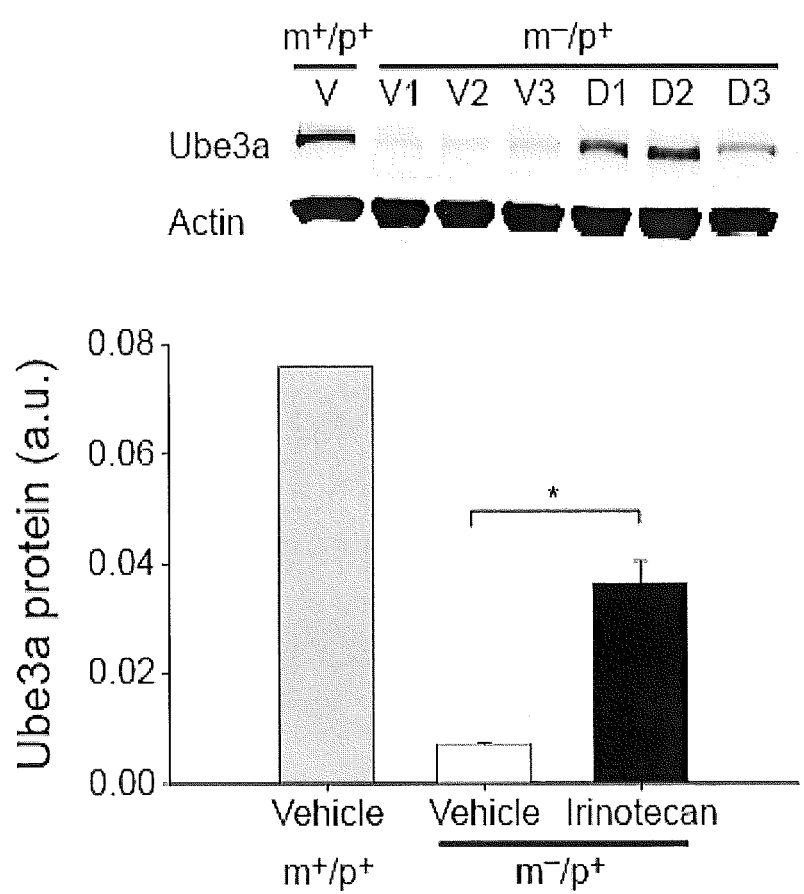
FIG. 6. Irinotecan can unsilence the paternal Ube3a allele in neurons from Angelman syndrome model mice. Irinotecan (10 µM) significantly upregulated Ube3a protein levels in neurons that were cultured from Ube3a$^{m-/p+}$ mice for 72 hrs, with levels reaching ~50% of control levels (in Ube3a$^{m+/p+}$ mice). V=vehicle-treated; D=drug-treated. *p<0.01, unpaired t-test.

Example 2. Quantitative RT-PCR and Western Blot Analysis to Confirm that Compounds Unsilence the Paternal Ube3a-YFP Allele The fluorescence imaging assay of Ube3a-YFP described above is an ideal screening platform to identify active small molecules that unsilence Ube3a; however, it is important to use an orthogonal assay to verify that these topoisomerase inhibitors increase endogenous Ube3a mRNA and protein in neurons. To this end, RT-PCR analyses determined that treatment of neurons with irinotecan significantly increased the level of paternal Ube3a-YFP mRNA, indicating irinotecan increases Ube3a-YFP mRNA expression by unsilencing the paternal allele (FIG. 5A). Similarly, immunoblot analyses determined that irinotecan treatment of neuronal cultures significantly increases paternal Ube3a-YFP protein levels (FIG. 5B). Finally, to confirm that endogenous Ube3a is upregulated by the topoisomerase inhibitor, immunoblot analyses also determined that irinotecan treatment of cortical neurons from Angelman syndrome model mice upregulated paternal Ube3a protein levels (FIG. 6). These findings confirm, using orthogonal assays of RT-PCR and immunoblotting, that the topoisomerase inhibitor irinotecan upregulates paternal Ube3a-YFP in cortical neurons. Similar verification experiments will be performed with other identified hit molecules from screening.

Real Time PCR.

Primary cortical neurons from Ube3a-YFP mice were isolated at embryonic day 13.5 to 15.5 and cultured in 6 well poly-D-lysine-coated plates, and the genotype of animals was determined to identify animals that encode the Ube3a-YFP transgene on the paternal allele. At day in vitro seven, primary cortical neurons that encode paternal Ube3a-YFP were treated with 14 μM irinotecan or 0.2% DMSO for 72 h. Total mRNA was isolated by guanidinium thiocyanate-phenol-chloroform extraction using the Trizol reagent (Invitrogen Inc.). Total mRNAs from samples were converted into cDNA and subjected to real-time PCR (RT-PCR) analyses to quantify Ube3a-YFP transcript levels using oliognucleotide primers against Ube3a (Forward sequence: caaaaggtgcatctaacaactca; reverse sequence: gggaataatcctcactctc) and total transcript reads were normalized to Oaz1 (Forward sequence: cctgagggcagtaaggacag; reverse sequence: ccaagaaagctgaaggttcg).

Western Blotting.

Embryonic day 13.5 to 15.5 mice that encode the paternal Ube3a-YFP transgene or $Ube3a^{m-/p+}$ mice (i.e., AS model mice) were identified and primary cortical neuronal cultures were obtained and plated in 6 well plates. At day in vitro seven, primary cortical neurons were treated with 10 μM irinotecan or 0.2% DMSO for 72 h and total protein lysates were obtained by lysis buffer (1% Triton X-100, 5 mM EDTA, 0.15M NaCl, 10 mM Tris-HCl, pH 7.5, phosphatase inhibitor cocktails 1, protease inhibitor cocktail). To assess Ube3a-YFP protein levels, 7.5 ug of total protein lysates from Ube3a-YFP neurons were separated by 8% SDS-polyacrylamide gel electrophoresis, proteins were transferred to nitrocellulose membranes and immunoblotting was performed using a rabbit anti-GFP antibody (Novus) and Alexa Fluor 680 goat anti-rabbit IgG (Invitrogen). Ube3a-YFP protein bands were visualized by a LiCOR system and to control for protein loading, Ube3a-YFP protein levels were normalized to actin level detected in each sample. To assess Ube3a protein level, immunoblotting was performed using rabbit anti-Ube3a antibody (Abeam) and Alexa Fluor 680 goat anti-rabbit IgG (Invitrogen).

Example 3. In Vivo Studies

To determine if topoisomerase inhibitor compounds are also active in vivo, preclinical testing of compounds was performed using mice expressing paternal Ube3a-YFP. For these studies, Ube3a-YFP mice received topotecan or irinotecan by intracerebroventricular (ICV) or intrathecal (IT) delivery, respectively, and detection of paternal Ube3a-YFP in spinal cord or brain was done using immunofluorescence detection. These in vivo studies determined that IT treatments of mice with irinotecan increased paternal Ube3a-YFP protein in the spinal cord of mice (FIG. 8) and ICV infusions of topotecan increased paternal Ube3a-YFP protein levels throughout the brain (FIG. 9). For dose-response studies, mice receive increasing concentrations of irinotecan or topotecan.

Methodology Details.

Immunohistochemistry, quantitative PCR, and Western blotting methods are used to determine if candidate hit molecules upregulate paternal Ube3a-YFP after in vivo treatments. Comparisons of Ube3a levels between drug- and vehicle-treated paternal Ube3a-YFP mice are assessed. A total of six mice for each treatment at 3-6 months of age are used to identify optimal dosage for potent and effective candidate drugs. This age range was chosen based on successful pilot experiments (FIGS. 8 and 9). Drugs are initially administered for 4 days, based on the success of this dosing regimen in pilot experiments (FIG. 8), although testing lower doses for longer periods and higher doses for shorter periods of time is also informative.

Compounds are administered using three approaches: intracerebroventricularly (i.c.v.), intraperitoneally (i.p.), and intrathecally (i.t.). Each method has its own advantages: i.p. injections are non-invasive and can assess blood-brain barrier (BBB) penetration; i.c.v. injections bypass the BBB to allow direct assessment of drug efficacy in brain; and i.t. injections provide the easiest and most efficient approach for simultaneously assessing drug permeability in the spinal cord, where there is a BBB, and in dorsal root ganglion neurons, where there is no BBB. In addition, all delivery methods could be used to treat symptoms associated with Angelman syndrome. Drugs are initially administered intracerebroventricularly (i.c.v.) and intraperitoneally (i.p.). For compounds like topotecan and other approved medications for which maximum tolerated dose regimens are known in mice (Kim et al., 1992), standard doses used in murine models are used (e.g., 2 mg/kg for topotecan; 20-50 mg/kg irinotecan; Kunimoto et al., 1987). Some of these initial compounds are FDA-approved, and thus well characterized, but for less well characterized compounds low doses are used initially, CNS levels are determined, and subsequent desirable levels are estimated based on $EC_{50}$ for activity in neurons and guidance from veterinary staff on drug tolerance. Drugs are also administered intrathecally (I.t.), starting at low concentrations (e.g., 2 nmol) and increasing concentrations in small increments so that drug tolerance can be assessed.

For proof-of-principle of in vivo effect of irinotecan, intrathecal injection was performed. 5 ul of Irinotecan was injected into unanesthetized mice using the direct lumbar puncture method. A soft cloth is placed over the head and upper body of the animal to keep him calm. The experimenter grasps the pelvic girdle of mouse with his thumb and forefinger. Next, the experimenter traces the spinal column of the mouse with a needle. The disposable 30 gauge ½ inch needle is connected to a 50 ul Luer-hub Hamilton syringe. As long as the experimenter senses the bones of the spinal column, the angle of syringe is lowered at 45 degree to the horizontal. The experimenter inserts the needle 1 mm further to the spinal column. Following the 5 ul injection, the syringe is rotated slightly and removed. Irinotecan is dissolved in 0.9% saline with 10% DMSO. Three different dosages of Irinotecan are used. They are 100, 500 and 1000 nmole. Paternal Ube3a-YFP (+/Ey) mice are used throughout these experiments.

It was found that the paternal Ube3a-YFP allele is silenced in spinal neurons (FIG. 8A). Paternal Ube3a-YFP is also silenced in proprioceptive and mechanoreceptive sensory neurons (located in the dorsal root ganglia; DRG). Drug-like small molecules can readily be delivered to spinal and DRG neurons via intrathecal injections. Strikingly, intrathecal injection of either irinotecan (FIG. 8B; 5 µl injections of 1000 nmol/day for 5 days) or topotecan (FIG. 8C; 5 µl injections of 200 nmol/day for 6 days) into mice in vivo unsilenced the paternal Ube3a-YFP allele in spinal neurons and in DRG neurons. Importantly, neurons appeared normal in drug-treated mice as evidenced by counterstaining with a pan-neuronal marker (FIGS. 8D-F).

In order to unsilence paternal Ube3a in vivo with an emphasis on brain, I.C.V. with osmotic minipump was performed. I.C.V. alone method was performed first to identify the coordinate of injection and the potency of topotecan. Paternal Ube3a-YFP mice were anesthetized with Ketamine/Xylazine (120 mg/kg; 9 mg/kg) and positioned in a stereotaxic head frame. The scalp is shaved and cut, and the skull exposed. The local anesthetic (Bupivacaine, 2.5 mg/ml) is applied on the top of skull and mineral oil is applied on the eyes of the mice. Acetone is applied on the skull to remove any lipid tissues on the skull as well as to dry the skull surface for optimal adhesion. Next, a cannula (Brain Infusion Kit 1, DURECT Corporation) is positioned into a lateral ventricle at the following coordinates (−0.3 mm A/P, +/−1.0 mm M/L, −3.0 mm D/V). The free end of the cannula is connected to an Alzet osmotic minipump via a 2.5-cm-long piece of polyethylene (PE) tubing (cat. no. 0007750, DURECT Corporation). The osmotic minipump and the connecting PE tubing are filled with 16.34 mM topotecan (CPT06, Molcan) dissolved in 50 mM tartaric acid with saline (or control solution without drug). The filled pumps are incubated in sterile saline at 37° C. for at least 4 to 6 hours for priming before being implanted under the dorsal skin of the mouse's back. A needle driver is used to create a subcutaneous pocket in the scapula region to accommodate filled pumps. The cannula base and the attached piece of PE tubing are fixed to the skull with loctite cyanoacrylic. The incision site is closed with prolene suture. During and after surgery, mice are placed on a heating pad. Body weight of mice is recorded daily to assess mouse health. Seven days following minipump implantation, mice are sacrificed following pentobarbital overdose (150 mg/kg, I.P.) and brains are removed for immunofluorescence staining or Western blot analysis.

It was found that irinotecan delivered intracerebroventricularly (i.c.v.) significantly increased Ube3a levels in Angelman syndrome model mice, and that topotecacan delivered i.c.v. dramatically unsilences paternal Ube3a-YFP (FIG. 9). These results indicate that irinotecan and topotecan unsilence Ube3a in vivo.

These in vivo studies indicate that topoisomerase inhibitors are effective at unsilencing the paternal Ube3a allele in individuals with Angelman syndrome. In the present invention, 14 DNA topoisomerase inhibitors are identified that effectively unsilence paternal Ube3a (2 are FDA approved, 12 are topoisomerase I inhibitors, and 2 are topoisomerase II inhibitors).

Angelman syndrome model mice have a number of behavioral phenotypes consistent with Angelman syndrome in humans, including epilepsy, learning defects, and motor abnormalities (Jiang et al., 1998; Miura et al., 2002; Weeber et al., 2003; van Woerden et al., 2007). Since Ube3a is imprinted in proprioceptive neurons, and proprioceptive neurons coordinate movement, these studies suggest the possibility that the motor and coordination symptoms associated with Angelman syndrome might be due to altered proprioceptor function, instead of altered cerebellar function as is commonly thought. In addition, these mice exhibit deficits in synaptic plasticity (long-term depression, LTD, and long-term potentiation, LTP) and ocular dominance plasticity (Jiang et al., 1998; Yashiro et al., 2009; Sato and Stryker, 2010). These well-characterized electrophysiological and behavioral phenotypes in Angelman syndrome model mice can be used to test for drug-induced recovery of function.

Example 4. Persistence of Drug-Induced Upregulation of Paternal Ube3a

To assess if a single topoisomerase inhibitor treatment regimen results in long-lasting effects on paternal Ube3a, Ube3a-YFP mice were administered two weeks of daily intrathecal injections of topotecan (100 nmol/day on 10 of 14 days), and spinal cords were isolated and sectioned and then processed for immunofluorescence detection of Ube3a-YFP. In a separate experiment, mice were similarly administered 100 nmol/day over a two week period, followed by drug washout for 14 days, and spinal cords were isolated and processed for immunofluorescence detection of Ube3a-YFP. These experiments determined that paternal Ube3a-YFP is unsilenced in a subset of neurons and that 14 days after cessation of topotecan injections, unsilencing of paternal Ube3a persists, suggesting that the loss of Ube3a imprinting is long lasting subsequent to topoisomerase treatments (FIG. 10) and may be permanent.

Studies will be done to determine whether a single dosing regimen can unsilence Ube3a permanently. Using optimized delivery and dosing, Ube3a-YFP levels will be assessed immediately, 2 weeks, 2 months, and 1 year after drug treatment (6-8 mice/drug; comparisons will be made to vehicle-treated mice).

Example 5. Age-Dependence of Ube3a Upregulation

Studies will be done to determine whether restoring Ube3a levels in adulthood will be sufficient to fully recover behavioral deficits in Angelman syndrome model mice, or whether Ube3a levels must be restored earlier in life. Thus, assessments will be made of drug-induced increases in Ube3a-YFP, compared to vehicle controls, in mice treated (1) in utero (by intrauterine injection at non-toxic concentrations of drugs at E15.5, an age after the maternal imprint has been established); (2) at postnatal day 10 (P10, an age before electrophysiological defects in the brain are observed; Yashiro et al., 2009); (3) at P20 (an age when synaptic deficits are beginning to be observed); and (4) in adult (>P60) mice.

Example 6. Upregulation of Paternal Ube3a in Angelman Syndrome Mice

Ube3a maternal-null mice are the best model of Angelman syndrome. Studies will be done to define an optimized drug regimen capable of increasing paternally-coded Ube3a protein in Ube3a$^{m-/p+}$ mice.

Example 7. Comparison of Ube3a m/p+ Mice Given Drug or Vehicle Treatments In Vivo Beginning on P20 or P60

Comparisons will be made of Ube3a$^{m-/p+}$ mice given drug or vehicle treatments in vivo beginning on P20 or P60, using the dosing regimen optimized as described herein. Additional comparisons will be made to wildtype littermates (Ube3a$^{m+/p+}$ mice) receiving vehicle treatments. Recovery of function will be assessed as described herein upon completion of drug treatment.

Example 8. RNA-Interference (RNAi) Approaches

Figure 12:
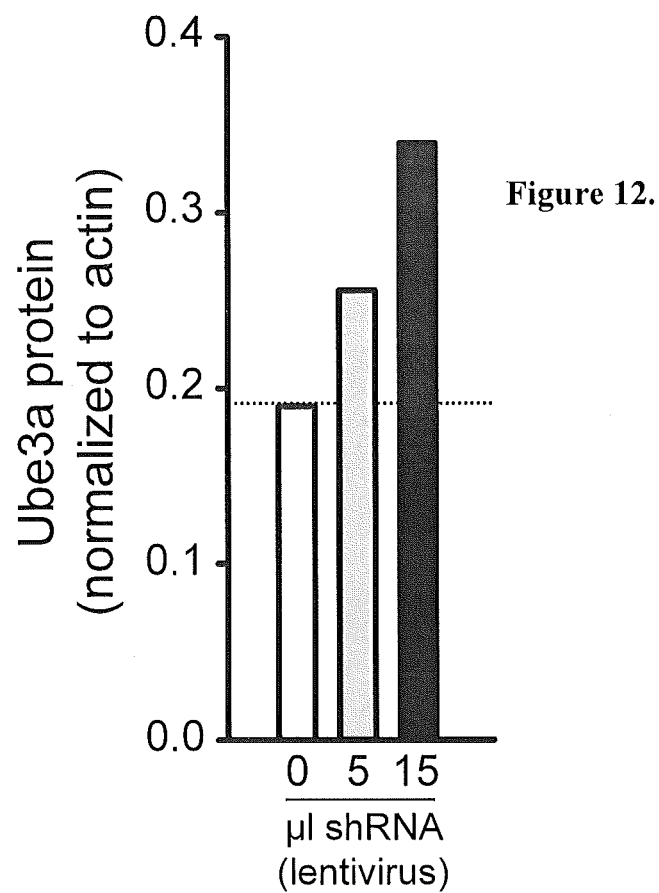
FIG. 12. Topoisomerase I RNAi-mediated knockdown increases Ube3a protein expression. Western blots were used in preliminary studies to quantify protein levels of Ube3a in cultured neurons after 5 days of RNAi-treatment.

Topoisomerase inhibitors are shown herein to unsilence paternal Ube3a, suggesting topoisomerase enzymes regulate Ube3a imprinting. Transient knock-down of topoisomerase I protein is a complementary method to test if loss of topoisomerase function unsilences Ube3a. To determine if loss of topoisomerase function by protein knockdown also results in unsilencing of Ube3a, RNA-interference (RNAi) for topoisomerase I was assessed. Cultured cortical neurons from the Ube3a-YFP transgenic mice were treated with increasing concentrations of lentivirus-based shRNA targeting topoisomerase I (Topo I). After five days of treatment with siRNA, total protein lysates were obtained and Ube3a-YFP protein levels were determined by Western blotting. Delivery of lentiviruses that contain shRNA for topoisomerase I increased Ube3a protein levels in cortical neurons indicating topoisomerase I knockdown increases Ube3a expression (FIG. 12).

In further studies, cultured cortical neurons from the mice described herein will be treated with lentivirus-based shRNA targeting Topoisomerase I (Topo I), Topo IIa, Topo IIb, non-targeting shRNA (scrambled negative control), vector only (control), or GFPshRNA (control). In some experiments, to complement shRNA approaches, siRNA for RNAi-mediated knockdown will be alternatively used. For these experiments, cultured cortical neurons will be transfected with siRNA targeting Topo I, Topo IIa, or Topo IIb using lipofectamine 2000. Scrambled siRNA will be used as a negative control. For all RNAi experiments, high-content imaging and Western blots will be used to assess Ube3a expression following topoisomerase knockdown. Similar approaches can be used to validate that topoisomerase expression and function is required for Ube3a imprinting and silencing.

Example 9. Methylation Assays

Because the allele-specific activation/silencing of Ube3a is thought to occur through differential DNA methylation (Glenn et al., 1993; Sutcliffe et al., 1994; Glenn et al., 1997), studies will be carried out to determine whether topoisomerase inhibitors alter DNA methylation. To do this, DNA methylation status within the Angelman syndrome/Prader-Willi imprinting centers will be determined following drug (or vehicle) treatment of cortical neurons using the sodium bisulfite conversion method (Huang and Akbarian, 2007). In addition, the Sequenom MassARRAY platform can be used to identify and quantify drug-induced changes across differentially methylated regions as well as pyrosequencing approaches to further define regions of differential methylation.

Example 10. Histone Modification Assays

Because histone modifications provide another mechanism to alter imprinting status (Soejima and Wagstaff, 2005; Kim and Huibregtse, 2009), studies will be carried out to examine whether histone modifications occur with active small molecules (compared to vehicle treatments). Levels of H3K4 m3 and H3K27me3 within the relevant imprinting center will be quantified by SYBR-based RT-PCR with custom-made primers.

Example 11. Deep Sequencing

Studies will be conducted to test whether the compounds of this invention alter neuronal gene expression. Total brain RNA will be extracted from drug- or vehicle-treated neurons taken from reciprocal progeny of the CAST/EiJ and BALB/cByJ mouse strains. These divergent mouse strains are amenable to single nucleotide polymorphism (SNP) analyses, allowing for assessment of transcriptional changes in both imprinted and non-imprinted genes, cDNA will be examined using the Illumina Genome Analyzer (Wang et al., 2008).

Example 12. Synaptic Plasticity Ex Vivo

Ube3a$^{m-/p+}$ mice lack normal synaptic plasticity (LTD/LTP) in visual cortex (Yashiro et al., 2009), and studies will be carried out to determine whether drug treatments can restore normal plasticity. Field potential recordings will be used to assess synaptic plasticity in visual cortex as described (Yashiro et al., 2009). Field EPSPs (fEPSPs) will be generated in visual cortex slices by providing extracellular layer 4 stimulation and recording in layers 2/3 (Kirkwood et al., 1993; Philpot et al., 2007). Changes in synaptic strength after 1, 20, 40, or 100 Hz stimulation will be assessed by comparing changes in the fEPSP amplitude.

Example 13. Synaptic Plasticity In Vivo

Ocular dominance plasticity is absent in Ube3a$^{m-/p+}$ mice (Yashiro et al., 2009). To examine in vivo cortical plasticity in drug- and vehicle-treated mice, chronic visually-evoked potential (VEP) recordings will be obtained in unanesthetized mice to assess ocular dominance plasticity as described (Yashiro et al., 2009).

Example 14. Behavioral Recovery

Figure 11:
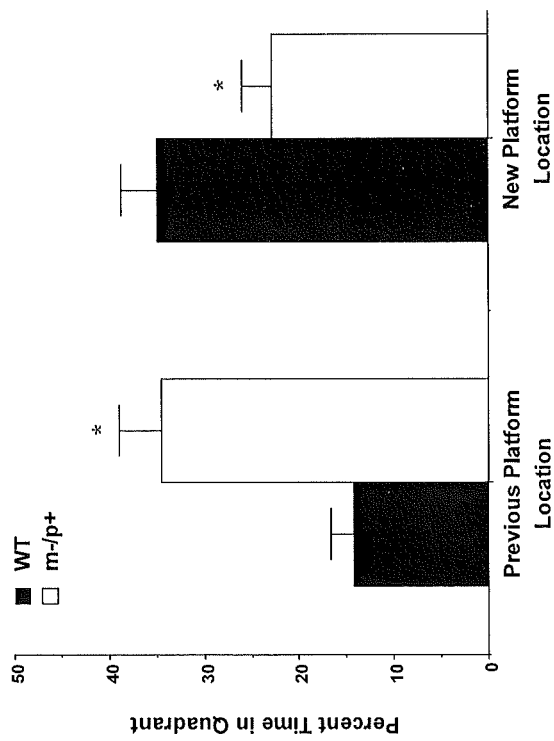
FIG. 11. Ube3a-deficient mice exhibit deficits in water-maze reversal learning. Significant effects of genotype were observed in reversal learning [main effect of genotype, F(1,19)=7.47, p=0.0132; genotype X target location interaction, F(3,57)=6.29, p=0.0009]. During acquisition, within-genotype repeated measures ANOVAs showed target selectivity in both groups [wildtype, F(3,27)=19.23, p<0.0001; m−/p+, F(3,30)=20.62, p<0.0001]. However, only the wild-type group demonstrated a significant preference for the new platform location [F(3,27)=40.06, p<0.0001]. *p<0.05

Angelman syndrome mice have quantifiable deficits in behavior, including poor motor performance, a propensity for seizures, abnormal gait, and deficits in context-dependent fear learning and spatial learning (Jiang et al., 1998; van Woerden et al., 2007). To assess the likely therapeutic value of candidate molecules, evaluations will be done to determine the extent to which candidate molecules ameliorate behavioral deficits in Ube3a$^{m-/p+}$ mice. A total of 10-12 mice for each treatment (drug- or vehicle-treated) and genotype (Ube3a$^{m-/p+}$ or Ube3a$^{m+/p+}$) will be assessed by behavioral tests, in a blinded manner. Bar-crossing, footprint analysis, and rotating rod tests will be used to assess motor function of mice. Seizure susceptibility in response to cage grating will also be tested. Gait will be measured by assessing stride length and forepaw/hind paw overlap as described (Trushina et al., 2006). Spatial learning will be assessed using the Morris water maze (FIG. 11), and data will be recorded, including the time taken to reach platform, the time spent in each quadrant of the pool, and total distance traveled. Context-dependent fear learning will be determined using previously described approaches (Jiang et al., 1998).

Example 15. Additional Data/Observations

Preliminary Affymetrix GeneChip data indicate that there are not large-scale expression changes when cultured neurons are treated with irinotecan (e.g., <1% of the genes on chip showed a 1.5× fold increase; and <2% showed a decrease). Both irinotecan and topotecan are FDA-approved chemotherapeutics (Koster et al., 2007). These drugs are used clinically and are in trials for treating brain tumors (Feun and Savaraj, 2008). This makes it unlikely that any epigenetic changes caused by topoisomerase inhibitors would have insurmountable toxicities.

In support of the idea that effective concentrations of irinotecan do not increase cell death, (1) a similar number of pyknotic nuclei were detected in vehicle- and irinotecan-treated cultures, and (2) no evidence for drug-induced increases in apoptotic pathways was observed by microarray. To further verify that there are no significant drug-induced increases in cell death (compared to vehicle controls), immuncytochemical assays of apoptosis (e.g. TUNEL assays) will be performed. Importantly, topoisomerase inhibitors have tolerable side effects when administered chronically to treat cancer in adults and children (Schellens et al., 1996; Stewart et al., 1996; Creemers et al., 1997; Vassal et al., 1998; Rose et al., 2006). With appropriate dosing, it might be possible to unsilence Ube3a while minimizing these side effects. The tolerance of these FDA-approved drugs in humans is well established (Seiter, 2005; Hartmann and Lipp, 2006). The preliminary data shown herein suggest that the drug-induced loss of paternal Ube3a imprinting may be permanent (FIG. 10). If the loss of imprinting is indeed permanent, then a brief drug treatment regimen may be all that is needed for a lifelong therapeutic effect.

Studies described herein demonstrate that irinotecan can cross the blood brain barrier (BBB) (FIGS. 8 and 10). Moreover, consistent with findings that topotecan has greater potency (FIG. 7), stability, and permeability across the BBB than irinotecan (Herben et al., 1996; Herben et al., 1998; Motl et al., 2006), studies described herein show that topotecan is even more effective at unsilencing paternal Ube3a in spinal cord (compare FIGS. 8B and 8C). It was also determined that infusions of topotecan directly into the brain, thereby bypassing the BBB, upregulates paternal Ube3a throughout the brain (FIG. 9).

It is expected that cellular plasticity and behavioral deficits in Ube3a$^{m-/p+}$ mice can be rescued. A failure to recover behavioral deficits may be overcome by dosage adjustment, increasing the time of drug treatment, or by combining different candidate molecules. It is also expected that drug-induced therapies might provide some degree of benefit regardless of the age treatment is begun, as has been observed in other neurodevelopmental disorders (Ehninger et al., 2008). In support of the idea that mental retardations can be overcome later in life, the late-onset reinstatement of MeCP2 can rescue deficits associated with Rett syndrome, a mental retardation and epigenetic disorder (Guy et al., 2007).

Inappropriately high gene dosage seems unlikely, however, for the following reasons. (1) It is difficult to increase Ube3a levels much above normal levels, likely because Ube3a is an E3 ubiquitin ligase that targets itself for proteasomal degradation (Crinelli et al., 2008). This places an upper limit on Ube3a protein levels. (2) At least two of the effective topoisomerase inhibitors are FDA-approved and widely used clinically. Thus, regardless of changes in gene dosage, the tolerance of these compounds in humans is already well established. (3) Neurons are the only class of cells that exhibit paternal silencing of Ube3a; thus any small molecules that unsilence the paternal allele are likely to have their largest effects in neurons. (4) Because the maternal Ube3a allele is deleted or mutated in individuals with Angelman syndrome, paternal unsilencing of Ube3a is only capable of producing mono-allelic activation of the gene. (5) Dosing of the compounds of this invention can be regulated to minimize inappropriately high expression levels of Ube3a in neurons.

REFERENCES FOR EXAMPLES 1-15

Abbas A I, Urban D J, Jensen N H, Farrell M S, Kroeze W K, Mieczkowski P, Wang Z, Roth B L (2010) Assessing serotonin receptor mRNA editing frequency by a novel ultra high-throughput sequencing method. *Nucleic Acids Res* 38:e118.

Akbarian S, Huang H S (2009) Epigenetic regulation in human brain-focus on histone lysine methylation. *Biol Psychiatry* 65:198-203.

Albrecht U, Sutcliffe J S, Cattanach B M, Beechey C V, Armstrong D, Eichele G, Beaudet A L (1997) Imprinted expression of the murine Angelman syndrome gene, Ube3a, in hippocampal and Purkinje neurons. *Nat Genet* 17:75-78.

Alexander G M, Rogan S C, Abbas A I, Armbruster B N, Pei Y, Allen J A, Normeman R J, Hartmann J, Moy S S, Nicolelis M A, McNamara J O, Roth B L (2009) Remote control of neuronal activity in transgenic mice expressing evolved G protein-coupled receptors. *Neuron* 63:27-39.

Arn P H, Williams C A, Zori R T, Driscoll D J, Rosenblatt D S (1998) Methylenetetrahydrofolate reductase deficiency in a patient with phenotypic findings of Angelman syndrome. *Am J Med Genet* 77:198-200.

Bacino C A, Peters S, Goddard-Finegold J, Smiith O, O'Brien W, Madduri N, Glaze D, Shinawi L, Beaudet A (2003) A randomized therapeutic trial in Angelman syndrome using betaine and folic acid. *Am J Hum Genet* 73 (suppl.):334.

Bomgaars L, Berg S L, Blaney S M (2001) The development of camptothecin analogs in childhood cancers. *Oncologist* 6:506-516.

Browne C E, Dennis N R, Maher E, Long F L, Nicholson J C, Sillibourne J, Barber J C (1997) Inherited interstitial duplications of proximal 15q: genotype-phenotype correlations. *Am J Hum Genet* 61:1342-1352.

Butler M G (2009) Genomic imprinting disorders in humans: a mini-review. *J Assist Reprod Genet.* 26:477-486.

Carol H, Houghton P J, Morton C L, Kolb E A, Gorlick R, Reynolds C P, Kang M H, Maris J M, Keir S T, Watkins A, Smith M A, Lock R B (2010) Initial testing of topotecan by the pediatric preclinical testing program. *Pediatr Blood Cancer* 54:707-715.

Clayton-Smith J, Laan L (2003) Angelman syndrome: a review of the clinical and genetic aspects. *J Med Genet* 40:87-95.

Collins I, Weber A, Levens D (2001) Transcriptional consequences of topoisomerase inhibition. *Mol Cell Biol* 21:8437-8451.

Cook E H, Jr., Lindgren V, Leventhal B L, Courchesne R, Lincoln A, Shulman C, Lord C, Courchesne E (1997) Autism or atypical autism in maternally but not paternally derived proximal 15q duplication. *Am J Hum Genet* 60:928-934.

Corbett K D, Berger J M (2004) Structure, molecular mechanisms, and evolutionary relationships in DNA topoisomerases. *Annu Rev Biophys Biomol Struct* 33:95-118.

Creemers G J, Gerrits C J, Eckardt J R, Schellens J H, Burris H A, Planting A S, Rodriguez G I, Loos W J, Hudson I, Broom C, Verweij J, Von Hoff D D (1997) Phase I and pharmacologic study of oral topotecan administered twice daily for 21 days to adult patients with solid tumors. *J Clin Oncol* 15:1087-1093.

Crinelli R, Bianchi M, Menotta M, Carloni E, Giacomini E, Pennati M, Magnani M (2008) Ubiquitin over-expression promotes E6AP autodegradation and reactivation of the p53/MDM2 pathway in HeLa cells. *Mol Cell Biochem* 318:129-145.

Cruz-Correa M, Zhao R, Oviedo M, Bernabe R D, Lacourt M, Cardona A, Lopez-Enriquez R, Wexner S, Cuffari C, Hylind L, Platz E, Cui H, Feinberg A P, Giardiello F M (2009) Temporal stability and age-related prevalence of loss of imprinting of the insulin-like growth factor-2 gene. *Epigenetics* 4:114-118.

Dan B (2008) *Angelman Syndrome* London: Mac Keith Press. 256 pp.

Dan B (2009) Angelman syndrome: current understanding and research prospects. *Epilepsia* 50:2331-2339.

Dindot S V, Antalffy B A, Bhattacharjee M B, Beaudet A L (2008) The Angelman syndrome ubiquitin ligase localizes to the synapse and nucleus, and maternal deficiency results in abnormal dendritic spine morphology. *Hum Mol Genet* 17:111-118.

Ehninger D, Li W, Fox K, Stryker M P, Silva A J (2008) Reversing neurodevelopmental disorders in adults. *Neuron* 60:950-960.

Elphick G F, Querbes W, Jordan J A, Gee G V, Eash S, Manley K, Dugan A, Stanifer M, Bhatnagar A, Kroeze W K, Roth B L, Atwood W J (2004) The human polyomavirus, JCV, uses serotonin receptors to infect cells. *Science* 306:1380-1383.

Feun L, Savaraj N (2008) Topoisomerase I inhibitors for the treatment of brain tumors. *Expert Rev Anticancer Ther* 8:707-716.

Gaulton K J, Nammo T, Pasquali L, Simon J M, Giresi P G, Fogarty M P, Panhuis T M, Mieczkowski P, Secchi A, Bosco D, Berney T, Montanya E, Mohlke K L, Lieb J D, Ferrer J (2010) A map of open chromatin in human pancreatic islets. *Nat Genet* 42:255-259.

Glenn C C, Driscoll D J, Yang T P, Nicholls R D (1997) Genomic imprinting: potential function and mechanisms revealed by the Prader-Willi and Angelman syndromes. *Mol Hum Reprod* 3:321-332.

Glenn C C, Nicholls R D, Robinson W P, Saitoh S, Niikawa N, Schinzel A, Horsthemke B, Driscoll D J (1993) Modification of 15q11-q13 DNA methylation imprints in unique Angelman and Prader-Willi patients. *Hum Mol Genet* 2:1377-1382.

Guy J, Gan J, Selfridge J, Cobb S, Bird A (2007) Reversal of neurological defects in a mouse model of Rett syndrome. *Science* 315:1143-1147.

Hartmann J T, Lipp H P (2006) Camptothecin and podophyllotoxin derivatives: inhibitors of topoisomerase I and II—mechanisms of action, pharmacokinetics and toxicity profile. *Drug Saf* 29:209-230.

He H H, Meyer C A, Shin H, Bailey S T, Wei G, Wang Q, Zhang Y, Xu K, Ni M, Lupien M, Mieczkowski P, Lieb J D, Zhao K, Brown M, Liu X S (2010) Nucleosome dynamics define transcriptional enhancers. *Nat Genet* 42:343-347.

Herben V M, Ten Bokkel Huinink W W, Beijnen J H (1996) Clinical pharmacokinetics of topotecan. *Clin Pharmacokinet* 31:85-102.

Herben V M, Ten Bokkel Huinink W W, Schellens J H, Beijnen J H (1998) Clinical pharmacokinetics of camptothecin topoisomerase I inhibitors. *Pharm World Sci* 20:161-172.

Huang H S, Akbarian S (2007) GAD1 mRNA expression and DNA methylation in prefrontal cortex of subjects with schizophrenia. *PLoS One* 2:e809.

Huang H S, Matevossian A, Jiang Y, Akbarian S (2006) Chromatin immunoprecipitation in postmortem brain. *J Neurosci Methods* 156:284-292.

Huang H S, Matevossian A, Whittle C, Kim S Y, Schumacher A, Baker S P, Akbarian S (2007) Prefrontal dysfunction in schizophrenia involves mixed-lineage leukemia 1-regulated histone methylation at GABAergic gene promoters. *J Neurosci* 27:11254-11262.

Huang X P, Setola V, Yadav P N, Allen J A, Rogan S C, Hanson B J, Revankar C, Robers M, Doucette C, Roth B L (2009) Parallel functional activity profiling reveals valvulopathogens are potent 5-HT2B receptor agonists: implications for drug safety assessment. *Mol Pharmacol* 76:710-722.

Jiang Y H, Armstrong D, Albrecht U, Atkins C M, Noebels J L, Eichele G, Sweatt J D, Beaudet A L (1998) Mutation of the Angelman ubiquitin ligase in mice causes increased cytoplasmic p53 and deficits of contextual learning and long-term potentiation. *Neuron* 21:799-811.

Keiser M J, Setola V, Irwin J J, Laggner C, Abbas A I, Hufeisen S J, Jensen N H, Kuijer M B, Matos R C, Tran T B, Whaley R, Glennon R A, Hert J, Thomas K L, Edwards D D, Shoichet B K, Roth B L (2009) Predicting new molecular targets for known drugs. *Nature* 462:175-181.

Kim H C, Huibregtse J M (2009) Polyubiquitination by HECT E3s and the determinants of chain type specificity. *Mol Cell Biol* 29:3307-3318.

Kim J H, Kim S H, Kolozsvary A, Khil M S (1992) Potentiation of radiation response in human carcinoma cells in vitro and murine fibrosarcoma in vivo by topotecan, an inhibitor of DNA topoisomerase I. *Int J Radiat Oncol Biot Phys* 22:515-8.

Kirkwood A, Dudek S M, Gold J T, Aizenman C D, Bear M F (1993) Common forms of synaptic plasticity in the hippocampus and neocortex in vitro. *Science,* 260:1518-1521.

Koster D A, Palle K, Bot E S, Bjornsti M A, Dekker N H (2007) Antitumour drugs impede DNA uncoiling by topoisomerase I. *Nature* 448:213-217.

Kunimoto T, Nitta K, Tanaka T, Uehara N, Baba H, Takeuchi M, Yokokura T, Sawada S, Miyasaka T, Mutai M (1987) Antitumor activity of 7-ethyl-10-[4-(1-piperidino)-1-piperidino]carbonyloxy-camptothecin, a novel water-soluble derivative of camptothecin, against murine tumors. *Cancer Res* 47:5944-5947.

Liu L F, Wang J C (1987) Supercoiling of the DNA template during transcription. *Proc Natl Acad Sci USA* 84:7024-7027.

Lossie A C, Whitney M M, Amidon D, Dong H J, Chen P, Theriaque D, Hutson A, Nicholls R D, Zori R T, Williams C A, Driscoll D J (2001) Distinct phenotypes distinguish the molecular classes of Angelman syndrome. *J Med Genet* 38:834-845.

Miura K, Kishino T, Li E, Webber H, Dikkes P, Holmes G L, Wagstaff J (2002) Neurobehavioral and electroencephalographic abnormalities in Ube3a maternal-deficient mice. *Neurobiol Dis* 9:149-159.

Moeschler J B, Mohandas T K, Hawk A B, Noll W W (2002) Estimate of prevalence of proximal 15q duplication syndrome. *Am J Med Genet* 111:440-442.

Morison I M, Reeve A E (1998) Insulin-like growth factor 2 and overgrowth: molecular biology and clinical implications. *Mol Med Today* 4:110-115.

Motl S, Zhuang Y, Waters C M, Stewart C F (2006) Pharmacokinetic considerations in the treatment of CNS tumours. *Clin Phctrmacokinet* 45:871-903.

Moy S S, Nadler J J (2008) Advances in behavioral genetics: mouse models of autism. *Mol Psychiatry* 13:4-26.

Moy S S, Nadler J J, Magnuson T R, Crawley J N (2006) Mouse models of autism spectrum disorders: the challenge for behavioral genetics. *Am J Med Genet C Semin Med Genet* 142:40-51.

Moy S S, Nadler J J, Perez A, Barbaro R P, Johns J M, Magnuson T R, Piven J, Crawley J N (2004) Sociability and preference for social novelty in five inbred strains: an approach to assess autistic-like behavior in mice. *Genes Brain Behav* 3:287-302.

Moy S S, Nadler J J, Young N B, Normeman R J, Grossman A W, Murphy D L, D'Ercole A J, Crawley J N, Magnuson T R, Lauder J M (2009) Social approach in genetically engineered mouse lines relevant to autism. *Genes Brain Behav* 8:129-142.

Moy S S, Nadler J J, Young N B, Perez A, Holloway L P, Barbaro R P, Barbaro J R, Wilson L M, Threadgill D W, Lauder J M, Magnuson T R, Crawley J N (2007) Mouse behavioral tasks relevant to autism: phenotypes of 10 inbred strains. *Behav Brain Res* 176:4-20.

O'Connor K A, Roth B L (2005) Finding new tricks for old drugs: an efficient route for public-sector drug discovery. *Nat Rev Drug Discov* 4:1005-1014.

Pelc K, Cheron G, Dan B (2008) Behavior and neuropsychiatric manifestations in Angelman syndrome. *Neuropsychiatr Dis Treat* 4:577-584.

Philpot B D, Cho K K, Bear M F (2007) Obligatory Role of NR2A for Metaplasticity in Visual Cortex. *Neuron* 53:495-502.

Reik W (2007) Stability and flexibility of epigenetic gene regulation in mammalian development. *Nature* 447:425-432.

Roberts S E, Dennis N R, Browne C E, Willatt L, Woods G, Cross I, Jacobs P A, Thomas S (2002) Characterisation of interstitial duplications and triplications of chromosome 15q11-q13. *Hum Genet* 110:227-234.

Rodriguez-Galindo C, Radomski K, Stewart C F, Furman W, Santana V M, Houghton P J (2000a) Clinical use of topoisomerase I inhibitors in anticancer treatment. *Med Pediatr Oncol* 35:385-402, Rodriguez-Galindo C, Poquette C A, Marina N M, Head D R, Cain A, Meyer W H, Santana V M, Pappo A S (2000b) Hematologic abnormalities and acute myeloid leukemia in children and adolescents administered intensified chemotherapy for the Ewing sarcoma family of tumors. *J Pediatr Hematol Oncol* 22:321-329.

Rose P G, Markman M, Bell J G, Fusco N L (2006) Sequential prolonged oral topotecan and prolonged oral etoposide as second-line therapy in ovarian or peritoneal carcinoma: a phase I Gynecologic Oncology Group study. *Gynecol Oncol* 102:236-239.

Roth B L, Sheffler D J, Kroeze W K (2004) Magic shotguns versus magic bullets: selectively non-selective drugs for mood disorders and schizophrenia. *Nat Rev Drug Discov* 3:353-359.

Sato M, Stryker M P (2010) Genomic imprinting of experience-dependent cortical plasticity by the ubiquitin ligase gene Ube3a. *Proc Natl Acad Sci USA* 107:5611-5617.

Sawtell N B, Frenkel M Y, Philpot B D, Nakazawa K, Tonegawa S, Bear M F (2003) NMDA receptor-dependent ocular dominance plasticity in adult visual cortex. *Neuron* 38:977-985.

Schellens J H, Creemers G J, Beijnen J H, Rosing H, de Boer-Dennert M, McDonald M, Davies B, Verweij J (1996) Bioavailability and pharmacokinetics of oral topotecan: a new topoisomerase I inhibitor. *Br J Cancer* 73:1268-1271.

Schroer R J, Phelan M C, Michaelis R C, Crawford E C, Skinner S A, Cuccaro M, Simensen R J, Bishop J, Skinner C, Fender D, Stevenson R E (1998) Autism and maternally derived aberrations of chromosome 15q. *Am J Med Genet* 76:327-336.

Seiter K (2005) Toxicity of the topoisomerase I inhibitors. *Expert Opin Drug Saf* 4:45-53.

Soejima H, Wagstaff J (2005) Imprinting centers, chromatin structure, and disease. *J Cell Biochem* 95:226-233.

Souza V, Dong Y B, Zhou H S, Zacharias W, McMasters K M (2005) SW-620 cells treated with topoisomerase I inhibitor SN-38: gene expression profiling. *J Transl Med* 3:44.

Steffenburg S, Gillberg C L, Steffenburg U, Kyllerman M (1996) Autism in Angelman syndrome: a population-based study. *Pediatr Neurol* 14:131-136.

Stewart C F, Zamboni W C, Crom W R, Gajjar A, Heideman R L, Furman W L, Meyer W H, Houghton P J, Pratt C B (1996) Topoisomerase I interactive drugs in children with cancer. *Invest New Drugs* 14:37-47.

Sutcliffe J S, Nakao M, Christian S, Orstavik K H, Tommerup N, Ledbetter D H, Beaudet A L (1994) Deletions of a differentially methylated CpG island at the SNRPN gene define a putative imprinting control region. *Nat Genet* 8:52-58.

Tilghman S M (1999) The sins of the fathers and mothers: genomic imprinting in mammalian development. *Cell* 96:185-193.

Trushina E, Du Charme J, Parisi J, McMurray C T (2006) Neurological abnormalities in caveolin-1 knock out mice. *Behav Brain Res* 172:24-32.

van Woerden G M, Harris K D, Hojjati M R, Gustin R M, Qiu S, de Avila Freire R, Jiang Y H, Elgersma Y, Weeber E J (2007) Rescue of neurological deficits in a mouse model for Angelman syndrome by reduction of alphaCaMKII inhibitory phosphorylation. *Nat Neurosci* 10:280-282.

Vassal G, Pondarre C, Boland I, Cappelli C, Santos A, Thomas C, Lucchi E, Imadalou K, Pein F, Morizet J, Gouyette A (1998) Preclinical development of camptothecin derivatives and clinical trials in pediatric oncology. *Biochimie* 80:271-280.

Wagstaff J, Chaillet J R, Lalande M (1991) The GABAA receptor beta 3 subunit gene: characterization of a human cDNA from chromosome 15q11q13 and mapping to a region of conserved synteny on mouse chromosome 7. *Genomics* 11:1071-1078.

Wang J C (2002) Cellular roles of DNA topoisomerases: a molecular perspective. *Nat Rev Mol Cell Biol* 3:430-440.

Wang X, Sun Q, McGrath S D, Mardis E R, Soloway P D, Clark A G (2008) Transcriptome-wide identification of novel imprinted genes in neonatal mouse brain. *PLoS One* 3:e3839.

Weeber E J, Jiang Y H, Elgersma Y, Varga A W, Carrasquillo Y, Brown S E, Christian J M, Mirnikjoo B, Silva A, Beaudet A L, Sweatt J D (2003) Derangements of hippocampal calcium/calmodulin-dependent protein kinase II in a mouse model for Angelman mental retardation syndrome. *J Neurosci* 23:2634-2644.

Williams C A (2005) Neurological aspects of the Angelman syndrome. *Brain Dev* 27:88-94, Yashiro K, Riday T T, Condon K H, Roberts A C, Bernardo D R, Prakash R, Weinberg R J, Ehlers M D, Philpot B D (2009) Ube3a is required for experience-dependent maturation of the neocortex. *Nature Neuroscience* 12:777-783.

Zhang J H, Chung T D, Oldenburg K R (1999) A Simple Statistical Parameter for Use in Evaluation and Validation of High Throughput Screening Assays. *J Biomol Screen* 4:67-73.

Zori R T, Hendrickson J, Woolven S, Whidden E M, Gray B, Williams C A (1992) Angelman syndrome: clinical profile. *J Child Neurol* 7:270-280.

Example 16

Angelman syndrome is a severe neurodevelopmental disorder caused by deletion or mutation of the maternal allele of the ubiquitin protein ligase E3A(Ube3a)[1-3]. In neurons, the paternal allele of Ube3a is intact but epigenetically silenced[4-6], raising the possibility that Angelman syndrome could be treated by activating this silenced allele to restore functional UBE3A protein[7,8]. Using an unbiased, high-content screen in primary cortical neurons from mice, twelve topoisomerase I inhibitors and four topoisomerase II inhibitors were identified that unsilence the paternal Ube3a allele. These drugs included topotecan, irinotecan, etoposide, and dexrazoxane (ICRF-187).

At nanomolar concentrations, topotecan upregulated catalytically active UBE3A in neurons from maternal Ube3a-null mice. Topotecan concomitantly down-regulated expression of the Ube3a antisense transcript that overlaps the paternal copy of Ube3a[9-11]. These results suggest that topotecan unsilences Ube3a in cis by reducing transcription of an imprinted antisense RNA. When administered in vivo, topotecan unsilenced the paternal Ube3a allele in several regions of the nervous system, including neurons in the hippocampus, neocortex, striatum, cerebellum and spinal cord. Paternal expression of Ube3a remained elevated for at least twelve weeks after cessation of topotecan treatment, suggesting transient topoisomerase inhibition has enduring effects on gene expression. These findings reveal a role for topoisomerase I and II enzymes in epigenetic gene regulation, and suggest a therapeutic strategy for reactivating the functional but dormant allele of Ube3a in patients with Angelman syndrome.

No effective therapies exist for Angelman syndrome (AS)—an imprinting disorder caused by mutations or deletions in the maternal allele of Ube3a[1-3]. Ube3a is biallelically expressed in most tissues of the body; however, in rodents and humans, most neurons express Ube3a only from the maternally-inherited allele[4,12-14]. This unique epigenetic pattern of regulation suggested that it might be possible to unsilence the dormant paternal Ube3a allele in neurons[7,8].

Figure 13A:
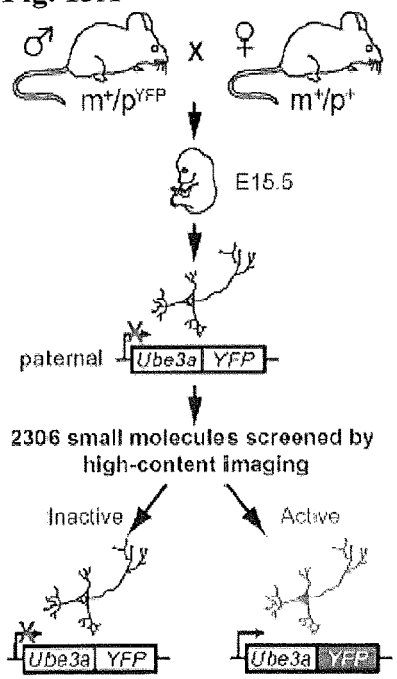
Figure 13B:
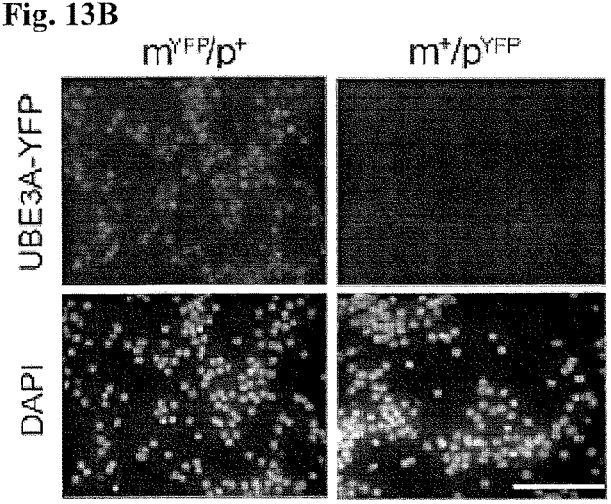
Figure 13C:
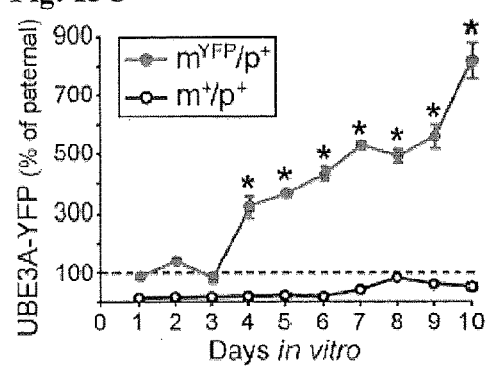

To test this possibility, a 384-well high-content screen was developed using primary mouse cortical neurons from Ube3a-Yellow Fluorescent Protein (Ube3a-YFP) knockin mice[15], to search for drug-like molecules that could unsilence the paternal Ube3a-YFP allele (FIG. 13A). This screen was based on the observation that the imprinting of Ube3a-YFP was maintained in vitro in cultured embryonic cortical neurons. Notably, Ube3a-YFP expression was undetectable (silenced) in cultured neurons when paternally inherited (Ube3a$^{m+/pYFP}$), but was expressed when maternally inherited (Ube3a$^{mYFP/p+}$) (FIG. 13B), with expression increasing from 4 to 10 days in vitro (DIV) (FIG. 13C). This significant difference between maternal and paternal UBE3A-YFP protein levels provided a large screening window and a Z'-factor score of 0.58 (determined by statistically comparing antibody-enhanced fluorescence intensities and variations between Maternal and paternal UBE3A-YFP signals at DIV 10), making this high-content platform suitable for unbiased screening.

Figure 16A:
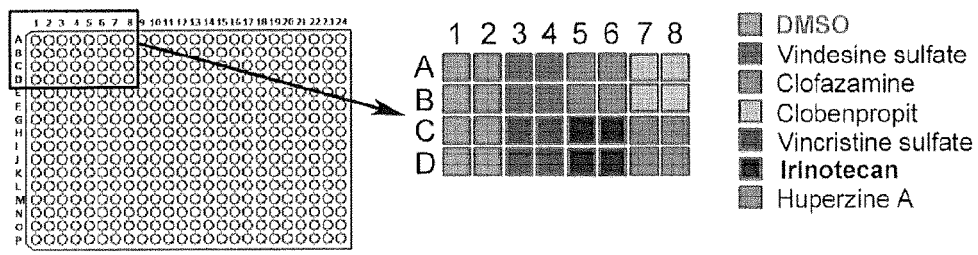
FIGS. 16A-D. Method for detecting paternal UBE3A-YFP protein in neurons using high-content screening microscopy. (A) Neurons from paternal Ube3a-YFP mice (m$^+$/p$^{YFP}$) were cultured in 384-well plates and treated with small molecules (10 μM) or vehicle (0.2% DMSO) in quadruplicate. Inset depicts drugs applied to a portion of the original 384-well plate used to identify irinotecan as an active. (B) Fluorescence for DAPI (nuclear marker) and UBE3A-YFP in the original plate used to identify irinotecan as an active. UBE3A-YFP protein signals were amplified using an anti-GFP antibody. Images show the zoomed inset outlined in (A). Blue box highlights vehicle control wells and red box highlights irinotecan-treated wells. (C) 4×4 montaged images of wells were obtained using the BD Pathway 855 microscope. This enabled fluorescence determination from >1200 individual neurons/well. Using custom written algorithms and Arrayscan software, neuronal nuclei were identified using the DAPI channel and detected objects (yellow circles) overlayed onto the UBE3A-YFP image (red circles). This enabled detection of nuclear UBE3A-YFP fluorescence intensity. Scale bars show 100 μm in montaged images (left) or 30 μm in zoomed images. (D) Quantitative results (mean±s.e.m.) from quadruplicate wells.
Figure 16B:
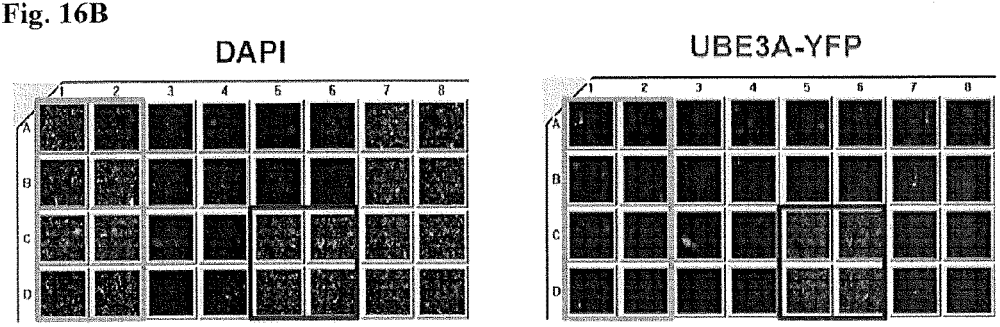
Figure 16C:
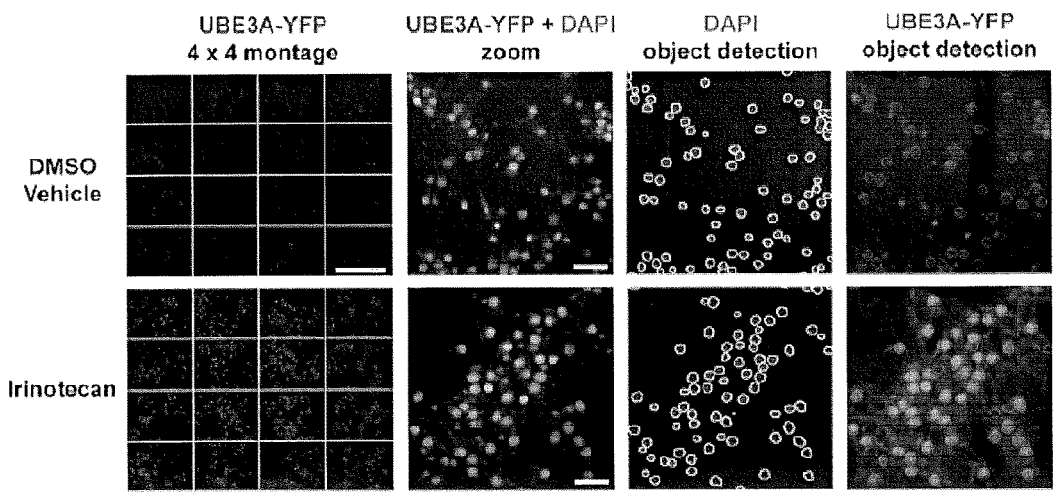
Figures 16D, 17:
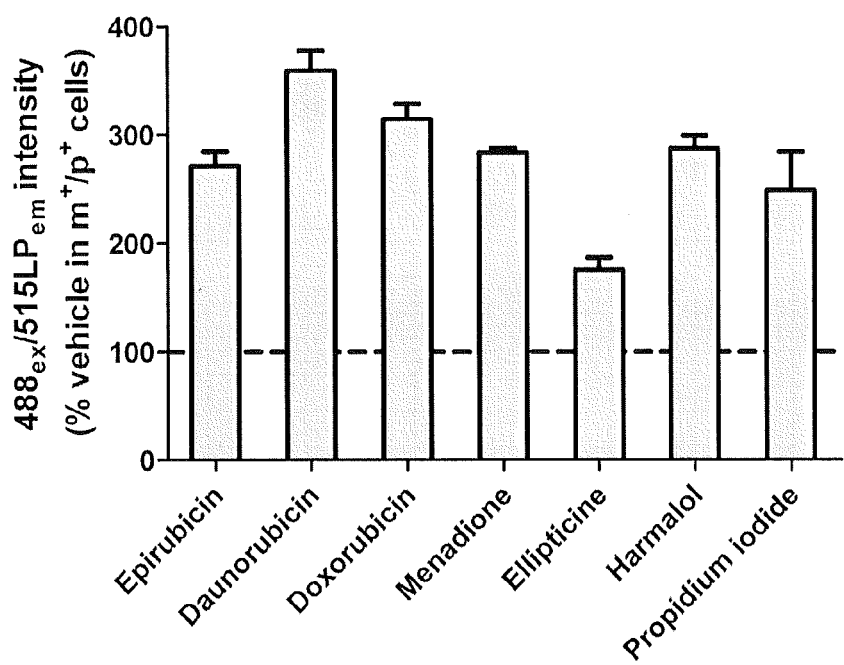
FIG. 17. Autofluorescent compounds. Potential hits, shown in FIG. 13D, were subsequently tested for inherent fluorescence. Wild-type (m$^+$/p$^+$) neurons were treated for 72 h with 10 μM of compounds followed by imaging to identify possible inherent fluorescence of compounds in the 488 excitation/515 longpass emission channel. Fluorescence detection from wild-type neurons demonstrates that the compounds shown in this bar graph exhibited high levels of intrinsic fluorescence in quadruplicate wells of cells, with similar results obtained in two independent experiments. Bars represent means s.e.m.
Figure 18:
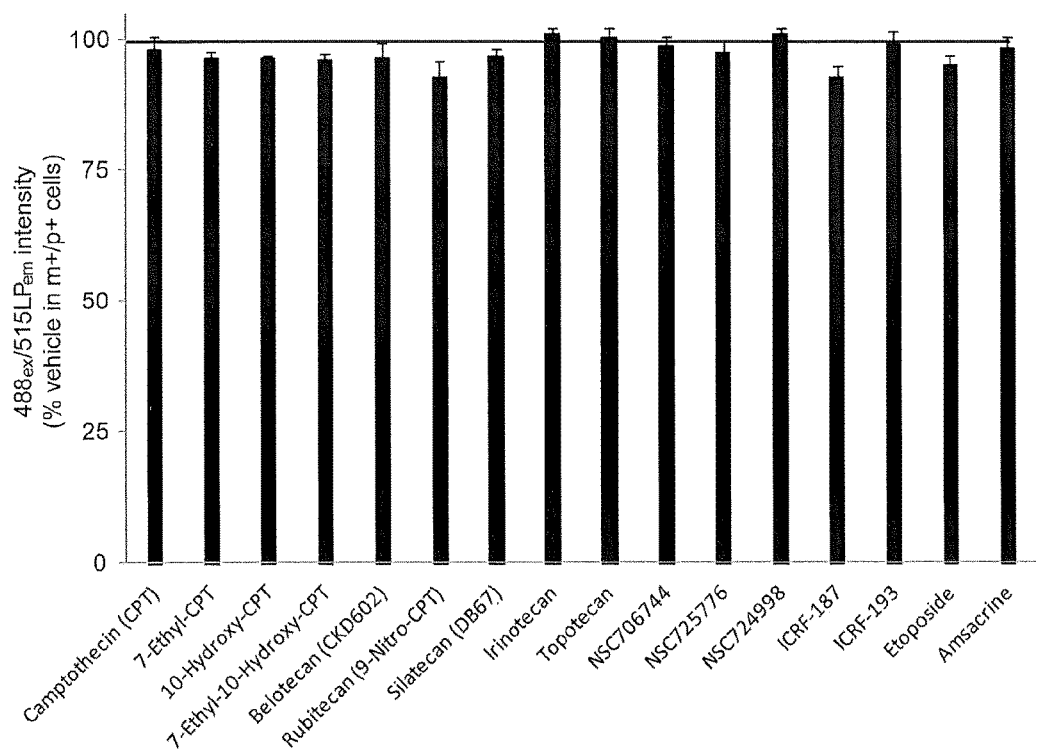
FIG. 18. Topoisomerase inhibitors that unsilence UBE3A-YFP do not exhibit inherent fluorescence. All topoisomerase type I and type II inhibitors that were classified as active in the primary screen were tested for inherent fluorescence in the high-content screen imaging assay. Wild-type (m$^+$/p$^+$) neurons were treated for 72 h with 10 μM of compounds followed by imaging. None of these active compounds increased fluorescence compared to vehicle-treated neurons. Results represent the mean±s.e.m. from four treated wells of neurons. Similar results were obtained in two independent experiments.
Figure 22C:
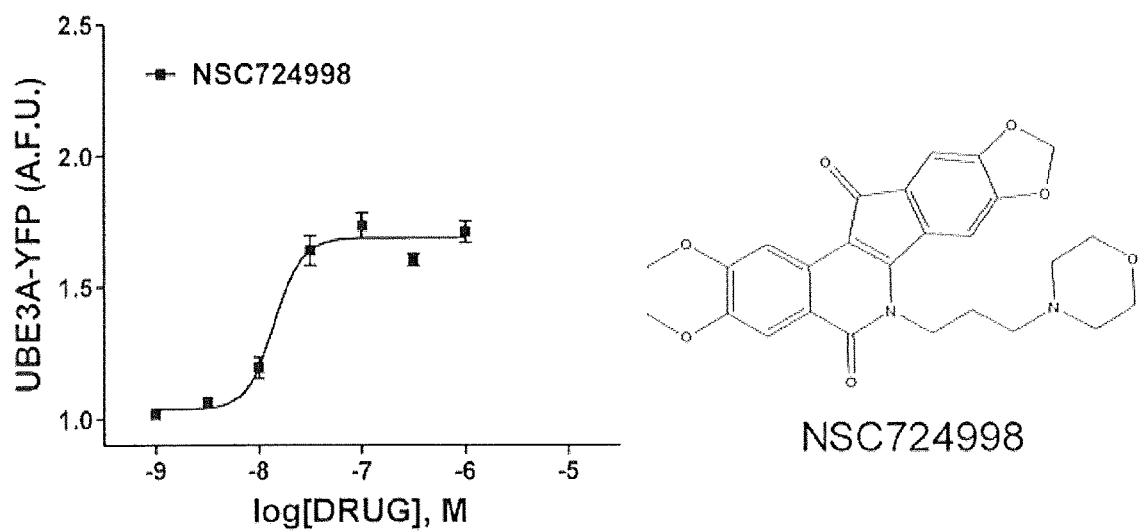

To perform the screen, Ube3a$^{m+/pYFP}$ neurons were cultured for 7 days and then these neurons were treated with compounds (10 μM for 72 hours) from multiple small molecule libraries enriched for central nervous system (CNS) actives and FDA-approved drugs (FIG. 13D, FIG. 19). In total, 2,306 small molecules were screened in quadruplicate, and values were normalized to vehicle-treatment (0.2% DMSO). While methylation and other epigenetic marks are thought to control imprinting of Ube3a[9,16-18], surprisingly, none of the commonly used compounds that target the epigenome, including chromatin remodeling drugs and DNA methyltransferase inhibitors, unsilenced the paternal Ube3a-YFP allele. A number of compounds were identified as false positives (gray compounds in FIG. 13D) due to their intrinsic fluorescence (FIG. 17). The initial screen identified one compound—irinotecan, an FDA-approved camptothecin-based topoisomerase type I inhibitor. Irinotecan lacked intrinsic fluorescence and upregulated UBE3A-YFP fluorescence (FIGS. 13D-E and FIG. 18). Irinotecan (10 μM) also upregulated paternal UBE3A-YFP protein (FIG. 13F) and endogenous UBE3A protein (FIG. 13G) in neuronal cultures from Ube3a$^{m+/pYFP}$ and Ube3a$^{m-/p+}$ mice (AS model mice[13]), respectively.

Figure 14A:
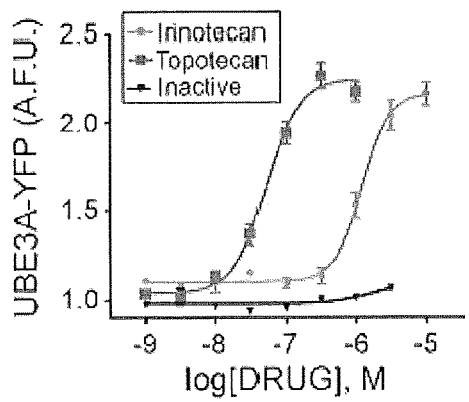
FIGS. 14A-I. Topotecan unsilences the paternal allele of Ube3a and the unsilenced protein is catalytically active. (A) Dose-response curves for unsilencing the paternal Ube3a-YFP allele. Inactive=lactam E ring-camptothecin. n=4/data point. (B) UBE3A-YFP levels in neurons from Ube3a$^{m+/pYFP}$ mice increase with duration of topotecan (300 nM) or irinotecan (1 µM) treatment. For topotecan treatment, one-way ANOVA, $F_{(5,32)}$=47.73, P<0.001; Bonferroni post hoc test after significant main effect, *P<0.01 compared to day zero; n=4-7/group. For irinotecan treatment, one-way ANOVA, $F_{(5,30)}$=12.17, P<0.001; Bonferroni post hoc test after significant main effect, *P<0.05 compared to day zero; n=4-8/group. A.F.U.=arbitrary fluorescence units. (C) Western blots and quantification of UBE3A and the loading control actin demonstrating that topotecan restores UBE3A levels in neurons from maternal Ube3a-deficient mice ($m^-/p^+$) to wild-type ($m^+/p^+$) levels. One-way ANOVA, $F_{(2,9)}$=8.28, P<0.01; Bonferroni post hoc test after significant main effect, *P<0.05; n=4/group. (D) Quantification of unbound TOP1 and representative Western blots. Note the decrease of unbound TOP1 after topotecan treatment in maternal Ube3a-deficient ($m^-/p^+$) neurons compared to vehicle-treated neurons ($m^-/p^+$ or $m^+/p^+$). β-tubulin was used as a loading control. One-way ANOVA, $F_{(2,6)}$=17.88, P<0.005; Bonferroni post hoc test after significant main effect, *P<0.05; n=3/group. (E) Western blot from vehicle- and topotecan-treated neurons from wild-type ($m^+/p^+$) and maternal Ube3a-deficient ($m^-/p^+$) mice. The higher molecular weight form representing ubiquitin-bound UBE3A is lost by treatment with the reducing agent DTT, which disrupts the UBE3A-thioester-ubiquitin bond. (F) Western blots examining UBE3A ubiquitin-thioester formation following immunoprecipitation with an anti-UBE3A antibody and in vitro ubiquitination in the presence or absence of the ubiquitin conjugating enzyme (E2), UBCH7. Note that UBE3A from wild-type ($m^+/p^+$) and topotecan-treated maternal Ube3a-deficient ($m^-/p^+$) neurons undergo a mobility shift in the presence of UBCH7 that is lost by addition of the reducing agent, DTT. All data are presented as means±s.e.m. (G) Schematic demonstrating location of 4 primer sets used to probe mRNA expression shown in (H). (H) Normalized mRNA levels in cultured Ube3a$^{m-/p+}$ neurons following vehicle or 300 nM topotecan. Expression is given as ratio of expression in drug treated cells to vehicle treated cells, normalized to the housekeeping gene RPL22. *P<0.05 compared to 0 hr, Kruskal-Wallis one-way ANOVA followed by post hoc tests, n=4-5 cultures/data point. (I) Schematic summarizing methylation status of the Snrpn promoter region on the maternal and paternal chromosome following treatment with vehicle or 300 nM topotecan (see complete primer 1 data set in FIG. 27). Average methylation status is indicated using a grayscale.
Figure 14B:
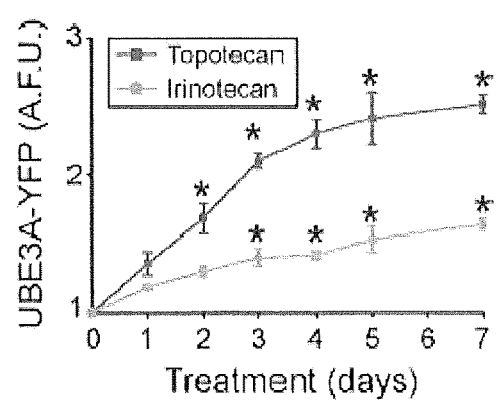
Figure 14C:
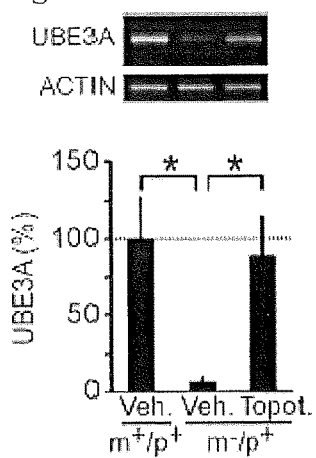
Figure 26A:
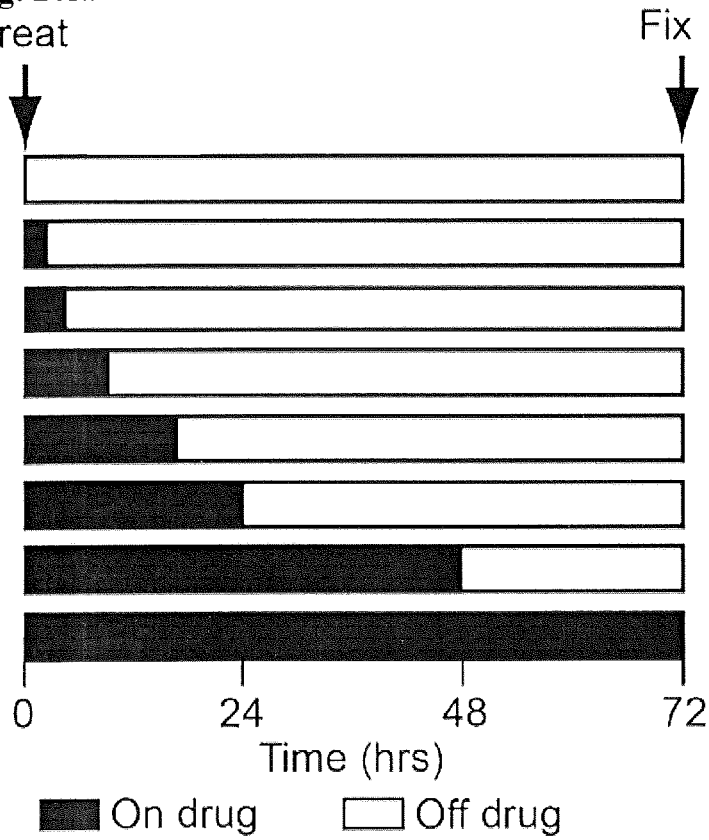
FIGS. 26A-B. The levels of paternal Ube3a unsilencing are proportional to the treatment time of topotecan. (A)
Figure 26B:
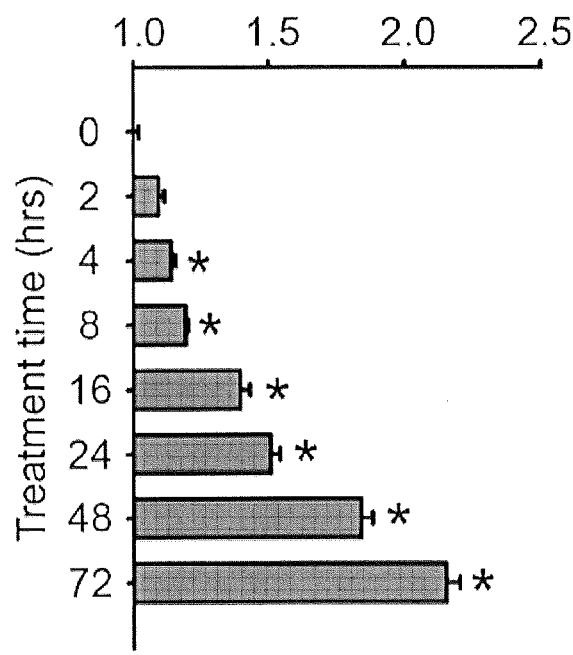

Many topoisomerase I inhibitors, including irinotecan and the related FDA-approved drug topotecan, are derived from the natural product camptothecin (CPT)[19]. To explore structure activity relationships, CPT analogs and other topoisomerase inhibitors were tested (FIG. 14A; FIGS. 19-25), all of which lack inherent fluorescence (FIG. 18). Irinotecan and topotecan were found to upregulate paternal UBE3A-YFP in a dose- and time-dependent manner in cultured neurons, with topotecan being 20× more potent than irinotecan (FIGS. 14A-B; FIG. 26). In contrast, an inactive analog of CPT (lactam E-ring-CPT) that does not inhibit topoisomerases[20] failed to unsilence the paternal Ube3a-YFP allele (FIG. 14A; FIG. 19). Ten additional topoisomerase I inhibitors unsilenced Ube3a-YFP in a dose-dependent manner, including CPT analogs and structurally distinct indenoisoquinolines (Table 3 and FIGS. 19-22). In addition, structurally distinct topoisomerase II inhibitors (etoposide, dexrazoxane, ICRF-193, and amsacrine) also unsilenced the paternal Ube3a-YFP allele (Table 3 and FIGS. 23-25). The remaining studies were focused on the topoisomerase I inhibitor topotecan because it is approved for use in humans, it unsilenced Ube3a in the low nanomolar range, and topotecan (300 nM, 72 h) restored UBE3A protein to wild-type levels in cultured neurons from Ube3a$^{m-/p+}$ mice (FIG. 14C).

Figure 14D:
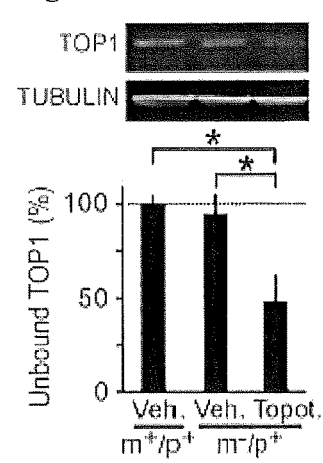

Many topoisomerase inhibitors, including topotecan, covalently link topoisomerases to DNA, forming stable DNA-enzyme complexes that are separable from free topoisomerase enzymes[19]. Since topotecan inhibits topoisomerase I (TOP1) and Top1 is expressed at high levels in the developing and adult brain[19,21], a subsequent analysis was focused on this enzyme. Topotecan (300 nM, 72 h) was found to significantly reduce the amount of free TOP1 (FIG. 14D) in cultured neurons, indicating that topotecan engages its known molecular target at doses that unsilence the paternal Ube3a allele. These data with 16 topoisomerase inhibitors and one inactive analog strongly suggest that inhibition of topoisomerase I or II can unsilence the paternal Ube3a allele.

Figure 14E:
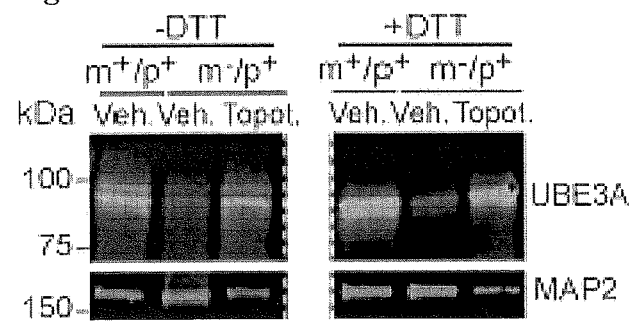

UBE3A is a HECT (homology to E6 carboxyl terminus) domain E3 ligase that forms a thioester-ubiquitin intermediate in the presence of E1 and E2 enzymes[22]. This thioester-ubiquitin intermediate is required for HECT domain E3 lipases to mono- and polyubiquitinate their substrates[23]. Interestingly, it was noted that topotecan (300 nM, 72 hr) upregulated UBE3A protein in Ube3a$^{m-/p+}$ cultures along with a higher molecular weight form (resolved after running gels for longer times; FIG. 14E). This high molecular weight band was also seen in wild-type (Ube3a$^{m+/p+}$) cultures and was lost upon addition of the reducing agent dithiothreitol (DTT) (FIG. 14E). These data suggest that the unsilenced paternal copy of UBE3A is catalytically active and competent to form a thioester-ubiquitin intermediate, just like wild-type, maternal-derived UBE3A[23].

Figure 14F:
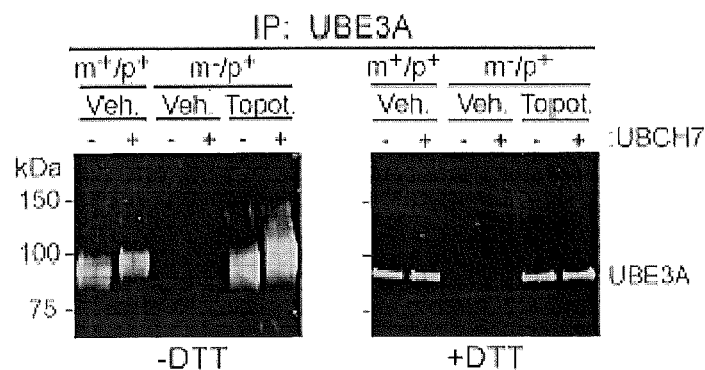

To further demonstrate that UBE3A was catalytically active, UBE3A was immunoprecipitated from cultured wild-type and Ube3a$^{m-/p+}$ neurons (+/− topotecan), then these samples were tested for a gel-mobility-shift in the presence or absence of the ubiquitin E2 UBCH7[24]. Both wild-type (maternal-derived) and topotecan-unsilenced (paternal-derived) UBE3A underwent mobility shifts in the presence of UBCH7 plus free ubiquitin that were abolished by DTT (FIG. 14F). This observation indicates the mobility shift was due to addition of covalent ubiquitin, and demonstrates that topotecan can upregulate a functional UBE3A enzyme.

Figure 14G:
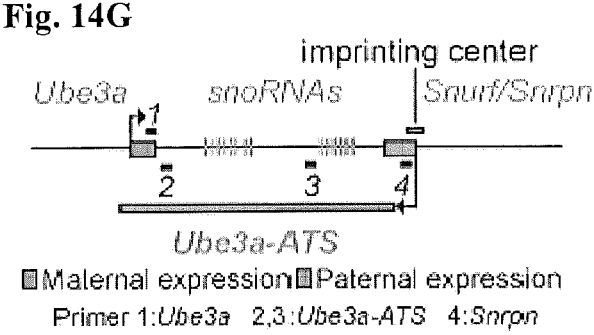
Figure 14H:
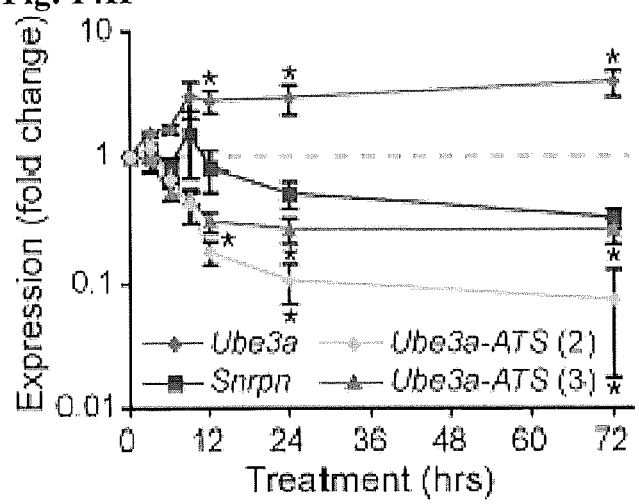
Figure 14I:
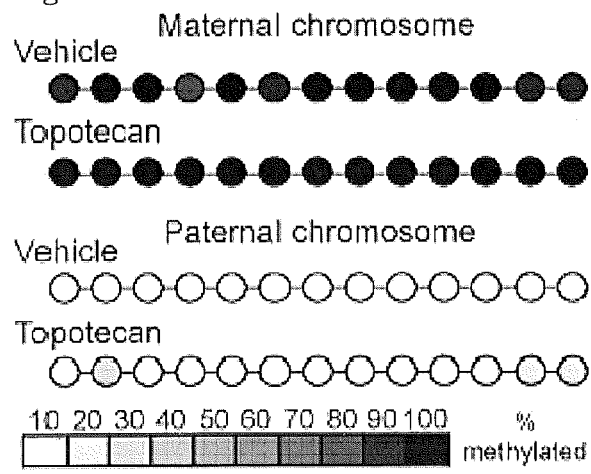

Ube3a is repressed in cis by a large antisense transcript (Ube3a-ATS) that overlaps the paternal allele of Ube3a (FIG. 14G)[9,10]. Ube3a-ATS is expressed exclusively from the paternal allele as a result of allele-specific methylation of an imprinting center that overlaps the Ube3a-ATS and Snurf/Snrpn transcription start site[25]. Studies were next carried out to determine if topotecan regulated Ube3a expression through changes in Ube3a-ATS expression or imprinting center methylation. Remarkably, topotecan upregulated expression of Ube3a in cultured neurons from Ube3a$^{m-/p+}$ mice while concomitantly downregulating expression of Ube3a-ATS and Snrpn (FIG. 14H). However, topotecan did not alter methylation at the imprinting center (FIG. 14I, FIG. 27). Taken together, these data suggest that topotecan unsilences paternal Ube3a by reducing transcription of a regulatory antisense RNA without appreciably affecting genomic methylation at the imprinting center.

Studies were then conducted to determine if topotecan could unsilence the paternal Ube3a allele in vivo. First, a dose was identified that was well tolerated, meaning there were no significant decreases in body weight between the beginning and end of the drug treatments (FIG. 28). Topotecan (3.74 μg/h) was then administered unilaterally into the lateral ventricle of Ube3a$^{m+/pYFP}$ or Ube3a$^{m-/p+}$ mice by intracerebroventricular (i.c.v.) infusion for two weeks using delivery by mini-osmotic pump, and the mice were sacrificed either immediately or 5 hr after drug cessation. Strikingly, topotecan unsilenced paternal Ube3a in the hippocampus, striatum, and cerebral cortex of the infused hemisphere, but had only a modest effect on the contralateral (non-infused) hemisphere with no effect in the cerebellum (FIGS. 15A-E, FIGS. 29-30). Pharmacokinetic analyses demonstrated that a significant amount of topotecan was detectable in the infused hemisphere immediately following treatment whereas low levels were present in the contralateral (non-infused) hemisphere and in cerebellum (FIG. 3A, FIG. 29). However, a higher dose of topotecan (21.6 μg/h for five days) did unsilence the paternal allele of Ube3a in Purkinje neurons of the cerebellum (FIG. 31). No significant difference in topotecan levels was detected in blood between drug- and vehicle-treated mice (data not shown). Topotecan concentrations significantly declined five hours after cessation of i.c.v. drug delivery (FIG. 15A), indicating that topotecan does not persist and is rapidly removed/metabolized in the brain. Together, these pharmacokinetic and pharmacodynamic data suggest that the degree to which topotecan unsilences the paternal Ube3a allele is directly correlated with drug concentrations in the brain. Moreover, these data indicate topotecan has the potential to unsilence the paternal Ube3a allele throughout the nervous system.

Figure 15A:
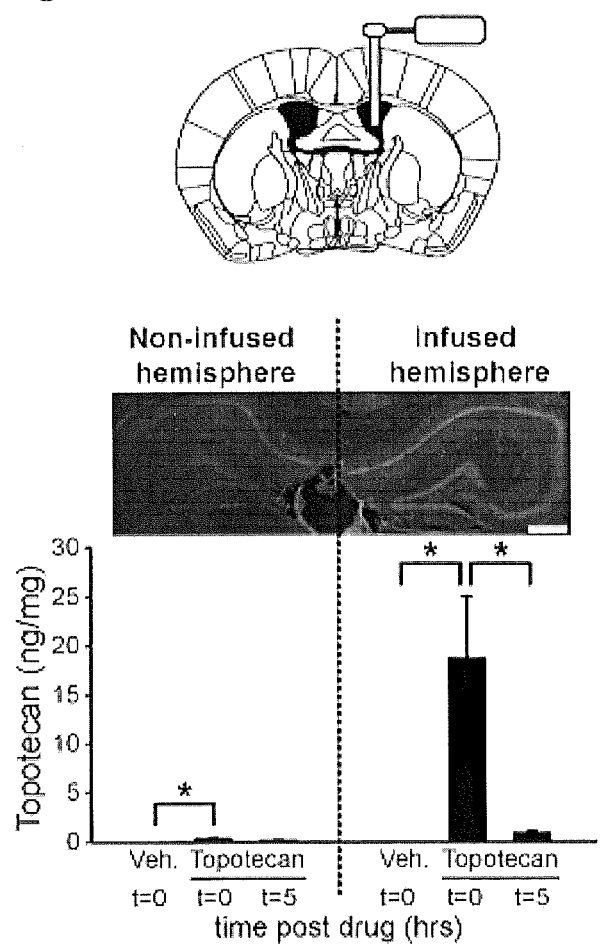
FIGS. 15A-H. Topotecan enduringly unsilences the paternal allele of Ube3a in vivo. (A) Schematic depicts unilateral delivery of topotecan (i.c.v.) using a mini-osmotic pump into the lateral ventricle of Ube3a$^{m+/pYFP}$ mice in vivo. Two weeks of topotecan infusion (3.74 μg/h) unsilenced the paternal Ube3a-YFP allele in the hippocampus of the infused hemisphere near the site of drug delivery, while only modestly unsilencing Ube3a-YFP in the contralateral (non-infused) hemisphere. Scale bar=500 μm. Pharmacokinetic analyses measuring topotecan levels in the infused and non-infused hemisphere immediately (t=0) or five hours (t=5) after cessation of drug delivery. For the infused hemisphere, one-way ANOVA, $F_{(2,20)}$=38.16, P<0.001, Bonferroni post hoc test, *P<0.01, n=5-9/group. For the non-infused hemisphere, one-way ANOVA, *P<0.05, n=6-9/group. (B) Representative sections and (C) quantification of optical intensity of UBE3A-YFP in hippocampal regions (CA1, CA2/3, and dentate gyrus=DG) of the topotecan-infused hemisphere or the hemisphere of vehicle-treated mice. *P<0.05, Mann-Whitney Rank Sum Test, n=5/group. (D) Representative sections and (E) quantification of paternal UBE3A-YFP in the striatum following i.c.v. infusion of topotecan. *P<0.05, two-tailed t test, n=4/group. (F) Schematic depicting schedule for i.t. delivery of topotecan (50 nmol/day for 10 of 14 days) and endpoints (arrows) immediately, 4 weeks, and 12 weeks after cessation of drug treatments. (G,H) Topotecan (i.t.) increased the number of UBE3A-YFP-positive spinal neurons compared to vehicle, and the unsilencing of Ube3a-YFP was maintained for at least 12 weeks. One-Way ANOVA, $F_{(5,41)}$=34.00, P<0.001; Bonferroni post hoc test after significant main effect, *P<0.001, n=7-8/group.
Figure 15B:
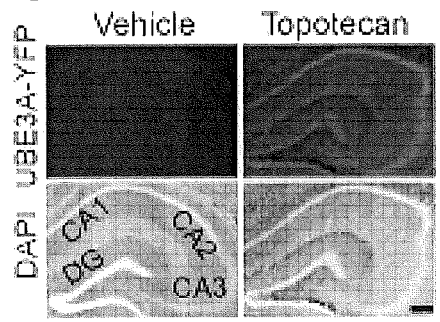
Figure 15C:
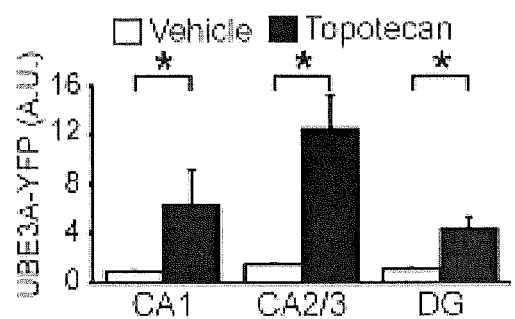
Figure 15D:
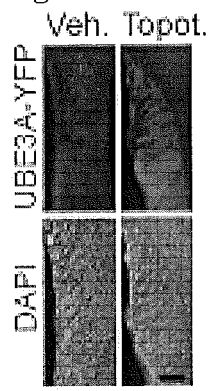
Figure 15E:
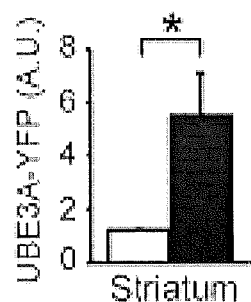
Figure 15F:
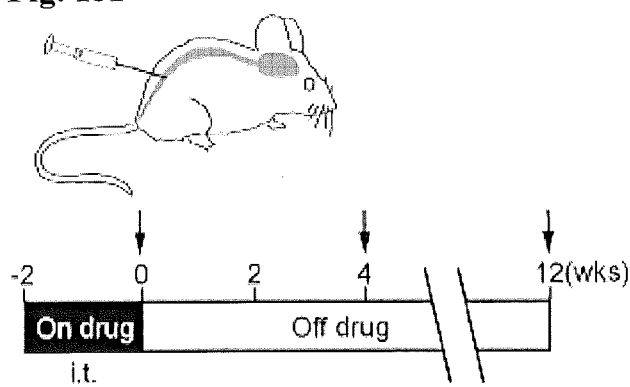
Figure 15G:
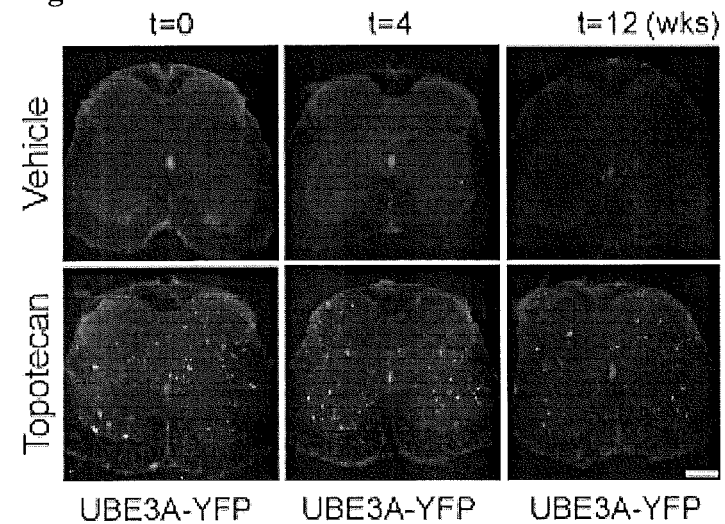
Figure 15H:
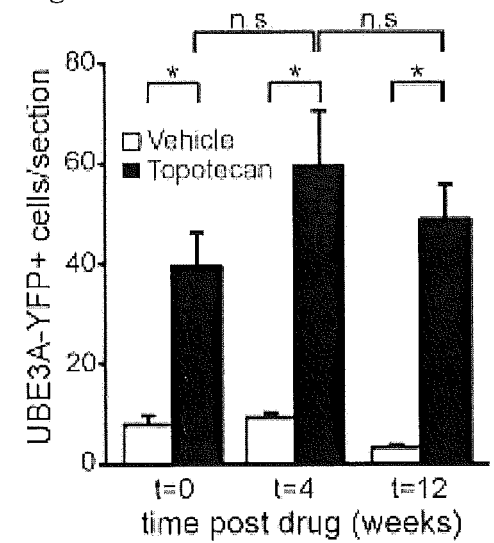

Genomic imprinting is thought to be established only during prescribed germline and embryonic periods of development and imprinted genes typically remain epigenetically regulated throughout life[26]. Thus, it was next sought to determine if topotecan had transient or long-lasting effects on paternal Ube3a expression. To test this possibility, an intrathecal (i.t.) delivery protocol was employed (FIG. 15F) since topotecan (FIG. 15G) and irinotecan (not shown) unsilenced paternal Ube3a in a sparse population of lumbar spinal neurons, allowing the quantification of all UBE3A-YFP-positive neurons. Moreover, i.t. delivery has been used to deliver topotecan to the brain in humans[27]. It was found that topotecan (50 nmol/5 μL i.t. once daily, for 10 of 14 days) was well tolerated (FIG. 28) and significantly increased the number of paternal UBE3A-YFP-positive cells in the lumbar spinal cord of mice (FIGS. 15G-H; FIG. 32A). The vast majority (>93%) of these UBE3A-YFP-positive cells were NeuN$^+$ neurons (FIGS. 32A-B), indicating topotecan unsilences Ube3a primarily in neurons in vivo. Moreover, the unsilenced paternal UBE3A-YFP protein was expressed at levels comparable to maternal UBE3A-YFP controls (FIG. 32C). Remarkably, the number of UBE3A-YFP-positive neurons remained elevated 12 weeks following cessation of drug treatment (FIGS. 15G-H), much longer than the elimination of topotecan from tissue (FIG. 15A). These results indicate that topotecan can enduringly unsilence paternal Ube3a in a subset of spinal neurons and suggest that a single course of drug treatment has the capacity to permanently modify expression of Ube3a.

The discovery that topoisomerase inhibitors unsilence the paternal Ube3a allele in neurons represents demonstrates that a small molecule drug can unsilence a monoallelically expressed gene. Ube3a expression is modestly upregulated in the brain of Top2b knockout mice[28], providing genetic support that topoisomerases regulate Ube3a expression. It was found that the unsilenced paternal allele of UBE3A is functional, suggesting that drug treatments could rescue molecular, cellular, and behavioral deficits associated with loss of UBE3A[7,13,29]. Topotecan and irinotecan are approved for use in patients with cancer, are well-tolerated when administered chronically in adult and pediatric patients, and penetrate into the central nervous system[27,30]. Thus, this study raises the possibility that topoisomerase inhibitors could be used to treat symptoms associated with AS and suggests that topoisomerase inhibitors regulate gene expression through a transcriptional mechanism.

Methodology Details

All animal procedures were approved by the University of North Carolina at Chapel Hill Animal Care and Use Committee. Ube3a-YFP knockin mice[15], Ube3a$^{m-/p+}$ mice[13] and their age-matched, wild-type controls were used. High-content screening was performed on a BD Pathway 855 system. UBE3A-YFP was detected for drug screening with an anti-GFP antibody (Novus Biologicals, NB600-308; 1:1000) because intrinsic YFP fluorescence levels were low in cultured neurons and tissue sections. All data are presented as mean±s.e.m., with sample sizes (n) shown in figures or stated in text. Statistical analyses were performed using SigmaPlot 11 (Systat Software). Normality tests (Shapiro-Wilk) and equal variance tests were run and passed (P>0.05) before parametric statistical analyses were run.

Mice.

Ube3a-YFP mice were generated and provided by the laboratory of Dr. Art Beaudet[15]. Ube3a-deficient mice were generated in the laboratory of Dr. Art Beaudet[13] and backcrossed by Dr. Yong-hui Jiang onto a C57BL/6J background. C57BL/6 mice (Charles River Laboratories) were used for matings with Ube3a-YFP, and C57BL/6J mice (Jackson Laboratories) were used for matings with Ube3a-deficient mice and CAST/EiJ mice (Jackson Laboratories).

Primary Neuron Cultures.

Embryonic day (E) 13.5 to E16.5 mouse cortices were dissected and trypsinized with TrypLE express at 37° C. for 10 min. Dissociated neurons were seeded onto 384-well plates coated with poly-D-lysine (0.1 mg/ml) at a density of $2 \times 10^4$ cells/well (or at a density of $1.8 \times 10^6$ cells/well for six-well plates). Neurons were cultured with Neurobasal medium with 5% fetal bovine serum, GlutaMax (Invitrogen, #35050-061), B27 (Invitrogen, #17504-044) and Antibiotic-Antimycotic (Invitrogen, #15240-062) and changed into Neurobasal medium supplemented with 4.84 μg/ml Uridine 5'-triphosphate (Sigma, U6625), 2.46 μg/ml 5 fluoro 2-deoxyuridine (Sigma, F0503), GlutaMax (Invitrogen, #35050-061), B27 (Invitrogen, #17504-044), and Antibiotic-Antimycotic (Invitrogen, #15240-062) at days in vitro (DIV) 1 and DIV5.

Drug Libraries and Compounds.

Multiple drug libraries were used for the screening campaign including the NIMH X-901 Library (source: National Institutes of Health Chemical Synthesis and Drug Supply Program); the NIH Clinical Collection (source: National Institutes of Health), the Prestwick Library (source: Prestwick Chemical), an internal Roth laboratory library comprised mainly of central nervous system active small molecules (source: National Institute of Mental Health Psychoactive Drug Screening Program), a small molecule library of DNA methyltransferase inhibitors, protein lysine methyltransferase inhibitors and other small-molecule modulators of epigenetic targets (source: Center for Integrative Chemical Biology and Drug Discovery, UNC-CH). Suberoylanilidehydroxamic acid (SAHA) was purchased from Cayman Chemical. Irinotecan, zebularine, hydralazine, procainamide, 5-aza-2'-deoxycytidine (decitabine), etoposide, tenoposide, amsacrine, and ICRF-193 were all obtained from Sigma-Aldrich. Topotecan, camptothecin (CPT), 10-hydroxy-CPT, 7-ethyl-CPT, and 7-ethyl-10-hydroxy-CPT (SN38) were obtained from MOLCAN Corporation. ICRF-187 was provided by the National Cancer Institute's Developmental Therapeutics Program. Belotecan, silatecan and rubitecan were provided by Dr. William Zamboni (UNC Eshelman School of Pharmacy). The indenoisoquinoline derivatives NSC706744, NSC725776, and NSC724998 were synthesized as described[32,33]. The inactive lactam E ring CPT analog was synthesized as described[20].

High-Content Screening Microscopy and Small Molecule Screening.

Primary cortical neurons were isolated from E13.5-16.5 Ube3a-YFP mice. Screening was performed in quadruplicate at DIV7 using multiple chemical libraries and a compound concentration of 10 μM in 0.2% DMSO vehicle. After 72 h of drug exposure, neurons were fixed with 4% paraformaldehyde in PBS for 35 min, permeabilized with 0.3% Triton X-100 in PBS on ice for 30 min, and blocked by 5% goat serum with 0.1% Triton X-100 in PBS at room temperature for 1 hr. Cells were incubated with a rabbit polyclonal antibody to GFP (1:1000, Novus Biologicals, NB600-308) at room temperature for 1 hr and then incubated with Alexa Fluor 488 goat antibody to rabbit IgG (1:200, Invitrogen, A11008) and DAPI (1:10,000, Invitrogen, D-1306) at room temperature for 30 min. Individual wells of immunofluorescence-processed plates were imaged for DAPI or Alexa 488 fluorescence using the BD Pathway 855 high-content imaging microscope with a 488 excitation/515 long pass filter. Antibody-enhanced UBE3A-YFP fluorescence intensities were determined from individual neurons in drug-treated wells and normalized to neurons in wells treated with 0.2% DMSO (vehicle control). Analyses were performed with custom macros and algorithms using NIH Image J and Arrayscan Cell Profiler software programs (Thermo Scientific/Cellomics). These image analyses enabled masking of nuclei in individual neurons and determination of UBE3A-YFP fluorescence intensities in the nuclei of individual neurons (FIG. 16). Drug-induced increases of >50% were initially binned as screening 'hits' if (1) the increases were consistently observed across replicate wells and (2) no apparent toxicities were observed by assessing nuclear structure of neurons co-stained with DAPI. Effective 'hit' compounds were validated in formal dose-response experiments to determine relative compound potencies ($EC_{50}$) and efficacies ($E_{max}$).

After the initial identification of irinotecan as an active, other topoisomerase inhibitors were screened. DIV7 primary neurons from Ube3a$^{m+/pYFP}$ mice were dose-treated for 72 h with topoisomerase I and II inhibitors in ten point dose-responses in full and half log molar concentrations (1 nM to 30 μM). Neurons were fixed, processed for immunofluorescence, and UBE3A-YFP fluorescence intensities were again determined by high-content imaging microscopy. The dose response results were analyzed by least squares sigmoidal dose-response curve fitting models using Graphpad Prism 5.0 (Graphpad Software, Inc.). The calculated $EC_{50}$ values (potencies) and Y-value top plateau (estimated efficacies or $E_{max}$) enabled comparative analyses of the relative potency and efficacy of the identified compounds. To control for potential false positive 'hit' compounds, cortical neurons from wild-type mice, which lack Ube3a-YFP, were also treated to determine if 'hit' compounds exhibit inherent fluorescence.

A Z'-factor score was determined to assess the appropriateness of the screening platform by comparing UBE3A-YFP maternal and paternal fluorescence signals at DIV10. This was done by determining the mean cellular UBE3A-YFP fluorescence of >1200 neurons in quadruplicate wells for both genotypes which were normalized to age-matched vehicle control treated wells. The score was calculated using the following formula: Z' factor=1−((3×(SD Maternal UBE3A-YFP+SD Paternal UBE3A-YFP))/(Mean Maternal UBE3A-YFP−Mean Paternal UBE3A-YFP); where SD is the standard deviation.

Immunofluorescence Staining in CNS Tissues.

For immunocytochemistry in brain tissues, mice were perfused with 4% PFA in 0.1M PBS, postfixed overnight, and cryoprotected with 20% sucrose in 0.1M phosphate buffer (PB), pH=7.4 for two days. 60 μm sections were collected and permeabilized with 0.3% Triton X-100 in 0.1M PB for 30 min, and blocked by 5% goat serum for 1 hr. Sections were incubated with rabbit polyclonal antibody to GFP (1:1000, Novus Biologicals, NB600-308) at 4° C. overnight and then incubated with Alexa Fluor 488 goat antibody to rabbit IgG and DAPI for 2 hr at room temperature. Images were acquired using a Zeiss LSM 510 and 710 confocal microscopes.

For immunocytochemistry in spinal cord, lumbosacral spinal cord (approximately L1 to S2 and inclusive of the area corresponding to intrathecal injection site) was removed from each mouse and immersion-fixed for 8 h in cold 4% paraformaldehyde/0.1M phosphate buffer (pH 7.4). After a period of cryoprotection in 30% sucrose in 0.1M phosphate buffer, each spinal cord was sectioned on a cryostat at 40 μm. Sections to be stained immediately were collected in PBS; sections to be saved for future study were placed in a PBS/ethylene glycol/glycerol solution and stored at −20° C. Every fourth section was incubated overnight in a mixture containing a chicken IgY to GFP (1:750; Ayes Labs, GFP-1020) and a mouse $IgG_1$ to NeuN (1:250; Millipore, MAB377) and treated the following day with a cocktail containing goat anti-chicken IgY-Alexa 488 (1:200; Invitrogen, A-11039), goat anti-mouse IgG1-Alexa 568 (1:200; Invitrogen, A-21124), and DRAQ5 (1:10,000; Axxora, BOS-889-001). Immunostained sections were mounted from PBS onto SuperFrostPlus Slides (Fisher), which were then air-dried briefly, rehydrated with PBS, and coverslipped with FluoroGel (Electron Microscopy Sciences). For quantification studies, sections were imaged using a Nikon Eclipse 80i with Surveyor mosaic imaging software. For qualitative assessment, sections were imaged as maximal projections on a Zeiss LSM 510.

Optical Intensity Measurement of UBE3A-YFP in Brain Tissue and Cell Counting of UBE3A-YFP-Positive Neurons in Spinal Cord.

For optical intensity measurement in selected brain regions, sections were imaged using a Zeiss LSM 510 confocal microscope. With custom macros created using ImageJ software[34], optical intensity of UBE3A-YFP was measured in different regions of hippocampus and striatum from vehicle- and topotecan-treated mice. Image intensity levels were normalized to background intensities from appropriate regions in vehicle-treated mice. Brain sections between Bregma −1.22 mm and −2.06 mm were chosen for analysis (n=5 sections/mouse for hippocampus and n=3 to 5 sections/mouse for striatum).

For cell counting in spinal cord, 14 to 18 sections per mouse in segments corresponding to the injection site were analyzed. Slices were imaged using a Nikon Eclipse 80i microscope equipped with a QimagingRetigaExi high-speed CCD camera system and Surveyor mosaic imaging software using a 10× objective. For qualitative purposes, selected sections were also imaged on a Zeiss LSM 510 confocal microscope. Cells were counted manually by individuals blind to the experimental groups from raw (unprocessed) images using ImageJ and Cellprofiler[35] software.

YFP intensity levels from confocal XYZ image stacks were measured using a semi-automated macro with ImageJ. Individual YFP-positive cells were selected by eye, the criteria being the Z plane having the largest area for each cell. Cell regions were defined by intensity thresholding or manual tracing and the average YFP intensity and percent saturation were calculated for each cell.

Western Blotting.

E13.5-15.5 primary cortical neurons from Ube3a-YFP, Ube3a-deficient, or wild-type mice were plated in 6-well plates. At DIV7, neurons were treated with drug or 0.1% DMSO for 72 h, and then total protein lysates were obtained by lysis buffer (1% Triton X-100, 5 mM EDTA, 0.15M NaCl, 10 mM Tris-HCl, pH 7.5, phosphatase inhibitor cocktails 1, protease inhibitor cocktail). To assess UBE3A-YFP or UBE3A protein levels, 7.5 μg of total protein lysates from Ube3a-YFP or Ube3a-deficient neurons were separated by 8% SDS-polyacrylamide gel electrophoresis. Proteins were then transferred to nitrocellulose membranes, and immunoblotting was performed using a rabbit anti-GFP antibody (Novus, 1:500) and Alexa Fluor 680 goat anti-rabbit IgG (Invitrogen, 1:5000) or rabbit anti-UBE3A antibody (Abcam, 1:500) and Alexa Fluor 680 goat anti-rabbit IgG (Invitrogen, 1:5000). UBE3A-YFP or native UBE3A protein bands were visualized by an Odyssey system (LI-COR Biosciences). To control for protein loading, UBE3A-YFP or UBE3A protein levels were normalized to actin levels detected in each sample.

Ubiquitin Thioester Assay.

DIV10 cortical neurons were harvested and lysed in immunoprecipitation buffer (20 mM Tris-HCl, 3 mM EDTA, 3 mM EGTA, 150 mM NaCl, 1% Triton X-100, pH 7.4) containing 10 mM sodium fluoride, 1.0 mM sodium orthovanadate, 1.0 µg/mL aprotinin, and 0.1 mM DTT. UBE3A protein was immunoprecipitated from cell extracts with 5.0 µg of an anti-UBE3A antibody (Bethyl Laboratories) overnight at 4° C. and then washed 2 times with IP buffer containing 500 mM NaCl, followed by ubiquitin buffer (50 mM Tris, 5 mM $MgCl_2$, pH 7.6). For in vitro ubiquitination of immunoprecipitated UBE3A, UBE3A was mixed with 0.1 µg E1, 0.5 µg UBCH7, 2.5 µg ubiquitin (Boston Biochem) and 10 mM ATP in a total reaction volume of 20 µL. The reaction was incubated at room temperature for 10 min and end products were stopped in 2×SDS sample buffer with or without DTT. Samples were boiled, separated by SDS PAGE gel electrophoresis, transferred to PVDF membrane, and immunoblotted with an anti-UBE3A or anti-ubiquitin (Santa Cruz) antibody.

Topoisomerase Depletion Assay.

DIV7 cortical neurons were treated with 300 nM topotecan or vehicle for 72 h. Cells were harvested and lysed on ice for 30 min in RIPA buffer (50 mM Tris-HCl, 150 mM NaCl, 1% Triton X-100, 0.5% sodium deoxycholate, 0.1% SDS, pH 7.4) to preserve topoisomerase cleavable complexes. Cell extracts were then centrifuged at 14,000 rpm at 4° C. to pellet insoluble debris. 30 µg of the cell supernatant was diluted in 2×SDS sample buffer and separated on a 7.5% SDS-PAGE gel, transferred to PVDF membrane, and immunoblotted with an anti-Topoisomerase I antibody (Santa Cruz) to detect free Topoisomerase I. An anti-β-Tubulin (Sigma) antibody was used as a loading control.

Quantitative PCR.

For quantitative reverse transcriptase polymerase chain reaction (qRT-PCR) analysis, total RNA was extracted from cortical cultures treated with 300 nM topotecan using Trizol reagent (Invitrogen). First strand cDNA synthesis was performed on 500 ng-2 µg total RNA using Superscript III reverse transcriptase (Invitrogen) primed with random hexamers. qPCR reactions used SYBR green (Invitrogen) and were run on a Rotorgene 3000 (Corbett Research). Standard curves and Ct values were generated using Rotorgene analysis software version 6.0. Expression of Ube3a, Ube3a-ATS, Ipw and Snrpn were determined after normalization of each cDNA sample to expression levels of the housekeeping genes Rpl22 and Actb. Primers used were as shown in Table 4.

Bisulfite Sequencing.

Genomic DNA was extracted from cortical cultures treated with 300 nM topotecan using Trizol reagent. Bisulfite conversion was performed on 200 ng genomic DNA using the MethylCode kit (Invitrogen). 1 µL of converted DNA was used as template for PCR. A first round of PCR was performed as described in Peery et al. using the W18 (5'-GTAGTAGGAATGTTTAAGTATTTTTTTTGG) and W19 (5'-CCAATTCT-CAAAAATAAAAATATCTAAATT) or W16 (5'-AATTTA-GATATTTTTATTTTTGAGAATTGG) and W17 (5'-TCTA-CAAATCCCTACAACAACAACAA) primer sets[38]. A second semi-nested round of PCR was performed using 1 µL of the primary PCR reaction as template. For semi-nested PCR, the W18 primer was used with the nested W19-inside primer (5'-AAATAAAATACACTTTCACTACTAAAATC), or the W16 primer was used with the nested W17-inside primer (5'-ACAACAAAACTTCTATCCACAC). Products were separated on an agarose gel and extracted using the Qiaquick gel extraction kit (Qiagen). Purified DNA was ligated into the pGem-T Easy vector (Promega). Individual clones were amplified and sequenced.

Intrathecal Injection.

Topotecan (50 nmol in 5 unless noted) was injected into unanesthetized mice via a 30-gauge needle attached to a 50 µL Luer-hub Hamilton syringe using the direct lumbar puncture method[39]; injections were made at lower lumbar levels. Following the injection, the syringe is rotated slightly and removed. Topotecan was dissolved with 10% DMSO or 50 mM tartrate acid buffer in 0.9% saline. Comparable vehicle injections were made in control mice.

Intracerebroventricular Drug Infusions.

Mice with paternal Ube3a-YFP ($Ube3a^{m+/pYFP}$) were anesthetized with ketamine/xylazine (120 mg/kg; 9 mg/kg) and positioned in a stereotaxic apparatus. The scalp was shaved and cut, and the skull exposed. The local anesthetic (bupivacaine, 2.5 mg/ml) was applied to the skull, and mineral oil was applied to protect the eyes of the mice. Acetone was applied on the skull to remove any lipid tissues on the skull as well as to dry the skull surface for optimal adhesion. Next, a cannula (Brain Infusion Kit 1, DURECT Corporation) was positioned into a lateral ventricle at the following coordinates (−0.3 mm A/P, +1.0 mm M/L, −2.5 mm D/V), as described[40]. The free end of the cannula was connected to a mini-osmotic pump (Alzet, Model 2001 or 2002) via a 2.5 cm piece of polyethylene (PE) tubing (DURECT Corporation). The mini-osmotic pump and the connecting PE tubing were filled with, respectively for Alzet models 2002 and 2001, 16.34 mM or 47.17 mM topotecan (CPT06, Molcan Corporation) dissolved in 50 mM tartaric acid with 0.9% saline, unless indicated. The filled pumps were incubated in sterile saline at 37° C. for at least 4 hr before being implanted under the dorsal skin of the mouse's back. The cannula base and the attached piece of PE tubing were fixed to the skull with Loctite cyanoacrylic 454. The incision site was closed with prolene suture. During and after surgery, mice were placed on a heating pad to maintain body temperature. 14 days (Alzet model 2002) or five days (Alzet model 2001) following minipump implantation, mice were sacrificed following pentobarbital overdose (150 mg/kg, i.p.) and brains were removed for immunofluorescence staining or pharmacokinetic analysis.

Pharmacokinetic Analysis of Topotecan.

Total topotecan concentrations in blood and brain homogenate were determined by Liquid Chromatography/Triple Quadrupole Mass Spectrometry (HPLC/MS-MS). The HPLC-MS/MS system consisted of two Shimadzu Scientific (Columbia, Md.) solvent delivery pumps, a Valco (Houston, Tex.) switching valve, a thermostated (6° C.) LEAP HTC autosampler (Carrboro, N.C.), and an Applied Biosystems (Foster City, Calif.) API3000 triple quadruple mass spectrometer. Reversed-phase gradient chromatography was used to elute the compounds from an Aquasil (C18 3 µm, 50×2.1 mm) analytical column at a flow rate of 0.3 mL/min, following a 10 µL injection. Starting conditions for each injection were 85% aqueous (0.1% v/v formic acid in water)

and 15% organic (0.1% v/v formic acid in methanol). This was held constant for 0.7 min. After 0.7 min, the organic phase increased linearly to 95% 4.5 min post-injection. The solvent composition was held at 95% organic for 0.5 min to wash the column. The column was re-equilibrated to starting conditions for the final 1 min. Total run time was 6 min. Eluent was diverted to waste for the first 1.5 min. After 1.5 min post-injection, 100% of the eluent was directed to the mass spectrometer. The mass spectrometer was connected to the HPLC system by a TurboIonSpray interface. User controlled voltages, gas pressures, and source temperature were optimized via direct infusion of topotecan, d6-topotecan (internal standard) and irinotecan (internal standard). All were analyzed in positive ion mode using the following transitions preset in multiple reaction monitoring scans: topotecan 422.0→377.1, d6-topotecan (428.0→377.1) and irinotecan 587.2→587.2 (parent to parent transition). To eliminate instrument error due to either in source fragmentation or to cross-talk, care was taken to ensure analytical separation between topotecan and its desmethyl metabolite. Automated sample acquisition and data analysis was performed using Analyst software (version 1.4.1, Applied Biosystems, Foster City, Calif.). Calibration curves, prepared from standards prepared in duplicate using appropriate matrix, were generated based on peak area ratios (analyte: internal standard) and followed a linear fit with $1/x^2$ weighting. The lower limit of topotecan quantitation (LLQ) was 0.01 µM in both blood and brain homogenate (0.03 ng/mg brain). Unknown brain and brain homogenate samples and spiked matrix standards were analyzed following addition of internal standard and protein precipitation using 4× volume of methanol containing formic acid (0.1% v/v). Note that brain homogenates were taken from entire hemispheres; because the homogenates included the ventricular cerebrospinal fluid where drug is likely to accumulate, the drug concentrations likely overestimate the concentrations in parenchymal brain tissue.

REFERENCES FOR EXAMPLE 16

1. Kishino, T., Lalande, M. & Wagstaff, J. UBE3A/E6-AP mutations cause Angelman syndrome. *Nature Genetics* 15, 70-73 (1997).
2. Matsuura, T. et al. De novo truncating mutations in E6-AP ubiquitin-protein ligase gene (UBE3A) in Angelman syndrome. *Nature Genetics* 15, 74-77 (1997).
3. Sutcliffe, J. S. et al. The E6-Ap ubiquitin-protein ligase (UBE3A) gene is localized within a narrowed Angelman syndrome critical region. *Genome Research* 7, 368-377 (1997).
4. Albrecht, U. et al. Imprinted expression of the murine Angelman syndrome gene, Ube3a, in hippocampal and Purkinje neurons. *Nature Genetics* 17, 75-78 (1997).
5. Rougeulle, C., Glatt, H. & Lalande, M. The Angelman syndrome candidate gene, UBE3A/E6-AP, is imprinted in brain. *Nature Genetics* 17, 14-15 (1997).
6. Vu, T. H. & Hoffman, A. R. Imprinting of the Angelman syndrome gene, UBE3A, is restricted to brain. *Nature Genetics* 17, 12-13 (1997).
7. Mabb, A. M., Judson, M. C., Zylka, M. J. & Philpot, B. D. Angelman syndrome: insights into genomic imprinting and neurodevelopmental phenotypes. *Trends in Neurosciences* 34(6):293-303 (2011).
8. Peters, S. U. et al. Double-blind therapeutic trial in Angelman syndrome using betaine and folic acid. *American Journal of Medical Genetics* 152A, 1994-2001 (2010).
9. Chamberlain, S. J. & Brannan, C. I. The Prader-Willi syndrome imprinting center activates the paternally expressed murine Ube3a antisense transcript but represses paternal Ube3a. *Genomics* 73, 316-322 (2001).
10. Landers, M. et al. Regulation of the large (approximately 1000 kb) imprinted murine Ube3a antisense transcript by alternative exons upstream of Snurf/Snrpn. *Nucleic Acids Res* 32, 3480-3492 (2004).
11. Numata, K., Kohama, C., Abe, K. & Kiyosawa, H. Highly parallel SNP genotyping reveals high-resolution landscape of mono-allelic Ube3a expression associated with locus-wide antisense transcription. *Nucleic Acids Res* 39, 2649-2657 (2011).
12. Nakatani, J. et al. Abnormal behavior in a chromosome-engineered mouse model for human 15q11-13 duplication seen in autism. *Cell* 137, 1235-1246 (2009).
13. Jiang, Y. H. et al. Mutation of the Angelman ubiquitin ligase in mice causes increased cytoplasmic p53 and deficits of contextual learning and long-term potentiation. *Neuron* 21, 799-811 (1998).
14. Miura, K. et al. Neurobehavioral and electroencephalographic abnormalities in Ube3a maternal-deficient mice. *Neurobiology of Disease* 9, 149-159 (2002).
15. Dindot, S. V., Antalffy, B. A., Bhattacharjee, M. B. & Beaudet, A. L. The Angelman syndrome ubiquitin ligase localizes to the synapse and nucleus, and maternal deficiency results in abnormal dendritic spine morphology. *Hum. Mol. Genet.* 17, 111-118 (2008).
16. Rougeulle, C., Cardoso, C., Fontes, M., Colleaux, L. & Lalande, M. An imprinted antisense RNA overlaps UBE3A and a second maternally expressed transcript. *Nature Genetics* 19, 15-16 (1998).
17. Runte, M. et al. The IC-SNURF-SNRPN transcript serves as a host for multiple small nucleolar RNA species and as an antisense RNA for UBE3A. *Hum. Mol. Genet.* 10, 2687-2700 (2001).
18. Watanabe, Y. et al. Genome-wide analysis of expression modes and DNA methylation status at sense-antisense transcript loci in mouse. *Genomics* 96, 333-341 (2010).
19. Pommier, Y. Topoisomerase I inhibitors: camptothecins and beyond. *Nature Rev. Cancer* 6, 789-802 (2006).
20. Hertzberg, R. P. et al. Modification of the hydroxy lactone ring of camptothecin: inhibition of mammalian topoisomerase I and biological activity. *J. Med. Chem.* 32, 715-720 (1989).
21. Plaschkes, I., Silverman, F. W. & Priel, E. DNA topoisomerase I in the mouse central nervous system: Age and sex dependence. *J. Comp. Neurol.* 493, 357-369 (2005).
22. Scheffner, M., Nuber, U. & Huibregtse, J. M. Protein ubiquitination involving an E1-E2-E3 enzyme ubiquitin thioester cascade. *Nature* 373, 81-83 (1995).
23. Beaudenon, S., Dastur, A. & Huibregtse, J. M. Expression and assay of HECT domain ligases. *Methods Enzymol.* 398, 112-125 (2005).
24. Kumar, S., Kao, W. H. & Howley, P. M. Physical interaction between specific E2 and Hect E3 enzymes determines functional cooperativity. *Journal of Biological Chemistry* 272, 13548-13554 (1997).
25. Bressler, J. et al. The SNRPN promoter is not required for genomic imprinting of the Prader-Willi/Angelman domain in mice. *Nat Genet* 28, 232-240 (2001).
26. Reik, W. Stability and flexibility of epigenetic gene regulation in mammalian development. *Nature* 447, 425-432 (2007).
27. Gammon, D. C. et al. Intrathecal topotecan in adult patients with neoplastic meningitis. *Am J Health Syst Pharm* 63, 2083-2086 (2006).

28. Lyu, Y. L. et al. Role of topoisomerase IIbeta in the expression of developmentally regulated genes. *Mol. Cell. Biol.* 26, 7929-7941 (2006).
29. Greer, P. L. et al. The Angelman Syndrome protein Ube3A regulates synapse development by ubiquitinating arc. *Cell* 140, 704-716 (2010).
30. Bomgaars, L., Berg, S. L. & Blaney, S. M. The development of camptothecin analogs in childhood cancers. *Oncologist* 6, 506-516 (2001).
32. Cushman, M. et al. Synthesis of new indeno[1,2-c] isoquinolines: cytotoxic non-camptothecin topoisomerase I inhibitors. *J Med Chem* 43, 3688-3698 (2000).
33. Nagarajan, M. et al. Synthesis and evaluation of indenoisoquinoline topoisomerase I inhibitors substituted with nitrogen heterocycles. *J Med Chem* 49, 6283-6289 (2006).
34. Abramoff, M. D., Magelhaes, P. J. & Ram, S. J. Image Processing with ImageJ. *Biophotonics International* 11, 36-42 (2004).
35. Lamprecht, M. R., Sabatini, D. M. & Carpenter, A. E. CellProfiler: free, versatile software for automated biological image analysis. *Biotechniques* 42, 71-75 (2007).
36. Tsai, T. F., Armstrong, D. & Beaudet, A. L. Necdin-deficient mice do not show lethality or the obesity and infertility of Prader-Willi syndrome. *Nat Genet* 22, 15-16 (1999).
37. Landers, M. et al. Regulation of the large (approximately 1000 kb) imprinted murine Ube3a antisense transcript by alternative exons upstream of Snurf/Snrpn. *Nucleic Acids Res* 32, 3480-3492 (2004).
38. Peery, E. G., Elmore, M. D., Resnick, J. L., Brannan, C. I. & Johnstone, K. A. A targeted deletion upstream of Snrpn does not result in an imprinting defect. *Mamm Genome* 18, 255-262 (2007).
39. Fairbanks, C. A. Spinal delivery of analgesics in experimental models of pain and analgesia. *Adv. Drug. Deliv. Rev.* 55, 1007-1041 (2003).
40. Pierce, A. A. & Xu, A. W. De novo neurogenesis in adult hypothalamus as a compensatory mechanism to regulate energy balance. *J Neurosci* 30, 723-730 (2010).
41. Leone, S., Cornetta, T., Basso, E. & Cozzi, R. Resveratrol induces DNA double-strand breaks through human topoisomerase II interaction. *Cancer Lett* 295, 167-172 (2010).
42. Lopez-Lazaro, M., Calderon-Montano, J. M., Burgos-Moron, E. & Austin, C. A. Green tea constituents (−)-epigallocatechin-3-gallate (EGCG) and gallic acid induce topoisomerase I- and topoisomerase II-DNA complexes in cells mediated by pyrogallol-induced hydrogen peroxide. *Mutagenesis* 26, 489-498 (2011).
43. Berger, S. J., Gupta, S., Belfi, C. A., Gosky, D. M. & Mukhtar, H. Green tea constituent (−)-epigallocatechin-3-gallate inhibits topoisomerase I activity in human colon carcinoma cells. *Biochem Biophys Res Commun* 288, 101-105 (2001).
44. Markovits, J. et al. Inhibitory effects of the tyrosine kinase inhibitor genistein on mammalian DNA topoisomerase II. *Cancer Res* 49, 5111-5117 (1989).
45. Snyder, R. D. & Gillies, P. J. Reduction of genistein clastogenicity in Chinese hamster V79 cells by daidzein and other flavonoids. *Food Chem Toxicol* 41, 1291-1298 (2003).
46. Cantero, G., Campanella, C., Mateos, S. & Cortes, F. Topoisomerase II inhibition and high yield of endoreduplication induced by the flavonoids luteolin and quercetin. *Mutagenesis* 21, 321-325 (2006).
47. Snyder, R. D. & Gillies, P. J. Evaluation of the clastogenic, DNA intercalative, and topoisomerase II-interactive properties of bioflavonoids in Chinese hamster V79 cells. *Environ Mol Mutagen* 40, 266-276 (2002).
48. Boege, F. et al. Selected novel flavones inhibit the DNA binding or the DNA religation step of eukaryotic topoisomerase I. *J Biol Chem* 271, 2262-2270 (1996).
49. Lopez-Lazaro, M., Willmore, E. & Austin, C. A. The dietary flavonoids myricetin and fisetin act as dual inhibitors of DNA topoisomerases I and II in cells. *Mutat Res* 696, 41-47 (2010).

TABLE 1

Multiple structurally-distinct topoisomerase inhibitors unsilence paternal Ube3a. Fourteen topoisomerase inhibitors have been discovered to unsilence the paternal Ube3a allele and increase protein expression in cortical neurons. These include two structurally distinct topoisomerase type 1 inhibitors, the camptothecins and indenoisoquinolines. Two topoisomerase type II inhibitors have also been shown to unsilence Ube3a. Efficacy ($E_{max}$) is the level of Ube3a-YFP fluorescence intensity above control cells (0.2% DMSO treated). $EC_{50}$ is the half maximal effective drug concentration in nanomoles.

| Parent Compound | Compound | Mechanism of action | Efficacy $E_{max}$ (fold over control) | $EC_{50}$ (nM) |
|---|---|---|---|---|
| Camptothecin | Belotecan (CKD602) | Topoisomerase 1 inhibitor | 1.85 ± 0.04 | 18 ± 1:1 |
| Camptothecin | Camptothecin (CPT) | Topoisomerase 1 inhibitor | 1.66 ± 0.06 | 32 ± 1.3 |
| Camptothecin | 7-Ethyl-10-Hydroxy-CPT | Topoisomerase 1 inhibitor | 2.00 ± 0.09 | 33 ± 1.3 |
| Camptothecin | 10-Hydroxy-CPT | Topoisomerase 1 inhibitor | 1.68 ± 0.06 | 40 ± 1.4 |
| Camptothecin | Rubitecan (9-Nitro-CPT) | Topoisomerase 1 inhibitor | 2.07 ± 0.08 | 43 ± 9.1 |
| Camptothecin | 7-Ethyl-CPT | Topoisomerase 1 inhibitor | 1.68 ± 0.05 | 49 ± 1.3 |
| Camptothecin | Topotecan | Topoisomerase 1 inhibitor | 2.25 ± 0.07 | 54 ± 1.2 |
| Camptothecin | Irinotecan | Topoisomerase 1 inhibitor | 2.19 ± 0.06 | 994 ± 10 |

TABLE 1-continued

Multiple structurally-distinct topoisomerase inhibitors unsilence paternal Ube3a. Fourteen topoisomerase inhibitors have been discovered to unsilence the paternal Ube3a allele and increase protein expression in cortical neurons. These include two structurally distinct topoisomerase type 1 inhibitors, the camptothecins and indenoisoquinolines. Two topoisomerase type II inhibitors have also been shown to unsilence Ube3a. Efficacy ($E_{max}$) is the level of Ube3a-YFP fluorescence intensity above control cells (0.2% DMSO treated). $EC_{50}$ is the half maximal effective drug concentration in nanomoles.

| Parent Compound | Compound | Mechanism of action | Efficacy $E_{max}$ (fold over control) | $EC_{50}$ (nM) |
|---|---|---|---|---|
| Camptothecin | Silatecan (DB67) | Topoisomerase 1 inhibitor | 1.71 ± 0.06 | 2640 ± 95 |
| Indenoisoquinoline | NSC706744 | Topoisomerase 1 inhibitor | 1.76 ± 0.03 | 6.2 ± 2 |
| Indenoisoquinoline | NSC725776 | Topoisomerase 1 inhibitor | 1.82 ± 0.05 | 9.2 ± 2 |
| Indenoisoquinoline | NSC724998 | Topoisomerase 1 inhibitor | 1.65 ± 0.03 | 12 ± 4 |
| Acridine derivative | Amsacrine | Topoisomerase 2 inhibitor | 1.65 ± 0.05 | 28 ± 10 |
| Bisdioxopiperazine | ICRF-193 | Topoisomerase 2 inhibitor | 2.51 ± 0.1 | 131 ± 13 |

TABLE 2

Lentivirus shRNA

| Gene | NM ID | Clone ID | Sequence |
|---|---|---|---|
| TopI | NM_009408 | TRCN0000011883 | CCGGCCACAAGTCTTAACAAACCAACTCGAGTTGGTTTGTTAAGACTTGTGGTTTTT |
|  |  | TRCN0000011884 | CCGGCCAGCGAAGATTCTATCTTATCTCGAGATAAGATAGAATCTTCGCTGGTTTTT |
|  |  | TRCN0000011885 | CCGGCGATTGAATGATTCTCACAAACTCGAGTTTGTGAGAATCATTCAATCGTTTTT |
|  |  | TRCN0000011886 | CCGGCCGCCACGAATTAAAGATGAACTCGAGTTCATCTTTAATTCGTGGCGGTTTTT |
|  |  | TRCN0000011887 | CCGGGCAGTCTAAGATTGATGCCAACTCGAGTTGGCATCAATCTTAGACTGCTTTTT |
| TopIIa | NM_011623 | TRCN0000070983 | CCGGCCCGAGTTTGAAGAATGGAAACTCGAGTTTCCATTCTTCAAACTCGGGTTTTG |
|  |  | TRCN0000070984 | CCGGCCTCTCTAATAACAGACTATACTCGAGTATAGTCTGTTATTAGAGAGGTTTTG |
|  |  | TRCN0000070985 | CCGGGCTCGCTTTATATTAGAGAAACTCGAGTTTCTCTAATATAAAGCGAGCTTTTG |
|  |  | TRCN0000070986 | CCGGGCAGACTACATTGCCGTTTAACTCGAGTTAAACGGCAATGTAGTCTGCTTTTG |
|  |  | TRCN0000070987 | CCGGCCAGCAGATTAGCTTCGTCAACTCGAGTTGACGAAGCTAATCTGCTGGTTTTG |
| TopIIb | NM_009409 | TRCN0000070988 | CCGGCCTTGTGTTGTCCTTTGTCTTCTCGAGAAGACAAAGGACAACACAAGGTTTTG |
|  |  | TRCN0000070989 | CCGGCCGCCAAATCTCTAGCTGTATCTCGAGATACAGCTAGAGATTTGGCGGTTTTG |
|  |  | TRCN0000070990 | CCGGCGCAGCTATGTAGACCTTTATCTCGAGATAAAGGTCTACATAGCTGCGTTTTG |
|  |  | TRCN0000070991 | CCGGGCTAGAGAAATTGTGAACAATCTCGAGATTGTTCACAATTTCTCTAGCTTTTG |
|  |  | TRCN0000070992 | CCGGCCCATTGTAAAGGCAAGCAAACTCGAGTTTGCTTGCCITTACAATGGGTTTTG | siRNA

| TopI |  | CCTTTGAGAAGTCAATGATTT |
|---|---|---|
|  |  | CCGAAATCAGTATCGGGAATT |
|  |  | CAATTGAGAAGATTTACAATT |
| TopIIb |  | CTGTTAGTGGTGAGATATTTT |
|  |  | GACTATAAACTCTGACTCATT |
|  |  | CCTGATACCACAGTAGTGATT |

TABLE 3

Efficacies and potencies of topoisomerase inhibitors for unsilencing the paternal allele of Ube3a-YFP in cultured neurons.

| Compound | Potency $EC_{20}$ (nM) | Efficacy $E_{max}$ (fold over vehicle) |
|---|---|---|
| 7-Ethyl-Camptothecin (7-Ethyl-CPT) | 7.2 ± 2.3 | 1.70 ± 0.04 |
| 7-Ethyl-10-Hydroxy-CPT | 11 ± 3.2 | 1.99 ± 0.06 |
| 10-Hydroxy-CPT | 14 ± 5.7 | 1.82 ± 0.08 |
| Belotecan (CKD602) | 19 ± 4.4 | 1.88 ± 0.05 |
| Camptothecin (CPT) | 21 ± 3.8 | 2.11 ± 0.05 |
| Topotecan* | 54 ± 3.4 | 2.25 ± 0.05 |
| Rubitecan (9-Nitro-CPT) | 62 ± 18 | 2.09 ± 0.09 |

TABLE 3-continued

Efficacies and potencies of topoisomerase inhibitors for unsilencing the paternal allele of Ube3a-YFP in cultured neurons.

| Compound | Potency $EC_{20}$ (nM) | Efficacy $E_{max}$ (fold over vehicle) |
|---|---|---|
| Irinotecan* | 994 ± 13 | 2.17 ± 0.05 |
| Silatecan (DB67) | 2244 ± 171 | 1.65 ± 0.05 |
| Lactam E ring-CPT (inactive) | inactive | inactive |
| NSC725776 | 10 ± 1.6 | 1.76 ± 0.03 |
| NSC706744 | 11 ± 3.2 | 1.84 + 0.07 |
| NSC724998 | 14 ± 2.2 | 1.69 ± 0.03 |
| Etoposide* | 1600 ± 980 | 1.68 ± 0.04 |
| ICRF-193 | 205 ± 70 | 2.21 ± 0.09 |
| Dexrazoxane (ICRF-187)* | 20470 ± 1450 | 1.82 ± 0.05 |
| Amsacrine | 27 ± 5.2 | 1.74 ± 0.06 |

(NSC725776, NSC706744 and NSC724998 = indenoisoquinoline derivatives, Etoposide = podophyllotoxin derivative, ICRF-193 and Dexrazoxane (ICRF-187) = bis-dioxopiperazine derivatives, and Amsacrine = aminoacridine derivative; all others = camtothecin derivatives).

TABLE 4

| Primer | Sequence (5' to 3') | Reference (if applicable) |
|---|---|---|
| Ube3a F | CAAAAGGTGCATCTAACAACTCA | |
| Ube3ce R | GGGGAATAATCCTCACTCTCTC | |
| Snrpn 1-3 F | TTGGTTCTGAGGAGTGATTTGC | 36 |
| Snrpn 3 R | CCTTGAATTCCACCACCTTG | 36 |
| Ipw B/C F | TCACCACAACACTGGACAAAA | 37 |
| Ipw B/C R | TGCTGCTACACAGGAAAGAGG | 37 |
| Ube3a-ATS F | GGCACCCTTGTTTGAAACTT | |
| Ube3a-ATS R | GCTCATGACCCTGTCCTTTC | |
| Rpl22 F | AAGAAGCAGGTTTTGAAG | |
| Rpl22 R | TGAAGTGACAGTGATCTTG | |
| Actb F | CAGCTTCTTTGCAGCTCCTT | |
| Actb R | CACGATGGAGGGGAATACAG | |

What is claimed is:

1. A method of treating Angelman syndrome or Rett syndrome in a human subject, comprising administering to the subject an effective amount of a topoisomerase I inhibitor without a DNA methyltransferase inhibitor, wherein the topoisomerase I inhibitor is a camptothcin derivative or an indenoisoquinoline derivative, thereby treating Angelman syndrome or Rett syndrome in the subject.

2. The method of claim 1, wherein the camptothcin derivative is selected from the group consisting of Belotecan (CKD602), Camptothecin, 7-Ethyl-10-Hydroxy-CPT, 10-Hydroxy-CPT, Rubitecan (9-Nitro-CPT), 7-Ethyl-CPT, Topotecan, Irinotecan, Silatecan (DB67) and any combination thereof.

3. The method of claim 1, wherein the indenoisoquinoline derivative is selected from the group consisting of NSC706744, NSC725776, NSC724998 and any combination thereof.

4. The method of claim 1, wherein the topoisomerase I inhibitor has an efficiency $E_{max}$ of at least 1.5 fold over control.

5. The method of claim 1, wherein the topoisomerase I inhibitor has an efficiency $E_{max}$ of at least 2.5 fold over control.

* * * * *

UNITED STATES PATENT AND TRADEMARK OFFICE
CERTIFICATE OF CORRECTION

PATENT NO. : 9,714,427 B2
APPLICATION NO. : 13/883621
DATED : July 25, 2017
INVENTOR(S) : Philpot et al.

It is certified that error appears in the above-identified patent and that said Letters Patent is hereby corrected as shown below:

On the Title Page

Item (56) References Cited:
Other Publications, Page 2, right column, Item Lopez-Lazarq:
Please correct "Lopez-Lazarq et al." to read -- Lopez Lazaro et al. --

Other Publications, Page 3, right column, Item Watanabe et al.:
Please correct "methylation status status at" to read -- methylation status at --

Other Publications, Page 4: Please add the following:
-- Maab et al. "Angelman Syndrome: Insights into Genomic Imprinting and Neurodevelopmental Phenotypes" *Trends in Neurosciences* 34(6):293-303 (2011) --

In the Specification

Column 8, Line 18: Please correct "Scale bar=50" to read -- Scale Bar=50μm --

Column 10, Line 22: Please correct "(Ube3a$^{m-/p-}$)" to read -- (Ube3a$^{m+/p-}$) --

Column 18, Line 18: Please correct "with 14μM" to read -- with 10μM --
    Line 49: Please correct "(Abeam) and" to read -- (Abcam) and --

Column 19, Line 39: Please correct "(Lt.), starting" to read -- (i.t.), starting --

Column 37, Line 5: Please correct "(Abeam, 1:500)" to read -- (Abcam, 1:500) --

Column 38, Line 15: Please correct "in 5 unless" to read -- in 5μL unless --

Signed and Sealed this
Twenty-seventh Day of February, 2018

Andrei Iancu
*Director of the United States Patent and Trademark Office*

CERTIFICATE OF CORRECTION (continued)
U.S. Pat. No. 9,714,427 B2

Columns 43-44, Table 2, Gene "Top IIb NM_009409, TRCN0000070992:
Please correct sequence to read
-- CCGGCCCATTGTAAAGGCAAGCAAACTCGAGTTTGCTTGCCTTT
ACAATGGGTTTTTG --